(12) United States Patent
Ryu et al.

(10) Patent No.: US 7,943,646 B2
(45) Date of Patent: May 17, 2011

(54) BENZAMIDINE DERIVATIVE, PROCESS FOR THE PREPARATION THEREOF AND PHARMACEUTICAL COMPOSITION COMPRISING SAME

(75) Inventors: Jei Man Ryu, Anyang-si (KR); Jin Soo Lee, Yongin-si (KR); Young Goo Jin, Seoul (KR); Ki Young Lee, Seoul (KR); Jae Hoon Park, Seoul (KR); Yun Ha Hwang, Gunpo-si (KR); Sae Kwang Ku, Suwon-si (KR)

(73) Assignee: Dong Wha Pharmaceutical Co., Ltd., Seoul (KR)

( * ) Notice: Subject to any disclaimer, the term of this patent is extended or adjusted under 35 U.S.C. 154(b) by 344 days.

(21) Appl. No.: 12/162,701

(22) PCT Filed: Jan. 31, 2007

(86) PCT No.: PCT/KR2007/000533
§ 371 (c)(1),
(2), (4) Date: Jul. 30, 2008

(87) PCT Pub. No.: WO2007/089101
PCT Pub. Date: Aug. 9, 2007

(65) Prior Publication Data
US 2009/0054642 A1 Feb. 26, 2009

(30) Foreign Application Priority Data
Jan. 31, 2006 (KR) .................. 10-2006-0009459

(51) Int. Cl.
*C07D 277/22* (2006.01)
*A61K 31/426* (2006.01)
*A61K 31/155* (2006.01)
*A61P 19/10* (2006.01)

(52) U.S. Cl. ........................................ 514/365; 548/198

(58) Field of Classification Search .................. 548/198; 514/365
See application file for complete search history.

(56) References Cited

FOREIGN PATENT DOCUMENTS

| | | |
|---|---|---|
| DE | 19755268 A1 | 6/1999 |
| EP | 1375482 A1 | 1/2004 |
| KR | 1020060017929 A | 2/2006 |
| WO | WO 03007947 A1 | 1/2003 |
| WO | WO-2006/004369 A1 | 1/2006 |
| WO | WO2006/014087 A1 | 2/2006 |
| WO | PCT/KR2007/000533 | 8/2007 |

OTHER PUBLICATIONS

English Translation of Abstract; Korean Publication No. KR1020060017929(A); Applicant: Dong Wha Pharm Ind. Co., LTD. Published Feb. 28, 2006 (Abstract only) (1 PG).
European Search Report dated Aug. 5, 2010, issued in corresponding European patent application EP 07708686.6.

Primary Examiner — Kahsay T Habte
(74) Attorney, Agent, or Firm — Arent Fox LLP

(57) ABSTRACT

The present invention relates to a novel benzamidine derivative, a process for the preparation thereof, and a pharmaceutical composition comprising the same. The benzamidine derivative of the present invention effectively inhibits osteoclast differentiation at an extremely low concentration, and greatly increases the trabecular bone volume, and thus it can be advantageously used for the prevention and treatment of osteoporosis.

18 Claims, No Drawings

BENZAMIDINE DERIVATIVE, PROCESS FOR THE PREPARATION THEREOF AND PHARMACEUTICAL COMPOSITION COMPRISING SAME

TECHNICAL FIELD

The present invention relates to a novel benzamidine derivative, a process for the preparation thereof and a pharmaceutical composition comprising the same.

BACKGROUND ART

Bone is a supporting material for the body's framework and serves to conserve the necessary bone mass and structure. Bone also functions as a reservoir of calcium ($Ca^{2+}$) or the like, and plays an important role in maintaining the calcium level in the blood. To this end, the growth of bone is a metabolic balance between the activity of osteoblasts and osteoclasts in the bone remodelling cycle. Accordingly, bone is in a steady state, which maintains good balance between bone absorption and bone formation in the metabolism by continuously performing both bone absorption and bone formation. When the balance between bone absorption and bone formation is disrupted, the degree of bone absorption is relatively higher than that of bone formation, which may lead to osteoporosis, a condition which causes reduction in bone density or bone mass, resulting in decrease in bone strength. This is a disease which frequently occurs in middle-aged or elderly women.

Osteoporosis is a disease, which results from a disturbance in the balance between bone absorption and bone formation, and is caused by having a higher degree of bone absorption relative to that of bone formation. Osteoporosis reduces calcification of bone tissues, and decreases the level of the compact substances in the bone, which broadens the marrow cavity. As osteoporosis progresses, bone becomes brittle, and bone fracture may easily occur even with a small impact. Bone is a steady state structure, in which the bone formation by osteoblast and the bone resorption by osteoclast occur continuously.

Previous studies on osteoporosis have focused mainly on the metabolism of bone minerals, such as calcium and phosphorus. However, such studies did not provide sufficient findings on the mechanisms of osteoporosis.

Although bisphosphonate (alendronate, etidronate, etc.), Estrogen receptor modulator (raloxifen), vitamin D, calcitonin, calcium agents, or the like have been used as an anti-osteoporotic agent, they are known to have adverse effects. Specifically, bisphosphonte agents show low absorptivity and may induce esophagitis, in addition to being difficult to dose. Hormone agents must be administered throughout patient's life, and in the case of long-term administration, side effects such as breast cancer, uterus cancer, gallstones and thrombosis may be induced. Vitamin D agents are expensive and show little efficacy, while calcitonin agents are also very expensive and difficult to administer. Calcium agents have few side effects, but their effects are restricted to the prevention of osteoporosis, not the treatment itself.

It is known osteoporosis cannot be treated with a short-term administration of drugs, and generally requires long-term administration. Therefore, there is a need for a novel substance having excellent efficacy, without the above-mentioned side effects in the long-term administration.

DISCLOSURE

Technical Problem

The present inventors have extensive studies on an effective agent for treating osteoporosis, and synthesized a novel benzamidine derivative, which was found to have excellent effect of inhibiting bone resorption by osteoclast and thus of treating and preventing osteoporosis, thereby completing the present invention.

Technical Solution

It is an object of the present invention to provide a novel benzamidine derivative.

It is another object of the present invention to provide a method for preparing the novel benzamidine derivative.

It is still another object of the present invention to provide a pharmaceutical composition for the prevention and treatment of osteoporosis, comprising the novel benzamidine derivative.

BEST MODE

In one embodiment, the present invention provides a novel benzamidine derivative represented by the following formula 1.

[Formula 1]

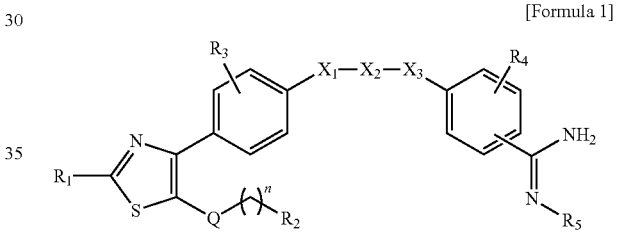

wherein $R_1$ is $C_1$ to $C_6$ alkyl which is unsubstituted or substituted with one group selected from pyridine and

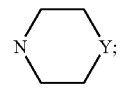

$C_3$ to $C_6$ cycloalkyl; phenyl; benzyl; pyridinyl which is unsubstituted or substituted with $C_1$ to $C_6$ alkyl; guanidino; $NR_6R_7$; $CH_2NR_6R_7$

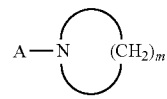

(wherein A is $C_1$ to $C_6$ alkyl, and m is an integer of 2 to 6); or

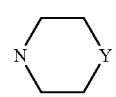

group which is unsubstituted or substituted with $C_1$ to $C_6$ alkyl;

$R_2$ is a primary or secondary amine, which is $NR_8R_9$,

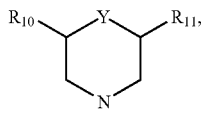

pyrrolidine, piperidine or imidazole;

$R_3$ and $R_4$ are each independently hydrogen; halogen; hydroxy; $C_1$ to $C_6$ alkyl which is unsubstituted or substituted with halogen; $C_3$ to $C_6$ cycloalkylamino; $C_1$ to $C_6$ alkoxy; $C_1$ to $C_6$ alkanoyloxy; $C_2$ to $C_6$ alkenyloxy; phenyl—$C_1$ to $C_6$ alkoxy; phenoxy; $C_2$ to $C_6$ alkenoyloxy or phenyl—$C_1$ to $C_6$ alkanoyloxy; or $C_3$ to $C_6$ cycloalkyloxy which is substituted with one group selected from carboxy, esterified carboxy and amidated carboxy; or aminooxy;

$R_5$ is hydrogen or hydroxy group;

$R_6$ and $R_7$ are each independently hydrogen; $C_1$ to $C_6$ alkyl which is unsubstituted or substituted with one group selected from hydroxy, $C_1$ to $C_6$ alkoxy, pyridine and

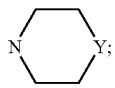

phenyl; benzyl; pyridinyl; carbonyl which is unsubstituted or substituted with one group selected from $C_1$ to $C_6$ alkyl, hydroxy, $C_1$ to $C_6$ alkoxy, phenyl, benzyl, pyridine and

or $C_1$ to $C_6$ alkanesulfonyl;

$R_8$ and $R_9$ are each independently hydrogen; $C_1$ to $C_6$ alkyl which is unsubstituted or substituted with one group selected from hydroxy, $C_1$ to $C_6$alkoxy, morpholine, imidazole and $NR_6R_7$; $C_1$ to $C_6$alkoxy; $C_3$ to $C_6$cycloalkyl; phenyl; benzyl; pyridinyl; morpholine; carbonyl which is unsubstituted or substituted with one group selected from $C_1$ to $C_6$ alkyl, $C_1$ to $C_6$ alkoxy, phenyl, benzyl, pyridine and

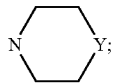

carbonyl substituted with $C_1$ to $C_6$ alkyl which is substituted with one group selected from halogen, $C_1$ to $C_6$ alkoxy and imidazole; or $C_1$ to $C_6$ alkanesulfonyl;

$R_{10}$ and $R_{11}$ are each independently hydrogen, $C_1$ to $C_2$ alkyl, $C_1$ to $C_3$alkoxy or halide;

$X_1$ and $X_3$ are each independently O; S; NH; or N—$C_1$ to $C_6$ alkyl, N—$C_3$ to $C_6$ cycloalkyl, N-benzyl or N-phenyl;

$X_2$ is $C_3$ to $C_7$ alkylene; $C_1$ to $C_3$ alkylene-$C_2$ to $C_7$alkenylene-$C_1$ to $C_3$ alkylene; $C_1$ to $C_3$ alkylene-O—$C_1$ to $C_3$ alkylene; $C_1$ to $C_3$ alkylene-S—$C_1$ to $C_3$ alkylene; $C_1$ to $C_3$ alkylene-NH—$C_1$ to $C_3$ alkylene; $C_1$ to $C_3$ alkylene-phenylene-$C_1$-$C_3$ alkylene; $C_1$-$C_3$ alkylene-pyridylene-$C_1$-$C_3$ alkylene or $C_1$-$C_3$ alkylene-naphthylene-$C_1$ to $C_3$ alkylene; $C_3$ to $C_7$ alkylene which is substituted with $C_1$ to $C_3$ alkyl and hydroxyl; $C_3$ to $C_7$ alkylene carbonyl; or $C_3$ to $C_7$ alkylene which is interrupted by piperazine;

Y is O, S, $NR_6$ or $CH_2$;

Q is $CH_2$ or carbonyl; and n is an integer of 0 to 6.

In the formula 1, particularly $R_1$ is methyl, ethyl, isopropyl, cyclohexyl, phenyl, pyridinyl, $NR_6R_7$, $CH_2NR_6R_7$,

or

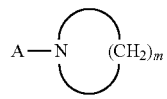

(wherein A is $C_1$ to $C_2$ alkyl, and m is an integer of 4 to 5);

$R_2$ is a primary or secondary amine, which is $NR_8R_9$,

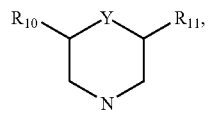

piperidine or imidazole;

$R_3$ and $R_4$ are each independently hydrogen, methyl, ethyl, halogen, hydroxy or methoxy; $R_5$ is hydrogen or hydroxy;

$R_6$ and $R_7$ are each independently hydrogen, methyl, ethyl, isobutyryl, methoxyethyl, 2-morpholinoethyl or benzyl;

$R_8$ and $R_9$ are each independently hydrogen; methyl; ethyl; propyl; isopropyl; butyl; isobutyl; t-butyl; cyclopropyl; cyclohexyl; ethyl which is substituted with one group selected from hydroxy, methoxy, 2-morpholino and $NR_6R_7$; propyl which is substituted with one group selected from 3-isopropoxy and 3-imidazole; carbonyl which is substituted with one group selected from 3-pyridinyl, 4-pyridinyl and isopropyl;

$R_{10}$ and $R_{11}$ are each independently hydrogen or methyl;

$X_1$ and $X_3$ are each independently oxygen, sulfur, amine or methylamine;

$X_2$ is propylene, butylene, pentylene, hexylene, ethylene-O-ethylene, ethylene-NH-ethylene, butylene carbonyl, 2-butenyl, methylene-1,2-phenylene-methylene, methylene-1,3-phenylene-methylene, methylene-1,4-phenylene-methylene or methylene-pyridinyl-methylene;

Y is O, S or methylamino;

Q is $CH_2$ or carbonyl; and n is an integer of 0 to 3.

In the compound of the formula 1 of the present invention, $R_3$ and $R_4$ are in the ortho or meta position relative to —O—$(CH_2)_5$—O—, and —$C(NH_2)$=N—$R_5$ are in the meta or para position.

The preferred compounds among the benzamidine derivatives of the formula 1 of the present invention are as follows:

1) N-hydroxy-(5-{4-[5-(2-isobutylamino-ethyl)-2-methyl-thiazol-4-yl]-phenoxy}-pentyloxy)-benzamidine,
2) 4-(5-{4-[5-(2-isobutylaminoethyl)-2-methyl-thiazol-4-yl]-phenoxy}-pentyloxy)-benzamidine,
3) N-hydroxy-4-(5-{4-[2-methyl-5-(2-piperidin-1-yl-ethyl)-thiazol-4-yl]-phenoxy}-pentyloxy)-benzamidine, 4) N-hydroxy-4-[5-(4-{2-methyl-5-[2-(2-morpholin-4-yl-ethylamino)-ethyl]-thiazol-4-yl}-phenoxy)-pentyloxy]-benzamidine,
5) N-hydroxy-4-[5-(4-{5-[2-(3-imidazol-1-yl-propylamino)-ethyl]-2-methyl-thiazol-4-yl}-phenoxy)-pentyloxy]-benzamidine,
6) N-hydroxy-4-(5-{4-[5-(2-isopropylamino-ethyl)-2-methyl-thiazol-4-yl]-phenoxy}-pentyloxy)-benzamidine,
7) N-hydroxy-4-[5-(4-{5-[2-(3-isopropoxy-propylamino)-ethyl]-2-methyl-thiazol-4-yl}-phenoxy)-pentyloxy]-benzamidine,
8) N-hydroxy-4-(5-{4-[5-(2-butylamino-ethyl)-2-methyl-thiazol-4-yl]-phenoxy}-pentyloxy)-N-hydroxy-benzamidine,
9) N-hydroxy-4-(5-{4-[5-(2-imidazol-1-yl-ethyl)-2-methyl-thiazol-4-yl]-phenoxy}-pentyloxy)-benzamidine,
10) N-hydroxy-4-(5-{4-[5-(2-cyclohexylamino-ethyl)-2-methyl-thiazol-4-yl]-phenoxy}-pentyloxy)-benzamidine,
11) N-hydroxy-4-(5-{4-[5-(2-diethylamino-ethyl)-2-methyl-thiazol-4-yl]-phenoxy}-pentyloxy)-benzamidine,
12) N-hydroxy-4-{5-[4-(5-{2-[bis-(2-hydroxy-ethyl)-amino]-ethyl}-2-methyl-thiazol-4-yl)-phenoxy]-pentyloxy}-benzamidine,
13) N-hydroxy-4-(5-{4-[5-(2-diisopropylamino-ethyl)-2-methyl-thiazol-4-yl]-phenoxy}-pentyloxy)-benzamidine,
14) N-hydroxy-4-[5-(4-{5-[2-(2,6-dimethyl-morpholin-4-yl)-ethyl]-2-methyl-thiazol-4-yl}-phenoxy)-pentyloxy]-benzamidine,
15) N-hydroxy-4-(5-{4-[2-methyl-5-(2-thiomorpholin-4-yl-ethyl)-thiazol-4-yl]-phenoxy}-pentyloxy)-benzamidine,
16) N-hydroxy-4-(5-{4-[2-amino-5-(2-morpholin-4-yl-ethyl)-thiazol-4-yl]-phenoxy}-pentyloxy)-benzamidine,
17) N-hydroxy-4-[5-(4-{5-[2-(2-dimethylamino-ethylamino)-ethyl]-2-methyl-thiazol-4-yl}-phenoxy)-pentyloxy]-benzamidine,
18) N-hydroxy-4-(5-{4-[2-methyl-5-(2-morpholin-4-yl-ethyl)-thiazol-4-yl]-phenoxy}-pentyloxy)-benzamidine,
19) N-hydroxy-4-[5-(4-{2-methyl-5-[2-(4-methyl-piperazin-1-yl)-ethyl]-thiazol-4-yl}-phenoxy)-pentyloxy]-benzamidine,
20) N-hydroxy-4-{5-[4-(5-{2-[bis-(2-methoxy-ethyl)-amino]-ethyl}-2-methyl-thiazol-4-yl)-phenoxy]-pentyloxy}-benzamidine,
21) N-hydroxy-4-(5-{4-[5-(2-tert-butylamino-ethyl)-2-methyl-thiazol-4-yl]-phenoxy}-pentyloxy)-benzamidine,
22) N-hydroxy-4-(5-{4-[5-(2-isobutylamino-ethyl)-2-methyl-thiazol-4-yl]-phenoxy}-pentyloxy)-benzamidine,
23) N-hydroxy-4-(5-{4-[5-(2-morpholin-4-yl-ethyl)-2-pyridine-3-yl-thiazol-4-yl]-phenoxy}-pentyloxy)-benzamidine,
24) N-hydroxy-4-[5-(4-{5-[2-(4-methyl-piperazin-1-yl)-ethyl]-2-pyridine-3-yl-thiazol-4-yl}-phenoxy)-pentyloxy]-benzamidine,
25) N-hydroxy-4-(5-{4-[2-pyridine-3-yl-5-(2-thiomorpholin-4-yl-ethyl)-thiazol-4-yl]-phenoxy}-pentyloxy)-benzamidine,
26) N-hydroxy-4-(5-{4-[5-(2-imidazol-1-yl-ethyl)-2-pyridine-3-yl-thiazol-4-yl]-phenoxy}-pentyloxy)-benzamidine,
27) N-hydroxy-4-(5-{4-[2-isopropyl-5-(2-morpholin-4-yl-ethyl)-thiazol-4-yl]-phenoxy}-pentyloxy)-benzamidine,
28) N-hydroxy-4-[5-(4-{2-isopropyl-5-[2-(4-methyl-piperazin-1-yl)-ethyl]-thiazol-4-yl}-phenoxy)-pentyloxy]-benzamidine,
29) N-hydroxy-4-(5-{4-[5-(2-imidazol-1-yl-ethyl)-2-isopropyl-thiazol-4-yl]-phenoxy}-pentyloxy)-benzamidine,
30) N-hydroxy-4-[5-(4-{2-isopropyl-5-[2-(2-morpholin-4-yl-ethylamino)-ethyl]-thiazol-4-yl}-phenoxy)-pentyloxy]-benzamidine,
31) N-hydroxy-4-[5-(4-{5-[2-(3-imidazol-1-yl-propylamino)-ethyl]-2-isopropyl-thiazol-4-yl}-phenoxy)-pentyloxy]-benzamidine,
32) N-hydroxy-4-(5-{4-[2-isopropyl-5-(2-thiomorpholin-4-yl-ethyl)-thiazol-4-yl]-phenoxy}-pentyloxy)-benzamidine,
33) N-hydroxy-4-(5-{4-[2-cyclohexyl-5-(2-morpholin-4-yl-ethyl)-thiazol-4-yl]-phenoxy}-pentyloxy)-benzamidine,
34) N-hydroxy-4-[5-(4-{2-cyclohexyl-5-[2-(4-methyl-piperazin-1-yl)-ethyl]-thiazol-4-yl}-phenoxy)-pentyloxy]-benzamidine,
35) N-hydroxy-4-[5-(4-{2-cyclohexyl-5-[2-(2-morpholin-4-yl-ethylamino)-ethyl]-thiazol-4-yl}-phenoxy)-pentyloxy]-benzamidine,
36) N-hydroxy-4-(5-{4-[2-cyclohexyl-5-(2-thiomorpholin-4-yl-ethyl)-thiazol-4-yl]-phenoxy}-pentyloxy)-benzamidine,
37) N-hydroxy-4-(5-{4-[2-cyclohexyl-5-(2-dimethylamino-ethyl)-thiazol-4-yl]-phenoxy}-pentyloxy)-benzamidine,
38) N-hydroxy-4-(5-{4-[2-cyclohexyl-5-(2-dipropylamino-ethyl)-thiazol-4-yl]-phenoxy}-pentyloxy)-benzamidine,
39) N-hydroxy-4-(5-{4-[2-cyclohexyl-5-(2-cyclopropylamino-ethyl)-thiazol-4-yl]-phenoxy}-pentyloxy)-benzamidine,
40) N-hydroxy-4-[5-(4-{2-amino-5-[2-(2-morpholin-4-yl-ethylamino)-ethyl]-thiazol-4-yl}-phenoxy)-pentyloxy]-benzamidine,
41) N-hydroxy-4-(5-{4-[5-(2-morpholin-4-yl-ethyl)-2-phenyl-thiazol-4-yl]-phenoxy}-pentyloxy)-benzamidine,
42) N-hydroxy-4-(5-{4-[2-ethyl-5-(2-morpholin-4-yl-ethyl)-thiazol-4-yl]-phenoxy}-pentyloxy)-benzamidine,
43) N-hydroxy-4-(5-{4-[2-ethyl-5-(2-thiomorpholin-4-yl-ethyl)-thiazol-4-yl]-phenoxy}-pentyloxy)-benzamidine,
44) N-hydroxy-4-(4-{4-[2-methyl-5-(2-morpholin-4-yl-ethyl)-thiazol-4-yl]-phenoxy}-butoxy)-benzamidine,
45) 4-(5-{4-[2-cyclohexyl-5-(2-morpholin-4-yl-ethyl)-thiazol-4-yl]-phenoxy}-pentyloxy)-benzamidine,
46) 4-(5-{4-[2-methyl-5-(2-morpholin-4-yl-ethyl)-thiazol-4-yl]-phenoxy}-pentyloxy)-benzamidine,
47) N-hydroxy-4-(5-{4-[2-methylamino-5-(2-morpholin-4-yl-ethyl)-thiazol-4-yl]-phenoxy}-pentyloxy)-benzamidine,
48) N-hydroxy-4-[5-(4-{2-methylamino-5-[2-(4-methyl-piperazin-1-yl)-ethyl]-thiazol-4-yl}-phenoxy)-pentyloxy]-benzamidine,
49) N-hydroxy-4-(5-{4-[2-methylamino-5-(2-thiomorpholin-4-yl-ethyl)-thiazol-4-yl]-phenoxy}-pentyloxy)-benzamidine,
50) N-hydroxy-4-[5-(4-{2-methylamino-5-[2-(2-morpholin-4-yl-ethylamino)-ethyl]-thiazol-4-yl}-phenoxy)-pentyloxy]-benzamidine,
51) N-hydroxy-4-[5-(4-{5-[2-(3-imidazol-1-yl-propylamino)-ethyl]-2-methylamino-thiazol-4-yl}-phenoxy)-pentyloxy]-benzamidine,
52) 4-(5-{4-[2-methylamino-5-(2-morpholin-4-yl-ethyl)-thiazol-4-yl]-phenoxy}-pentyloxy)-benzamidine,
53) N-hydroxy-4-(5-{4-[2-dimethylamino-5-(2-morpholin-4-yl-ethyl)-thiazol-4-yl]-phenoxy}-pentyloxy)-benzamidine,
54) N-hydroxy-4-(5-{4-[2-dimethylamino-5-(2-thiomorpholin-4-yl-ethyl)-thiazol-4-yl]-phenoxy}-pentyloxy)-benzamidine, 55) N-hydroxy-4-(5-{4-[2-(isobutyryl-methyl-amino)-5-(2-morpholin-4-yl-ethyl)-thiazol-4-yl]-phenoxy}-pentyloxy)-benzamidine,
56) N-hydroxy-4-(5-{4-[2-[benzyl-(2-morpholin-4-yl-ethyl)-amino]-5-(2-morpholin-4-yl-ethyl)-thiazol-4-yl]-phenoxy}-pentyloxy)-benzamidine,
57) N-hydroxy-4-(5-{4-[2-diethylamino-5-(2-morpholin-4-yl-ethyl)-thiazol-4-yl]-phenoxy}-pentyloxy)-benzamidine,
58) N-hydroxy-4-(5-{4-[2-[bis-(2-methoxy-ethyl)-amino]-5-(2-morpholin-4-yl-ethyl)-thiazol-4-yl]-phenoxy}-pentyloxy)-benzamidine,
59) N-hydroxy-4-(5-{4-[2-morpholin-4-yl-5-(2-morpholin-4-yl-ethyl)-thiazol-4-yl]-phenoxy}-pentyloxy)-benzamidine,
60) N-hydroxy-4-(5-{4-[2-morpholin-4-yl-5-(2-thiomorpholin-4-yl-ethyl)-thiazol-4-yl]-phenoxy}-pentyloxy)-benzamidine,
61) N-hydroxy-4-[5-(4-{5-[2-(4-methyl-piperazin-1-yl)-ethyl]-2-morpholin-4-yl-thiazol-4-yl}-phenoxy)-pentyloxy]-benzamidine,
62) N-hydroxy-4-[5-(4-{2-morpholin-4-yl-5-[2-(2-morpholin-4-yl-ethylamino)-ethyl]-thiazol-4-yl}-phenoxy)-pentyloxy]-benzamidine,
63) N-hydroxy-4-(5-{4-[5-(2-morpholin-4-yl-ethyl)-2-piperidin-1-yl-methyl-thiazol-4-yl]-phenoxy}-pentyloxy)-benzamidine,
64) 4-(5-{4-[2-morpholin-4-yl-5-(2-morpholin-4-yl-ethyl)-thiazol-4-yl]-phenoxy}-pentyloxy)-benzamidine,
65) N-hydroxy-(5-{4-[5-(2-isobutyrylamino-ethyl)-2-methyl-thiazol-4-yl]-phenoxy}-pentyloxy)-benzamidine,
66) N-hydroxy-4-{5-[4-(5-{2-[isobutyl-(pyridine-3-carbonyl)-amino]-ethyl}-2-methyl-thiazol-4-yl)-phenoxy]-pentyloxy}-benzamidine,
67) N-hydroxy-4-{5-[4-(5-{2-[cyclopropyl-(pyridine-4-carbonyl)-amino]-ethyl}-2-isopropyl-thiazol-4-yl)-phenoxy]-pentyloxy}-benzamidine,
68) N-hydroxy-4-{5-[4-(2-cyclohexyl-5-{2-[cyclopropyl-(pyridine-3-carbonyl)-amino]-ethyl}-thiazol-4-yl)-phenoxy]-pentyloxy}-benzamidine,
69) N-hydroxy-4-{5-4-(5-methylcarbamoyl-2-methyl-thiazol-4-yl)-phenoxy]-pentyloxy}-benzamidine,
70) N-hydroxy-4-{5-[4-(5-isopropylcarbamoyl-2-methyl-thiazol-4-yl)-phenoxy]-pentyloxy}-benzamidine,
71) N-hydroxy-4-{5-[4-(5-{3-imidazol-1-yl-propylcarbamoyl}-2-methyl-thiazol-4-yl)-phenoxy]-pentyloxy}-benzamidine, and
72) N-hydroxy-4-{5-[4-(2-amino-5-methylcarbamoyl-thiazol-4-yl)-phenoxy]-pentyloxy}-benzamidine.

The benzamidine derivative of the formula 1 of the present invention may be used in the form of a pharmaceutically acceptable salt, and as the salt, acid addition salts prepared with pharmaceutically acceptable free acids are preferred. As the free acids, inorganic acids or organic acids may be used. Examples of the inorganic acids include hydrochloric acid, bromic acid, sulfuric acid, and phosphoric acid, and examples of the organic acids include citric acid, acetic acid, lactic acid, tartaric acid, fumaric acid, formic acid, propionic acid, oxalic acid, trifluoroacetic acid, methane sulfonic acid, benzene sulfonic acid, maleic acid, benzoic acid, gluconic acid, glycolic acid, succinic acid, 4-morpholine ethane sulfonic acid, camphorsulfonic acid, 4-nitrobenzene sulfonic acid, hydroxy-0-sulfonic acid, 4-toluene sulfonic acid, galacturonic acid, embonic acid, glutamic acid, and aspartic acid. Preferably, hydrochloric acid as the inorganic acid and methane sulfonic acid as the organic acid can be used.

In the present invention, general definitions of the substituents of the compound of the formula 1 have the following meanings:

The term "halogen" means halogen group atoms including chlorine, fluorine, bromine, and iodine radicals.

The term "alkyl" radical means straight or branched, saturated hydrocarbon radicals having 1 to 6 carbon atoms, and include, for example, methyl, ethyl, n-propyl, iso-propyl, n-butyl, sec-butyl and tert-butyl.

The term "alkoxy" means radicals having straight or branched alkyl having 1 to 6 carbon atoms linked to oxygen, and include, for example, methoxy, ethoxy, propoxy, iso-propoxy butoxy, sec-butoxy, and tert-butoxy.

The term "cycloalkyl" means a nonaromatic hydrocarbon ring having 3 to 6 carbon atoms on the each ring, and include, for example, cyclopropyl, cyclobutyl, cyclopentyl and cyclohexyl.

The term "alkenyl" means straight or branched, unsaturated hydrocarbons having 2 to 6 carbon atoms with one or more double bonds.

The term "alkanoyloxy" means an oxygen-containing radical in which a terminal carbon atom of an alkyl group is substituted by a carbonyl radical.

The term "alkenoyloxy" means an oxygen-containing radical in which a terminal carbon atom of an alkenyl group is substituted by a carbonyl radical.

The term "alkenyloxy" means an oxygen-containing alkenyl group.

The term "alkylene" means a straight or branched, saturated hydrocarbon radical having 1 to 7 carbon atoms, and 2 or more junction centers for a covalent bond, and include, for example, methylene, ethylene, methylethylene and isopropylidene.

The term "alkenylene" means a straight or branched, unsaturated hydrocarbon radical having 2 to 7 carbon atoms, 2 or more conjunction centers for a covalent bond and one or more double bonds, and include, for example, 1,1-vinylidene (CH$_2$=C), 1,2-vinylidene (—CH=CH—), and 1,4-butadienyl (—CH=CH—CH=CH—).

The term "carbonyl" means a carbon radical in which 2 of 4 covalent bonds are linked to oxygen atoms.

In another embodiment, the present invention provides a method for preparing the benzamidine derivative of the formula 1.

The compound of the formula 1 wherein $R_1$ is $C_1$ to $C_6$ alkyl; $C_1$ to $C_6$ alkyl which is substituted with pyridine; $C_3$ to $C_6$ cycloalkyl; benzyl; phenyl; amino; guanidino; pyridinyl; pyridinyl which is substituted with $C_1$ to $C_6$ alkyl; or

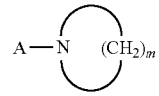

(wherein A is $C_1$ to $C_6$ alkyl, and m is an integer of 2 to 6), and Q is CH$_2$, can be prepared as in Reaction Scheme 1 below comprising the steps of:

1) reacting a compound of the formula 2 with a compound of the formula 3 in the presence of an inorganic base to prepare a compound of the formula 4,
2) reacting a compound of the formula 5 with the compound of the formula 4 obtained in the step 1) in the presence of an inorganic base to prepare a compound of the formula 6,
3) reacting the compound of the formula 6 obtained in the step 2) with an acid chloride compound (7) to prepare a benzonitrile derivative of the formula 8, 4) reacting the compound of the formula 8 obtained in the step 3) with a bromine compound to prepare an alpha-brominated compound of the formula 9, 5) reacting the alpha-brominated compound of the formula 9 obtained in the step 4) with a thioamide compound of the formula 10 to prepare a benzonitrile derivative of the formula 11 with a thiazole ring, 6) reacting the compound of the formula 11 obtained in the step 5) with sodium iodide to prepare a benzonitrile derivative of the formula 12, 7) reacting the compound of the formula 12 obtained in the step 6) with a primary or secondary amine compound of the formula 13 to prepare a benzonitrile derivative of the formula 14, and 8) reacting the compound of the formula 14 obtained in the step 7) with hydroxylamine hydrochloride or an ammonia ethanol solution to prepare a benzamidine derivative of the formula 1a.

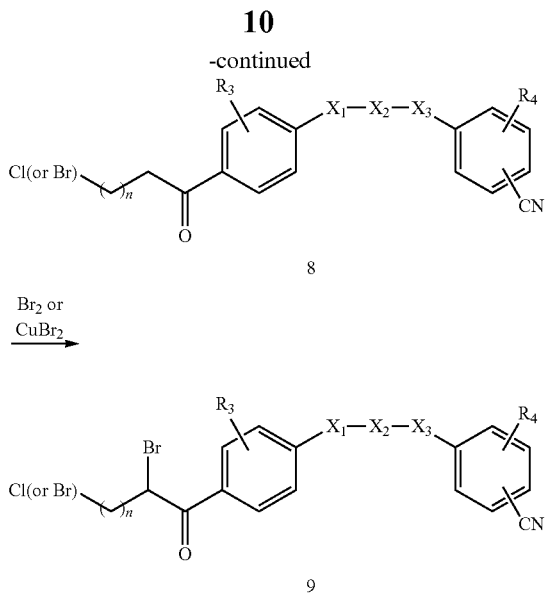

[Reaction Scheme 1]

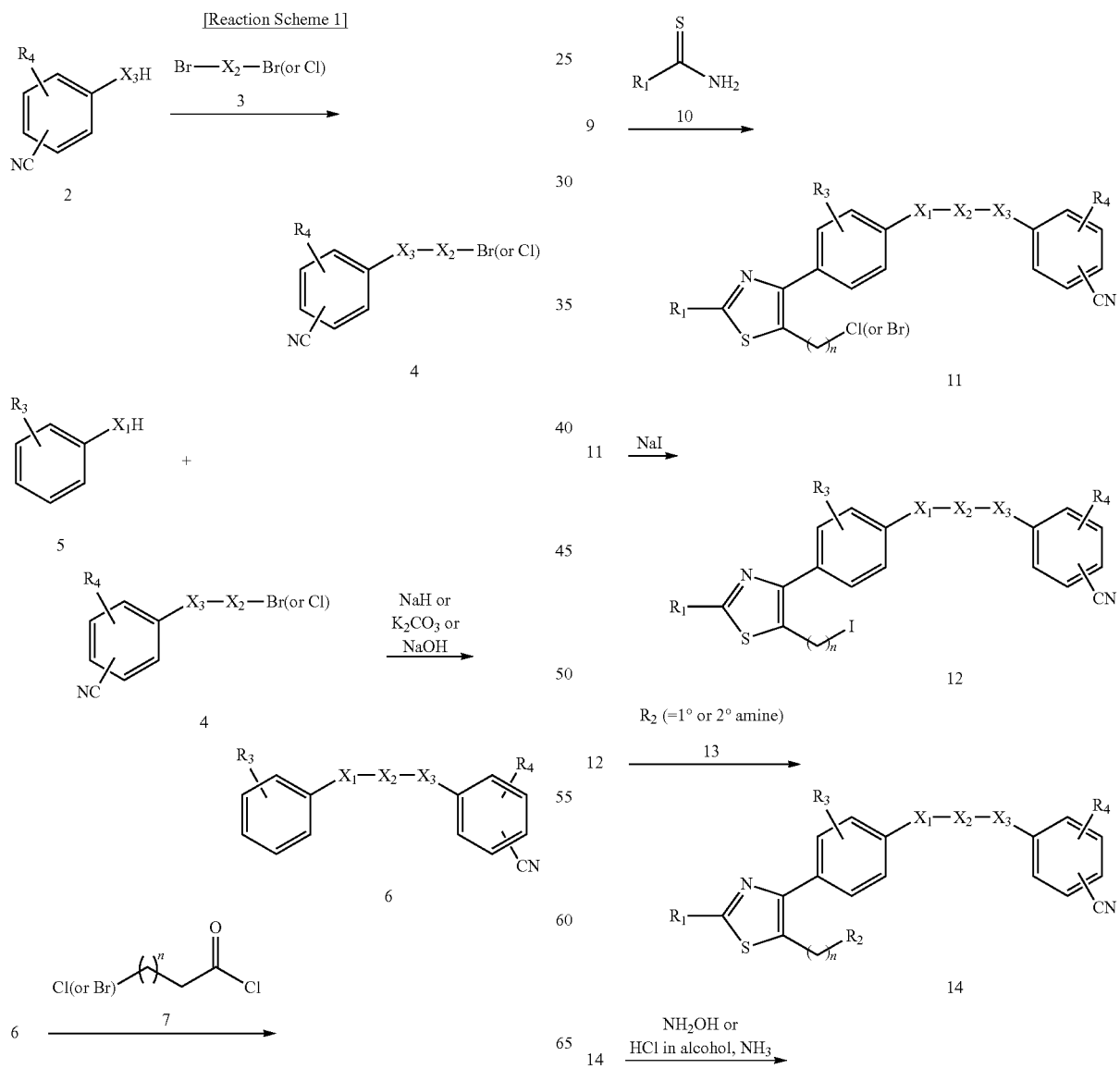

-continued

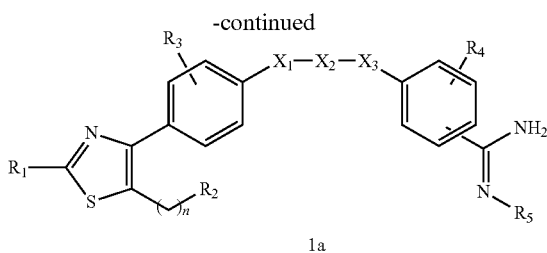

1a wherein $R_2$, $R_3$, $R_4$, $R_5$, $X_1$, $X_2$, $X_3$ and n are the same as defined in the compound of the formula 1.

The compound of the formula 1 wherein $R_1$ is $CH_2NHR_6$ or $NHR_6$ (except that $R_6$ is hydrogen), and Q is $CH_2$, can be prepared as in Reaction Scheme 2 below comprising the steps of:

1) reacting the alpha-brominated compound of the formula 9 obtained in the step 4) of Reaction Scheme 1 with the thioamide compound of the formula 15 to prepare an benzonitrile derivative of the formula 16 with an aminothiazole ring, 2) reacting the compound of the formula 16 obtained in the step 1) with sodium iodide to prepare a benzonitrile derivative of the formula 17, 3) reacting the compound of the formula 17 obtained in the step 2) with a primary or secondary amine compound of the formula 13 to prepare a benzonitrile derivative of the formula 18, 4) reacting the compound of the formula 18 obtained in the step 3) with a halide compound of the formula 19 to prepare a benzonitrile derivative of the formula 20 with a thiazole ring, which is substituted with a primary amine, and 5) reacting the compound of the formula 20 obtained in the step 4) with hydroxylamine hydrochloride or an ammonia ethanol solution to prepare a benzamidine derivative of the formula 1b.

[Reaction Scheme 2]

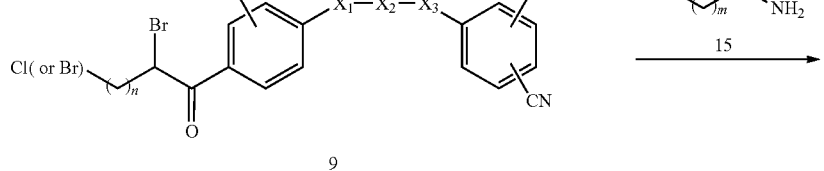

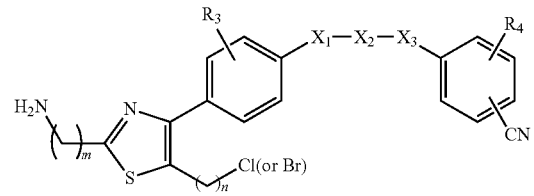

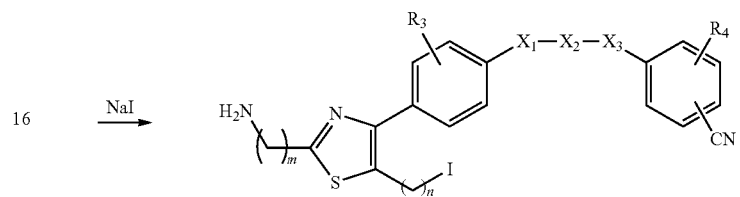

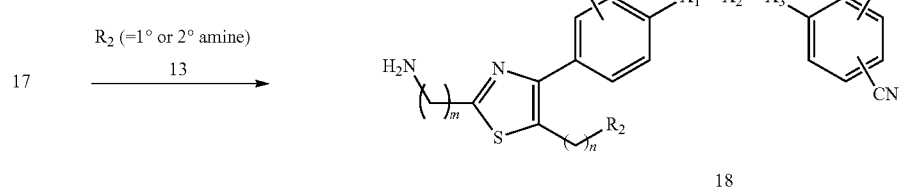

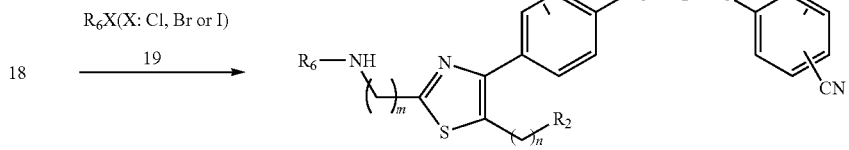

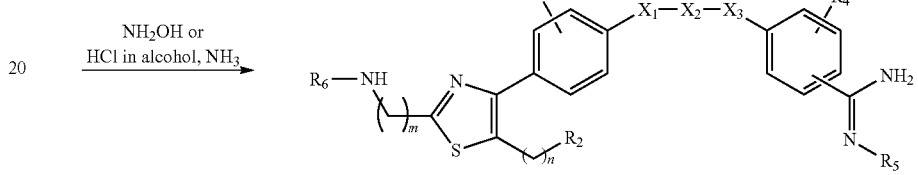

wherein $R_2$, $R_3$, $R_4$, $R_5$, $R_6$, $X_1$, $X_2$ and $X_3$ are the same as defined in the compound of the formula 1, and n and m are each an integer of 0 to 6, except that $R_6$ is hydrogen.

The compound of the formula 1 wherein $R_1$ is $CH_2NR_6R_7$ or $NR_6R_7$ (except that $R_6$ and/or $R_7$ is/are hydrogen) and Q is $CH_2$, can be prepared as in Reaction Scheme 3 below comprising the steps of:

1) reacting the compound of the formula 20 obtained in the step 4) of Reaction Scheme 2 with a halide compound of the formula 21 to prepare a benzonitrile derivative of the formula 22 with a thiazole ring, which is substituted with a secondary amine, and 2) reacting a compound of the formula 22 obtained in the step 1) with hydroxylamine hydrochloride or an ammonia ethanol solution to prepare a benzamidine derivative of the formula 1c.

[Reaction Scheme 3]

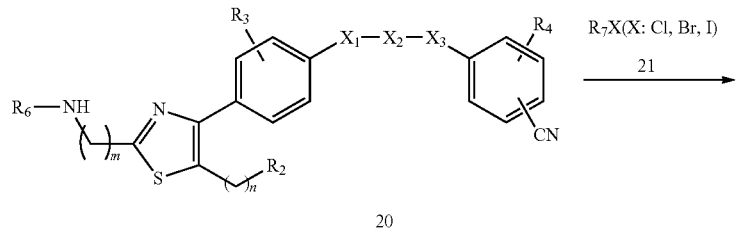

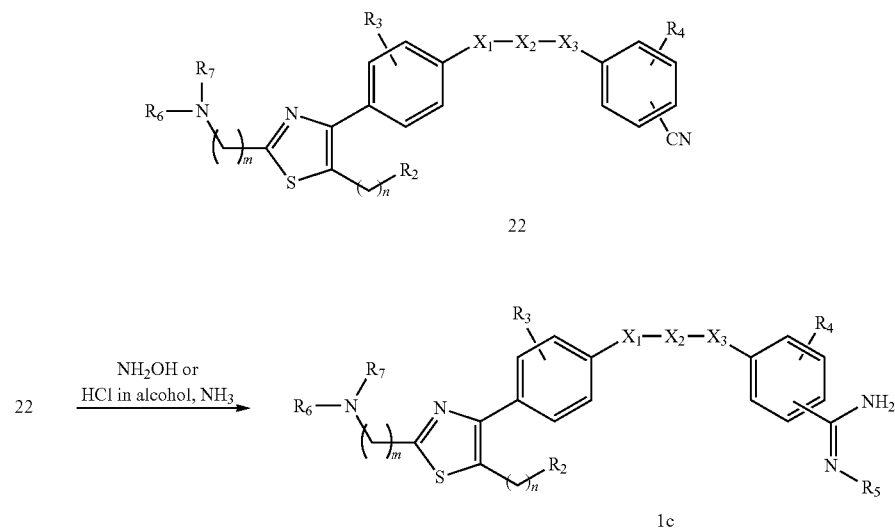

wherein $R_2$, $R_3$, $R_4$, $R_5$, $R_6$, $R_7$, $X_1$, $X_2$ and $X_3$ are the same as defined in the compound of the formula 1, and n and m are each an integer of 0 to 6, except that $R_6$ and/or $R_7$ is/are hydrogen.

The benzamidine derivatives of the formula 1 wherein $R_1$ is $C_1$ to $C_6$ alkyl which is substituted with

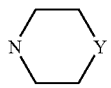

or

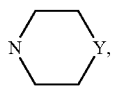

and Q is $CH_2$, can be prepared as in Reaction Scheme 4 below comprising the steps of:

1) reacting the compound of the formula 18 obtained in the step 3) of Reaction Scheme 2 with a compound, of which both terminals are substituted with a halogen, of the formula 23 to prepare a benzonitrile derivative of the formula 24 with a thiazole ring, which is substituted with a heteroring, and 2) reacting a compound of the formula 24 obtained in the step 1) with hydroxylamine hydrochloride or an ammonia ethanol solution to prepare a benzamidine derivative of the formula 1d.

wherein $R_2$, $R_3$, $R_4$, $R_5$, $X_1$, $X_2$, $X_3$ and Y are the same as defined in the compound of the formula 1, and n and m are each an integer of 0 to 6.

The compound of the formula 1 wherein Q is $CH_2$, and $R_2$ is $HNR_8$ (in the case of $R_8$ containing carbonyl, and except that $R_8$ is hydrogen), can be prepared as in Reaction Scheme 5 below comprising the steps of:

1) reacting the compound of the formula 12 obtained in the step 6) of Reaction Scheme 1 with potassium phthalimide to prepare a benzonitrile derivative of the formula 25, 2) reacting the compound of the formula 25 obtained in the step 1) with hydrazine hydrate to prepare a benzonitrile derivative containing an amino group of the formula 26, 3) reacting the compound of the formula 26 obtained in the step 2) with a halide compound of the formula 27 to prepare a benzonitrile derivative which is substituted with a primary amine compound of the formula 14a, and 4) reacting the compound of the formula 14a obtained in the step 3) with hydroxylamine hydrochloride or an ammonia ethanol solution to prepare a benzamidine derivative of the formula 1e.

[Reaction Scheme 4]

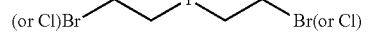

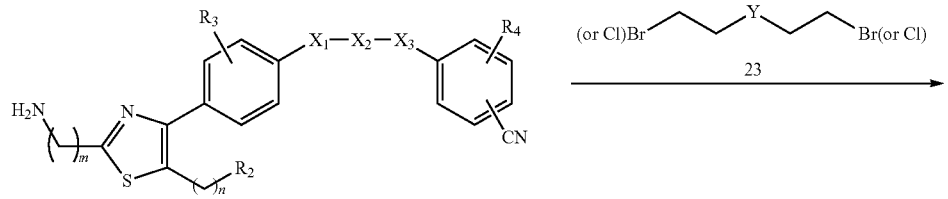

18

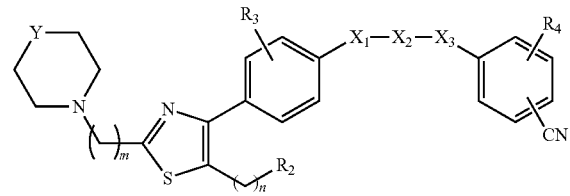

24

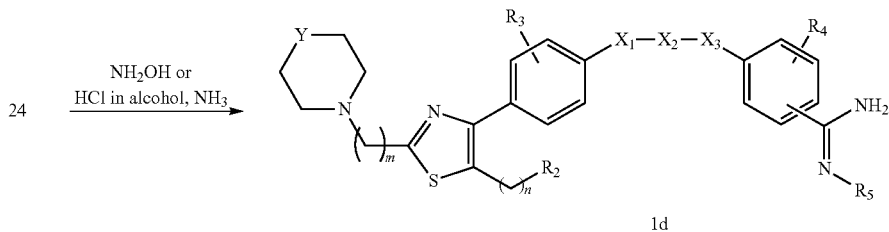

1d

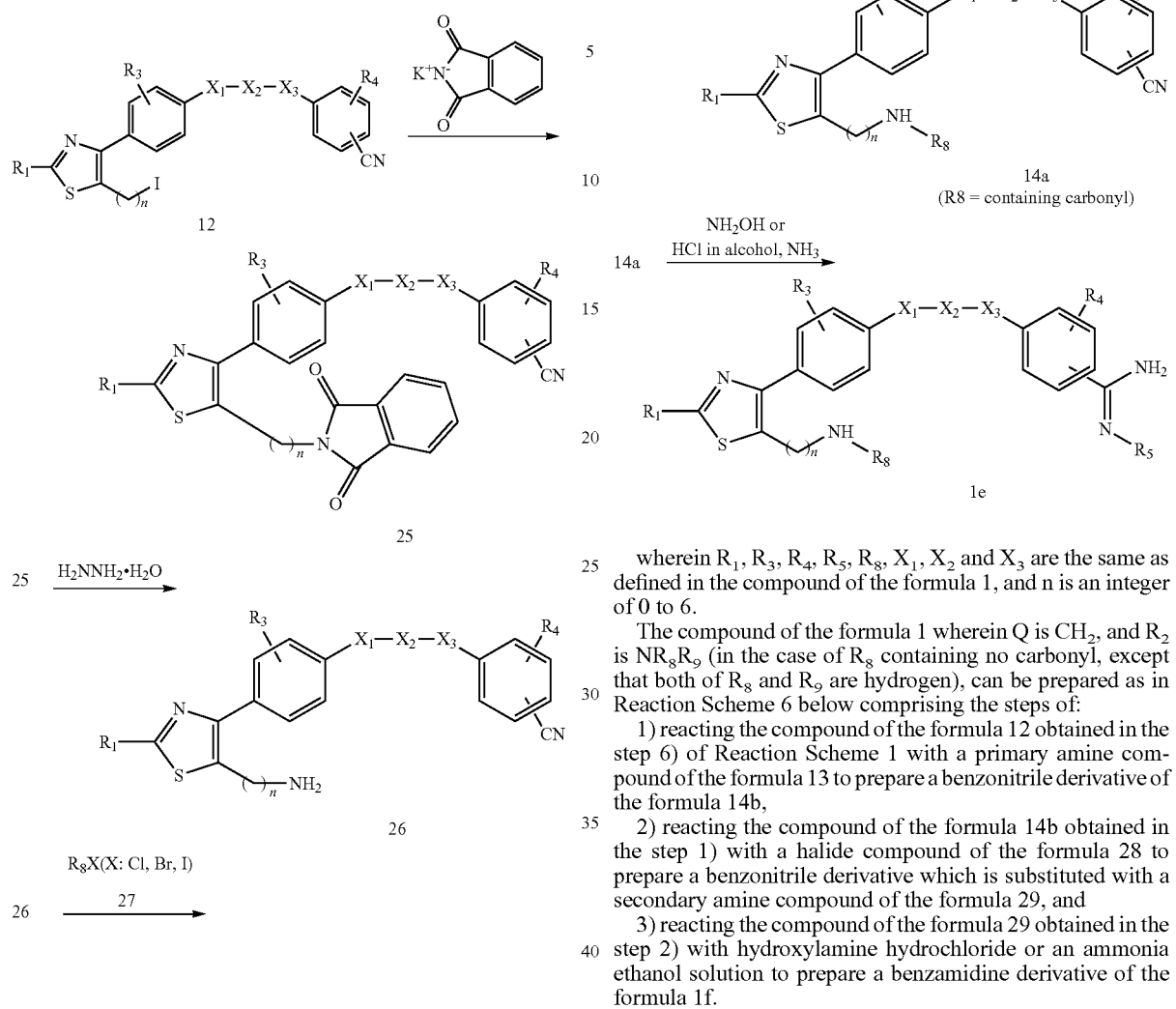

wherein $R_1$, $R_3$, $R_4$, $R_5$, $R_8$, $X_1$, $X_2$ and $X_3$ are the same as defined in the compound of the formula 1, and n is an integer of 0 to 6.

The compound of the formula 1 wherein Q is $CH_2$, and $R_2$ is $NR_8R_9$ (in the case of $R_8$ containing no carbonyl, except that both of $R_8$ and $R_9$ are hydrogen), can be prepared as in Reaction Scheme 6 below comprising the steps of:

1) reacting the compound of the formula 12 obtained in the step 6) of Reaction Scheme 1 with a primary amine compound of the formula 13 to prepare a benzonitrile derivative of the formula 14b, 2) reacting the compound of the formula 14b obtained in the step 1) with a halide compound of the formula 28 to prepare a benzonitrile derivative which is substituted with a secondary amine compound of the formula 29, and 3) reacting the compound of the formula 29 obtained in the step 2) with hydroxylamine hydrochloride or an ammonia ethanol solution to prepare a benzamidine derivative of the formula 1f.

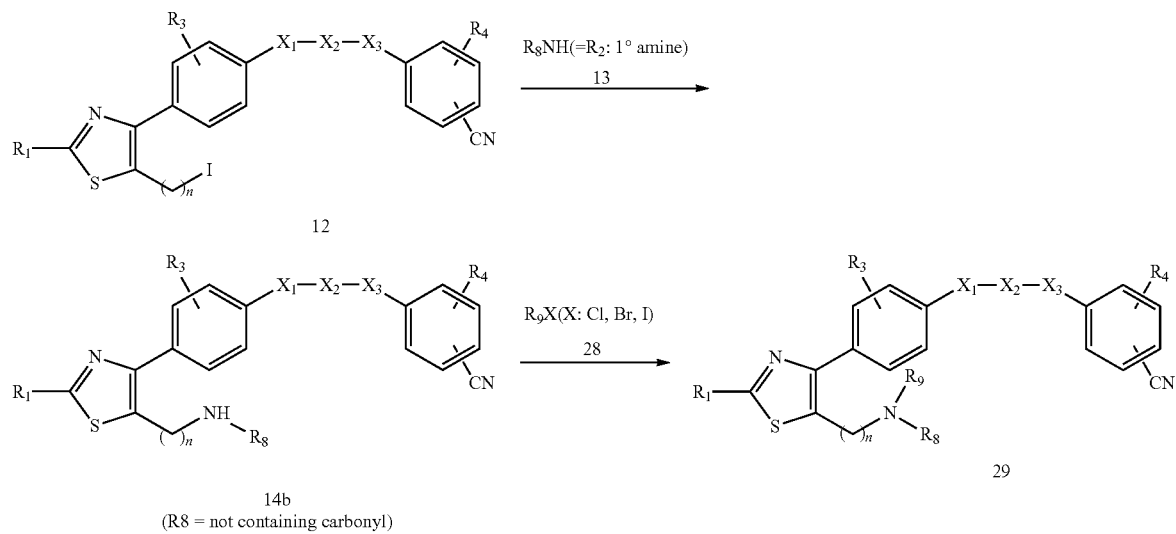

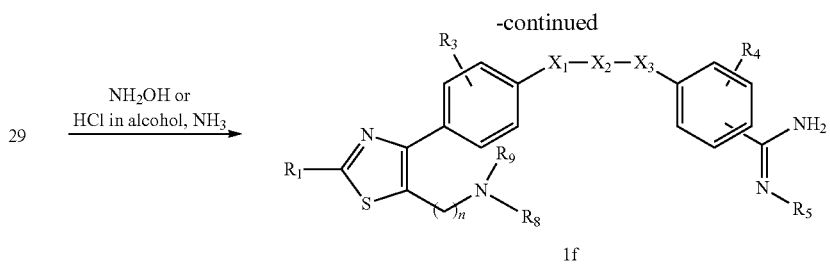

wherein $R_1$, $R_3$, $R_4$, $R_5$, $R_8$, $R_9$, $X_1$, $X_2$ and $X_3$ are the same as defined in the compound of the formula 1, and n is an integer of 0 to 6.

The compound of the formula 1 wherein Q is carbonyl can be prepared as in Reaction Scheme 7 below comprising the steps of:

1) reacting a compound of the formula 30 with the compound of the formula 4 obtained in the step 1) of Reaction Scheme 1 in the presence of an inorganic base to prepare a compound of the formula 31, 2) reacting the compound of the formula 31 obtained in the step 1) with sodium hydride, and diethyl carbonate to prepare a compound of the formula 32, 3) reacting the compound of the formula 32 obtained in the step 2) with a bromine compound to prepare an alpha-brominated compound of the formula 33, 4) reacting the alpha-brominated compound of the formula 33 obtained in the step 3) with a thioamide compound of the formula 10 to prepare a compound of the formula 34 with a thiazole ring, 5) reacting the compound of the formula 34 obtained in the step 4) with lithium hydroxide to prepare a compound of the formula 35, 6) reacting the compound of the formula 35 obtained in the step 5) with isobutyl chloroformate, and a primary or secondary amine compound of the formula 13 to prepare a benzonitrile derivative of the formula 36, and 7) reacting the compound of the formula 36 obtained in the step 6) with hydroxylamine hydrochloride or an ammonia ethanol solution to prepare a benzamidine derivative of the formula 1g.

[Reaction Scheme 7]

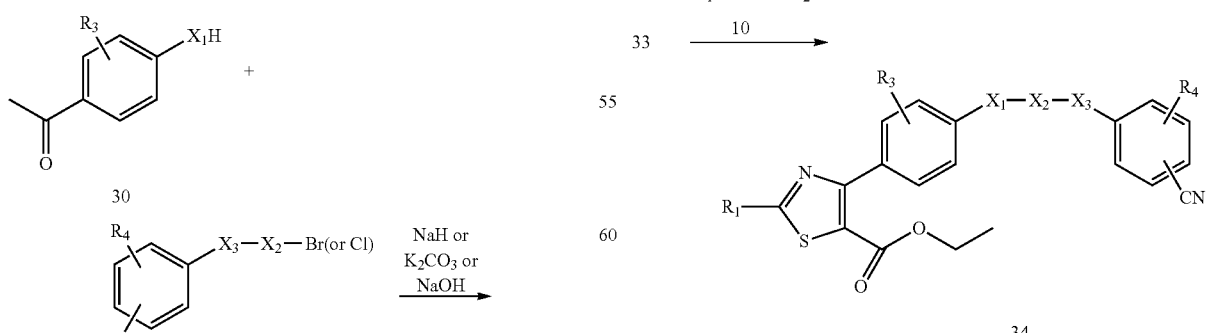

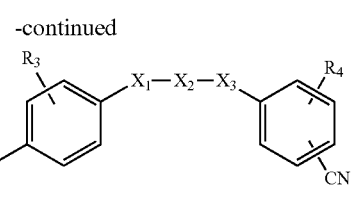

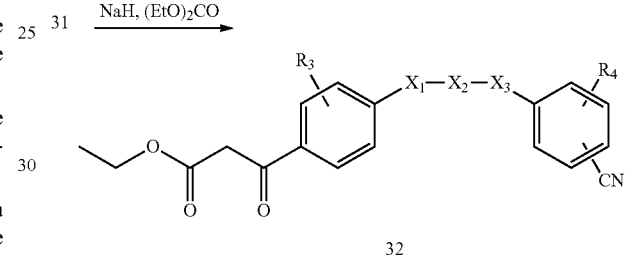

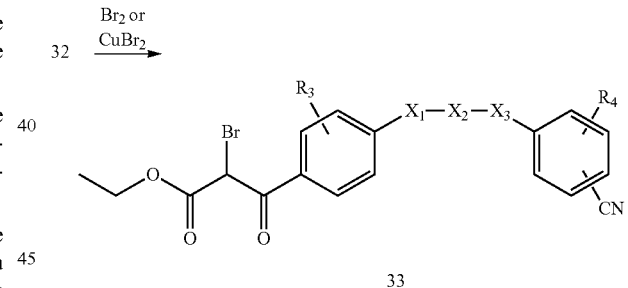

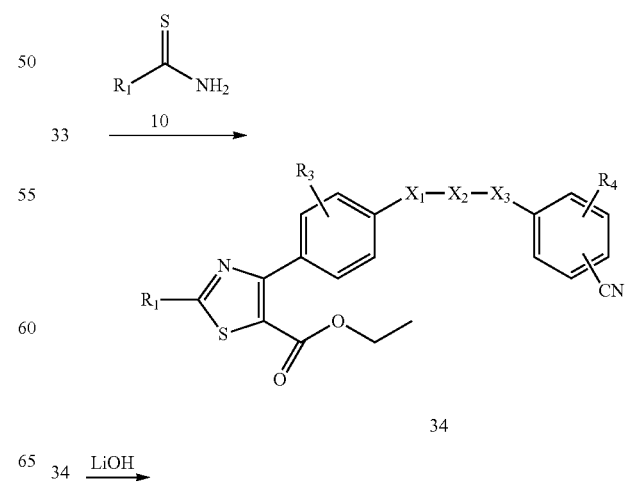

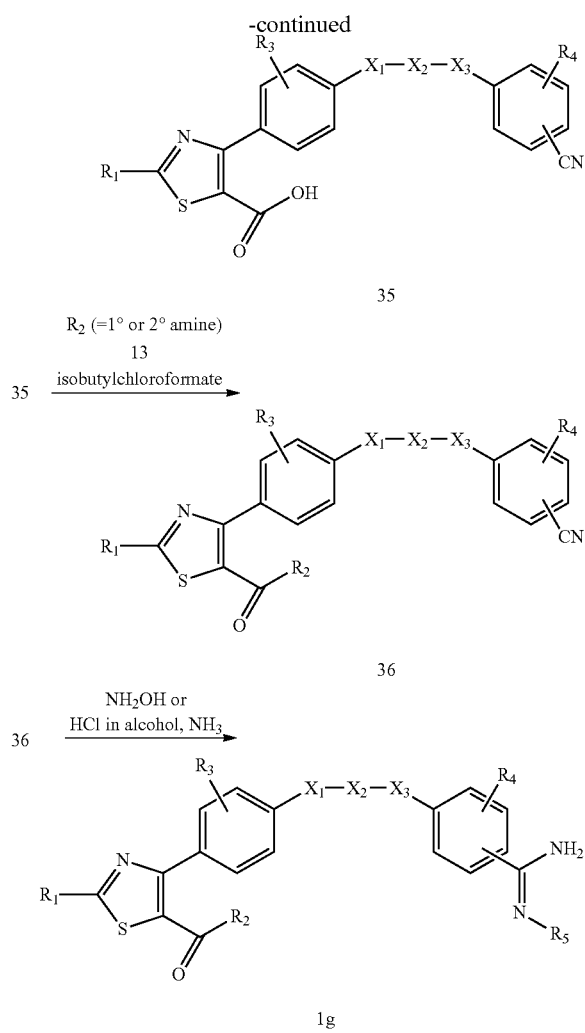

wherein $R_1$, $R_2$, $R_3$, $R_4$, $R_5$, $X_1$, $X_2$ and $X_3$ are the same as defined in the compound of the formula 1.

The method for preparing the benzamidine derivative substituted with a thiazole derivative of the present invention is specifically described as below:

In Reaction Schemes 1 to 7, the compound (2), the compound (5), the acid chloride (7), the compound (4), the compound (6), the compound (8), the amine (13), the thioamide (10), the thiourea (15), the halide compounds (19, 21, 27 and 29), and the substituted compound (23) of which both terminals are substituted with halogen are commercially available, or can be simply synthesized with a method known in the art for use.

Reaction Scheme 1 is illustrated by using specific compounds as shown below.

In the step 1), 4-cyanophenol (2; $R_4$=H, $X_3$=O) is reacted with 1-bromo-5-chloropentane (3; Br—$X_2$—Cl: $X_2$=pentylene) in the presence of a base to prepared 4-(5-chloropentoxy)benzonitrile (4). The base to be used herein may be an inorganic base, preferably on selected from the group consisting of potassium carbonate, sodium hydroxide, and sodium hydride. The reaction is preferably carried out at a temperature in the range of 10 to 90° for 1 to 9 hours, and acetonitrile, dimethylformamide, or the like is preferably used as the reaction solvent.

In the step 2), 4-(5-chloropentoxy)benzonitrile (4) prepared in the step 1) is reacted with phenol (5; $R_3$=H, $X_1$=O) in the presence of a base to prepare a 4-(5-phenoxypentyloxy)benzonitrile derivative (6). The base to be used for preparing the compound (6) may be an inorganic base, and preferably one selected from the group consisting of potassium carbonate, sodium hydroxide, and sodium hydride. The reaction is preferably carried out at a temperature in the range of 10 to 90☐ 1 to 9 hours, and acetonitrile, dimethylformamide, or the like is preferably used as the reaction solvent.

In the step 3), 4-(5-phenoxypentyloxy)benzonitrile derivative (6) prepared in the step 2) is reacted with 4-chlorobutyryl chloride (7; n=2) in the presence of an inorganic acid to prepare a 4-{(5-[4-(4-chlorobutyryl)phenoxy]pentyloxy}benzonitrile compound (8). The acid chloride (7) to be used for preparing the compound (8) can be selected to have a suitable alkyl group for the length of the substituent. This acid chloride compound (7) to be used may be 3-bromopropionyl chloride, 3-chloropropionyl chloride, 2,3-dichloropropionyl chloride, 4-chlorobutyryl chloride, and 4-bromobutyryl chloride, which are commercially available, or can be simply synthesized with a method known in the art for use. The inorganic acid to be used herein may be aluminum chloride, and the reaction is preferably carried out at a temperature in the range of −20 to 30☐ for 2 to 24 hours. The reaction solvent is suitably dichloromethane, chloroform, or the like. The acid to be used for preparing the compound (8) may be an organic acid such as acetic acid and bromic acid, or an inorganic acid such as aluminum chloride. The reaction is preferably carried out at a temperature in the range of 60 to 100☐ for 10 to 30 hours. To increase efficiency of the reaction, an excess amount of an acid can be used as the reaction solvent.

In the step 4), the compound (8) prepared in the step 3) is reacted with a bromine compound to prepare an alpha-brominated compound (9). The reagent to be used for the reaction can be copper (II) bromide or bromine, and the reaction is preferably carried out at a temperature in the range of 20 to 80☐ for 8 to 24 hours. Ethyl acetate is used as the reaction solvent.

In the step 5), the alpha-brominated compound (9) prepared in the step 4) is reacted with a thioamide compound (10) to prepare a compound (11) having a thiazole ring. The thioamide compound (10) to be used for the reaction is a substance to introduce the substituent $R_1$ into the compound of the formula 1 and the thioamide compound (10) with a proper substituent can be selected according to the type of the substituents. The reaction temperature and time may vary according to the type of the thioamide compound (10), and the reaction is preferably carried out at a temperature in the range of 60 to 90☐ for 5 to 24 hours. Examples of the thioamide compound (10) include thioacetamide, thiopropionamide, thioisobutyramide, trimethylthioacetamide, thiohexanoamide, cyclohexancarbothioicacid amide, N-(2-amino-2-thioxoethyl)-2-methylpropanamide, piperidin-4-carbothioic acid amide, thiourea, amidinothiourea, thiobenzoamide, glycine thioamide, and 2,2-dimethyl thiopropionamide, which are available commercially or simply synthesized with a method known in the art. A single solvent of ethanol or a mixed solvent of ethanol and water is used as the reaction solvent.

In the step 6), the compound (11) having a thiazole ring prepared in the step 5) is reacted with sodium iodide to prepare a compound (12). The reaction is preferably carried out at a temperature in the range of 60 to 90☐ for 1 to 15 hours, and a single solvent such as 2-butanone, acetone, 3-pentanone, methanol, ethanol and acetonitrile, or a mixed solvent thereof with water is preferably used as the reaction solvent.

In the step 7), the compound (12) prepared in the step 6) is reacted with a primary or secondary amine compound (13) in the presence of a base to prepare a compound (14). The amide compound (13) to be used for preparing the compound (14) is a substance to introduce the substituent $R_2$ into the compound of the formula 1 and the amine compound (13) with a proper substituent can be selected according to the type of the substituents. Examples of the amine compound (13) include methylamine, dimethylamine, ethylamine, diethylamine, propylamine, isopropylamine, diisopropylamine, butylamine, dibutylamine, t-butylamine, isopropyloxypropylamine, piperidine, pyrrolidine, morpholine, pyrimidine, imidazole, N-methylpiperazine, N-methylethylamine, N,N-dimethylethylamine, dimethoxyethylamine, isobutyrylamine, dihydroxyethylamine, 2,6-dimethylmorpholine, thiomorpholine, aminoethylmorpholine, aminopropylimidazole, aminopropylmorpholine, aminoethylimidazole, cyclopentylamine, cyclopropylamine, and cyclohexylamine, which are available commercially or simply synthesized with a method known in the art. The base to be used herein may be an inorganic base, and preferably one selected from the group consisting of sodium hydroxide, and sodium hydride. The reaction is preferably carried out at a temperature in the range of −10 to 100□ for 1 to 24 hours. Further, dichloromethane, chloroform, acetonitrile, dimethylformamide, dimethylsulfoxide, or the like is preferably used as the reaction solvent.

In the step 8), the compound (14) prepared in the step 7) is reacted with an amine compound in the presence of a base to prepare a compound (1a) of the formula 1. In the case of N-hydroxy amidine ($R_5$=OH), hydroxylamine hydrochloride is reacted in the presence of a base, and the base can be selected from the group consisting of organic bases such as triethylamine, 1,8-diazabicyclo[5.4.0]undec-7-ene (DBU), diethylmethylamine ($Et_2NMe$), N-methylmorpholine, N-methylpiperidine, pyridine and 2,6-dimethylpyridine, and inorganic bases such as potassium carbonate, potassium bicarbonate, sodium hydroxide, potassium hydroxide, sodium amide, sodium hydride, sodium methoxide, and sodium ethoxide. The reaction is preferably carried out at a temperature in the range of 60 to 90□ for 1 to 15 hours. A single solvent such as methanol, ethanol and acetonitrile, or a mixed solvent thereof with water is preferably used as the reaction solvent.

In the case of amidine ($R_5$=H), methoxy imine is prepared from the reaction with a hydrochloride methanol solution at a temperature in the range of 10 to 30□ for 24 to 48 hours and then the solvent is removed under reduced pressure. The resultant is reacted with an ammonia ethanol solution at a temperature in the range of 45 to 60□ for 24 to 50 hours in a high pressure reactor to prepare amidine. Ethanol is preferably used as the reaction solvent.

Reaction Scheme 2 is illustrated in detail as below.

In the step 1), the alpha-brominated compound (9) prepared in the step 4) of Reaction Scheme 1 is reacted with a thiourea compound (15) to prepare a benzonitrile derivative (16) with a aminothiazole ring. The thiourea compound (15) to be used for the reaction is a substance to introduce the substituent $R_1$ into the compound of the formula 1, and the thiourea compound (15) with a proper alkyl group can be selected according to the type of the substituent. The reaction temperature and time may vary according to the type of the thiourea compound (15), and the compound is available commercially or simply synthesized with a method known in the art. The reaction is preferably carried out at a temperature in the range of 60 to 90□ for 5 to 24 hours. Ethanol as a single solvent or a mixed solvent of ethanol and water is used as the reaction solvent.

In the step 2), the benzonitrile derivative (16) with an aminothiazole ring prepared in the step 1) is reacted with sodium iodide to prepare a compound (17). The reaction is preferably carried out at a temperature in the range of 60 to 90□ for 1 to 15 hours, a single solvent such as 2-butanone, acetone, 3-pentanone, methanol, ethanol and acetonitrile, or a mixed solvent thereof with water is preferably used as the reaction solvent.

In the step 3), the compound (17) prepared in the step 2) is reacted with morpholine (13; $R_2$) in the presence of a base to prepare a compound (18). The amine compound (13) to be used for preparing the compound (18) is a substance to introduce the substituent $R_2$ into the compound of the formula 1, and the amine compounds (13) can be suitably selected according to the type of the substituent. Examples of this amine compound (13) to be used include methylamine, dimethylamine, ethylamine, diethylamine, propylamine, isopropylamine, diisopropylamine, butylamine, dibutylamine, t-butylamine, isopropyloxypropylamine, piperidine, pyrrolidine, morpholine, pyrimidine, imidazole, N-methylpiperazine, N-methylethylamine, N,N-dimethylethylamine, dimethoxyethylamine, isobutyrylamine, dihydroxyethylamine, 2,6-dimethylmorpholine, thiomorpholine, aminoethylmorpholine, aminopropylimidazole, aminopropylmorpholine, aminoethylimidazole, cyclopentylamine, cyclopropylamine, and cyclohexylamine, which are commercially available, or can be simply synthesized with a method well known in the art for use. The base to be used herein may be an inorganic base, and preferably one selected from the group consisting of sodium hydroxide and sodium hydride. The reaction is preferably carried out at a temperature in the range of −10 to 100□ for 1 to 24 hours. Further, dichloromethane, chloroform, acetonitrile, dimethylformamide, dimethylsulfoxide, or the like is preferably as the reaction solvent.

In the step 4), the benzonitrile derivative with an aminothiazole ring (18) prepared in the step 3) is reacted with a halide compound (19) in the presence of a base to prepare a benzonitrile derivative (20) with a thiazole ring substituted with a primary amine. The halide compound (19) is a substance to introduce the substituent $R_1$ into an amino group if the substituent $R_1$ is a primary amine in the compound of the formula 1, and the halide compound (19) with a proper substituent and a halide can be selected according to the type of the substituent. The reaction temperature and time may vary according to the type of the halide compound (19). The reaction is preferably carried out at a temperature in the range of 0 to 90□ for 5 to 24 hours. Examples of the halide compound (15) include methyl iodide, ethyl iodide, propyl bromide, 2-chloroethyl methyl ether, chloroethyl morpholine, 3-bromomethylpyridine, bromoethanol, benzyl bromide, nicotinoyl chloride, ethanesulfonyl chloride, isonicotinoyl chloride, bisdibromide ethylester, acetoxyacetylchloride, and methoxyacetylchloride, which are commercially available, or can be simply synthesized with a method well known in the art. Acetonitrile, dimethylformamide, or the like is preferably used as the reaction solvent.

In the step 5), the benzonitrile derivative (20) with a thiazole ring substituted with a primary amine prepared in the step 4) is reacted with an amine compound under the same condition and manner as in the step 8) of Reaction Scheme 1 to prepare a compound of the formula 1b.

Reaction Scheme 3 is illustrated in detail as below.

In the step 1), the compound (20) prepared in the step 4) of Reaction Scheme 2 is reacted with a halide compound (21) in the presence of a base to prepare a substituted benzonitrile (22) derivative with a thiazole ring substituted with a secondary amine. The halide compound (21) is a substance to introduce the second substituent if the substituent $R_1$ is a secondary amine in the compound of the formula 1, and the halide compound (21) with a proper substituent and a halide can be selected according to the type of the substituent. The reaction temperature and time may vary according to the type of the halide compound (21). The reaction is preferably carried out at a temperature in the range of 0 to 90☐ for 5 to 24 hours. Examples of the halide compound (21) include iodomethane, iodoethane, propyl bromide, 2-chloroethyl methyl ether, chloro ethyl morpholine, 3-bromomethylpyridine, bromoethanol, benzyl bromide, nicotinoyl chloride, ethanesulfonyl chloride, and isonicotinoyl chloride, which are commercially available, or can be simply synthesized with a method well known in the art. Acetonitrile, dimethylformamide, or the like is preferably used as the reaction solvent.

In the step 2), the benzonitrile derivative (22) with a thiazole ring substituted with a secondary amine prepared in the step 1) is reacted with an amine compound under the same condition and manner as in the step 8) of Reaction Scheme 1 to prepare a compound of the formula 1c.

Reaction Scheme 4 is illustrated in detail as below.

In the step 1), the benzonitrile derivative (20) with an aminothiazole ring prepared in the step 3) of the Reaction Scheme 2 is reacted with a compound (23) of which both terminals are substituted by halogen in the presence of a base to prepare a benzonitrile derivative (20) with a thiazole ring in which $R_1$ is substituted with $C_1$ to $C_6$ alkyl substituted with

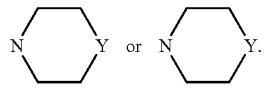

The compound (23) of which both terminals are substituted by halogen is a substance to introduce

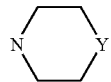

into the substituent $R_1$ in the compound of the formula 1, and the compound (23) can be suitably selected according to the type of the substituent. The reaction is preferably carried out at a temperature in the range of 0 to 90☐ for 4 to 24 hours. Examples of the compound (23) include mechlorethylamine, bisdibromide ethylester, and 1,5-dibromopentane, which are commercially available, or can be simply synthesized with a method well known in the art. Acetonitrile, dimethylformamide, or the like is preferably used as the reaction solvent.

In the step 2), the benzonitrile derivative (24) with a thiazole ring substituted with a heteroring prepared in the step 1) is reacted with an amine compound under the same condition and manner as in the step 8) of Reaction Scheme 1 to prepare a compound of the formula 1d.

Reaction Scheme 5 is illustrated in detail as below.

In the step 1), the compound (12) prepared in the step 6) of the Reaction Scheme 1 is reacted with potassium phthalimide in the presence of a base to prepare a compound (25). The base to be used herein may be an inorganic base, preferably on selected from the group consisting of sodium hydroxide, and sodium hydride. The reaction is preferably carried out at a temperature in the range of 0 to 80☐ for 1 to 24 hours. Dichloromethane, chloroform, acetonitrile, dimethylformamide, dimethylsulfoxide, or the like is preferably used as the reaction solvent.

In the step 2), the compound (25) prepared in the step 1) is reacted with hydrazine hydrate to prepare a compound (26). The reaction is preferably carried out at a temperature in the range of 20 to 90☐ or 1 to 15 hours, and a single solvent such as methanol, ethanol and acetonitrile, or a mixed solvent thereof with water is preferably used as the reaction solvent.

In the step 3), the compound (26) prepared in the step 2) is reacted with a halide compound (27) in the presence of a base to prepare a compound (14a). The halide compound (27) is a substance to introduce a substituent into the amine of the substituent $R_2$ in the compound of the formula 1, and the halide compound (27) with a proper substituent and a halide can be selected according to the type of the substituent. The reaction temperature and time may vary according to the type of the halide compound (27). The reaction is preferably carried out at a temperature in the range of 0 to 90☐ for 5 to 24 hours. Examples of the halide compound (27) include iodomethane, iodoethane, propyl bromide, 2-chloroethyl methyl ether, chloro ethyl morpholine, 3-bromomethylpyridine, bromoethanol, benzyl bromide, nicotinoyl chloride, ethanesulfonyl chloride, and isonicotinoyl chloride, which are commercially available, or can be simply synthesized with a method well known in the art. Dichloromethane, acetonitrile, dimethylformamide, or the like is preferably used as the reaction solvent.

In the step 4), the compound (14a) prepared in the step 3) is reacted with an amine compound under the same condition and manner as in the step 8) of Reaction Scheme 1 to prepare a compound of the formula 1e.

Reaction Scheme 6 is illustrated in detail as below.

In the step 1), the compound (12) prepared in the step 6) of Reaction Scheme 1 is reacted with a primary amine compound (13) in the presence of a base to prepare a compound (14b). The base to be used herein may be an inorganic base or an organic base, and preferably one selected from the group consisting of sodium hydroxide, sodium hydride and triethylamine. The reaction is preferably carried out at a temperature in the range of 0 to 80☐ for 1 to 24 hours. Dichloromethane, chloroform, acetonitrile, dimethylformamide, dimethylsulfoxide, or the like is preferably used as the reaction solvent.

In the step 2), the compound (14b) prepared in the step 1) is reacted with a halide compound (28) in the presence of a base to prepare a compound (29). The halide compound (28) is a substance to introduce a substituent into the amine of the substituent $R_2$ in the compound of the formula 1, and the halide compound (28) with a proper substituent and a halide can be selected according to the type of the substituent. The reaction temperature and time may vary according to the type of the halide compound (28). The reaction is preferably carried out at a temperature in the range of 0 to 90☐ for 5 to 24 hours. Examples of the halide compound (28) include iodomethane, iodoethane, propyl bromide, 2-chloroethyl methyl ether, chloro ethyl morpholine, 3-bromomethylpyridine, bromoethanol, benzyl bromide, nicotinoyl chloride, ethanesulfonyl chloride, and isonicotinoyl chloride, which are commercially available, or can be simply synthesized with a method well known in the art. Dichloromethane, acetonitrile, dimethylformamide, or the like is preferably used as the reaction solvent.

In the step 3), the compound (29) prepared in the step 2) is reacted with an amine compound under the same condition and manner as in the step 8) of Reaction Scheme 1 to prepare a compound of the formula 1f.

Reaction Scheme 7 is illustrated in detail as below.

In the step 1), the compound (4) prepared in the step 1) of Reaction Scheme 1 is reacted with 4-hydroxyacetophenone in the presence of a base to prepare a compound (31). The base to be used herein may be an inorganic base and preferably one selected from the group consisting of sodium hydroxide and sodium hydride. The reaction is preferably carried out at a temperature in the range of 0 to 80□ for 1 to 24 hours. Dichloromethane, chloroform, acetonitrile, dimethylformamide, dimethylsulfoxide, or the like is preferably used as the reaction solvent.

In the step 2), the compound (31) prepared in the step 1) is reacted with diethyl carbonate in the presence of a base to prepare a compound (32). The reaction is preferably carried out at a temperature in the range of 0 to 90□ for 1 to 15 hours. Dichloromethane, chloroform, acetonitrile, dimethylformamide, dimethylsulfoxide, or the like is preferably used as the reaction solvent.

In the step 3), the compound (32) prepared in the step 2) is reacted with a bromine compound to prepare an alpha-brominated compound (33). The reagent to be used for the reaction can be copper (II) bromide or bromine, and the reaction is preferably carried out at a temperature in the range of 20 to 80□ for 8 to 24 hours. Ethyl acetate is used as the reaction solvent.

In the step 4), the compound (33) prepared in the step 3) is reacted with a thioamide compound (10) to prepare a compound (34) having a thiazole ring. The thioamide compound (10) to be used for the reaction is a substance to introduce the substituent $R_1$ into the compound of the formula 1 and the thioamide compound (10) with a proper substituent can be selected according to the type of the substituents. The reaction temperature and time may vary according to the type of the thioamide compound (10), and the reaction is preferably carried out at a temperature in the range of 60 to 90□ for 5 to 24 hours. Examples of the thioamide compound (10) include thioacetamide, thiopropionamide, thioisobutyramide, trimethylthioacetamide, thiohexanoamide, cyclohexancarbothioicacid amide, N-(2-amino-2-thioxoethyl)-2-methylpropanamide, piperidin-4-carbothioic acid amide, thiourea, amidinothiourea, thiobenzamide, glycine thioamide, and 2,2-dimethyl thiopropionamide, which are available commercially or simply synthesized with a method known in the art. A single solvent of ethanol or a mixed solvent of ethanol and water is used as the reaction solvent.

In the step 5), the compound (34) prepared in the step 4) is reacted in the presence of a base to prepare an acid compound (35). The base to be used for the reaction can be sodium hydroxide, lithium hydroxide, potassium hydroxide, or the like, and the reaction is preferably carried out at a temperature in the range of 0 to 100□ for 1 to 24 hours. A single solvent such as ethanol, methanol and water, or a mixed solvent of ethanol and water is used as the reaction solvent.

In the step 6), the compound (35) prepared in the step 5) is reacted with alkylchloroformate and methylamine ($R_2$) to prepare a benzonitrile derivative (36). The amine compound to be used for preparing the benzonitrile derivative (36) is a substance to introduce the substituent $R_2$ into the compound of the formula 1 and the amine compound (13) can be suitably selected according to the type of the substituents. Examples of the amine compound (13) include methylamine, dimethylamine, ethylamine, diethylamine, propylamine, isopropylamine, diisopropylamine, butylamine, dibutylamine, t-butylamine, isopropyloxypropylamine, piperidine, pyrrolidine, morpholine, pyrimidine, imidazole, N-methylpiperazine, N-methylethylamine, N,N-dimethylethylamine, dimethoxyethylamine, isobutyrylamine, dihydroxyethylamine, 2,6-dimethylmorpholine, thiomorpholine, aminoethylmorpholine, aminopropylimidazole, aminopropylmorpholine, aminoethylimidazole, cyclopentylamine, cyclopropylamine, and cyclohexylamine, which are available commercially or simply synthesized with a method known in the art. The alkyl in alkyl chloroformate to be used herein may be methyl, ethyl, n-propyl, i-butyl, n-butyl, or the like. The reaction is preferably carried out at a temperature in the range of 0 to 100□ or 1 to 24 hours. Further, dichloromethane, chloroform, acetonitrile, dimethylformamide, dimethylsulfoxide, or the like is preferably used as the reaction solvent.

In the step 7), the compound (36) prepared in the step 6) is reacted with an amine compound under the same condition and manner as in the step 8) of Reaction Scheme 1 to prepare a compound of the formula 1g.

In another aspect, the present invention relates to a pharmaceutical composition for the prevention and treatment of osteoporosis, comprising the compound of the formula 1 or a pharmaceutically acceptable salt thereof.

The term "osteoporosis" as used herein means the state that minerals and substrates for forming the bone are reduced abnormally in large amounts, even without any defect in the structure of the remaining bone, so that many pores are generated in the bone, making it like sponge and more likely to fracture. This may be referred to as "osteopenia". In specific examples, the benzamidine derivative of the formula 1 of the present invention suppresses the differentiation of osteoclast at a low concentration, and remarkably increases the bone mass. Thus, the benzamidine derivative of the present invention can be advantageously used for the prevention and treatment of osteoporosis.

The composition of the present invention may comprise one or more effective ingredients which are equivalent or similar in function to the benzamidine derivative, in addition to the benzamidine derivative or a pharmaceutically acceptable salt thereof.

The composition of the present invention which further comprises one or more pharmaceutically acceptable carriers in addition to the above-described ingredients can be prepared. The pharmaceutically acceptable carrier can be saline, sterilized water, a Ringer's solution, buffered saline, a dextrose solution, a maltodextrin solution, glycerol, ethanol, and a combination thereof, and may be, if necessary, further supplemented with other typical additives such as an antioxidant, a buffer and a static agent. In combination with a diluent, a dispersant, a surfactant, a binder, and a lubricant, the composition of the present invention may also be formulated into injectable dosage forms, such as an aqueous solution, a suspension, and an emulsion, pills, capsules, granules, or tablets. Moreover, depending on the kind of the ingredient or the disease, the formulation may be preferably prepared using a method known in the art or disclosed in Remington's Pharmaceutical Science (latest version), Mack Publishing Company, Easton Pa.

The composition of the present invention may be administered orally or parenterally (e.g., intravenously, subcutaneously, intra-abdominally, or topically). The dosage varies depending on the body weight, the age, the gender, the health state, the diet, the administration time period, the administration route, the excretion rate, and the disease severity of a patient. The benzamidine derivative is administered once or several times at a daily dose of approximately 10 to 1,000 mg/kg, and preferably at a daily dose of approximately 50 to 500 mg/kg.

For the prevention and treatment of osteoporosis, the composition of the present invention can be used alone or in combination with surgery, hormone therapy, chemical therapy, and use of a biological response controller.

[Mode for Invention]

A better understanding of the present invention may be obtained through the following preferable Examples and Experimental Examples, which are set forth to illustrate, but are not to be construed as the limit of the present invention.

PREPARATIVE EXAMPLE 1

Preparation of Compound (14) in Reaction Scheme 1

1-1: 4-(5-Chloropentoxy)-benzonitrile (4)

3.0 g (25.2 mmol) of 4-cyanophenol and 3.67 g (27 mmol) of potassium carbonate were sequentially added to 80 ml of acetonitrile, and then 4.67 g (25.2 mmol) of 1-bromo-5-chloropentane was added thereto. Subsequently, the mixture was refluxed for 7 hrs while maintaining the temperature at 80 to 82°, and then cooled to room temperature after stopping heating. The reaction solution was diluted with ethyl acetate, and the organic layer was washed with purified water, and then dried over anhydrous magnesium sulfate. The solvent was distilled off under reduced pressure, and the residue was recrystallized from methanol, and then washed with methanol at −10□. The resultant was dried under reduced pressure to obtain 5.09 g (yield: 90.3%) of a title compound (4).

$^1$H-NMR (CDCl$_3$) (ppm) 1.64 (m, 2H), 1.82 (m, 4H), 3.57 (t, 2H), 4.01 (t, 2H), 6.93 (d, 2H), 7.57 (d, 2H).

1-2: 4-(5-Phenoxy-pentyloxy)-benzonitrile (6)

100 g (1.1 mol) of phenol was added to and dissolved in 1 L of N,N-dimethylformamide, and 51 g (1.3 mol) of sodium hydroxide was slowly added to the solution. The mixture was warmed to 50□, and then stirred for 1 hr. 246 g (1.1 mol) of the 4-(5-chloropentoxy)-benzonitrile compound (4) obtained in Preparative Example 1-1 was added thereto at the same temperature, and the mixture was warmed to 70□, and then stirred for 4 hrs. The reaction solution was cooled to room temperature, and diluted with ethyl acetate, and the organic layer was washed with water and a sodium chloride solution. The organic layer was dried over anhydrous magnesium sulfate, recrystallized from methanol, and dried under reduced pressure to obtain 235 g (yield: 76%) of a title compound (6).

$^1$H-NMR (DMSO-d$_6$) (ppm) 1.56 (m, 2H), 1.78 (m, 4H), 3.97~4.08 (m, 4H), 6.87~6.92 (m, 3H), 7.11 (m, 2H), 7.27 (m, 2H), 7.76 (m, 2H).

1-3: 4-{5-[4-(4-Chlorobutyryl)phenoxy] pentyloxy}benzonitrile (8)

1.4 L of dichloromethane was cooled to 0□, and 140 g (1.04 mol) of aluminum chloride and 76.2 ml (0.68 mol) of 4-chlorobutyryl chloride were sequentially slowly added thereto. The mixture was stirred for 30 min. 191.3 g of (0.68 mol) of 4-(5-phenoxy-pentyloxy)-benzonitrile compound (6) obtained in Preparative Example 1-2 was dissolved in 600 ml of dichloromethane, and the solution was slowly added dropwise to the reaction solution, and then the mixture was stirred for 4 hrs at room temperature. The mixture was cooled to 0□, and then 1 L of water was added dropwise thereto under stirring. The organic layer was washed with a saturated aqueous solution of sodium bicarbonate and a sodium chloride solution, and dried over anhydrous magnesium sulfate, and the solvent was distilled off under reduced pressure. The residue was recrystallized from methanol, and dried under reduced pressure to obtain 240 g (yield: 91%) of a title compound (8).

$^1$H-NMR (DMSO-d$_6$) (ppm) 1.66~1.90 (m, 8H), 3.39 (t, 2H), 3.90 (t, 2H), 4.03 (m, 4H), 6.82 (m, 2H), 7.56 (d, 2H), 7.92 (d, 2H).

1-4: 4-{5-[4-(2-Bromo-4-chlorobutyryl)phenoxy] pentyloxy}-benzonitrile (9)

40 g (0.1 mol) of 4-{5-[4-(4-chlorobutyryl)phenoxy] pentyloxy}benzonitrile compound (8) obtained in Preparative Example 1-3 was dissolved in 400 ml of ethyl acetate, and 47 g (0.2 mol) of copper (II) bromide was added thereto. The mixture was refluxed at a temperature of 70□ for 8 hrs. The reaction solution was cooled to room temperature, and then the salts generated during the reaction were filtered off, and the ethyl acetate layer was washed with a sodium bicarbonate solution and a sodium chloride solution. The organic layer was dried over magnesium sulfate, and then dried under reduced pressure to obtain 47 g (yield: 98%) of a title compound (9).

$^1$H-NMR (CDCl$_3$) (ppm) 1.68 (m, 2H), 1.88 (m, 4H), 2.54 (m, 2H), 3.80 (m, 2H), 4.04 (m, 4H), 5.43 (m, 1H), 6.94 (m, 4H), 7.56 (d, 2H), 7.99 (d, 2H)

1-5: 4-(5-{4-[5-(2-Chloroethyl)-2-methyl-thiazol-4-yl]phenoxy}pentyloxy)-benzonitrile (11)

48 g (0.1 mol) of 4-{5-[4-(2-bromo-4-chlorobutyryl)phenoxy]pentyloxy}-benzonitrile compound (9) obtained in Preparative Example 1-4 was added to 400 ml of ethanol, 16 g (0.21 mol) of thioacetamide was added thereto. The mixture was refluxed at a temperature of 80□ for 12 hrs. The reaction solution was cooled to room temperature, diluted with ethyl acetate, and then washed with a sodium bicarbonate solution and a sodium chloride solution. The organic layer was dried over magnesium sulfate, and then dried under reduced pressure to obtain 45 g (yield: 97%) of a title compound (11).

$^1$H-NMR (DMSO-d$_6$) (ppm) 1.58 (m, 2H), 1.80 (m, 4H), 2.63 (s, 3H), 3.29 (t, 2H), 3.84 (t, 2H), 4.03~4.09 (m, 4H), 7.01 (d, 2H), 7.10 (d, 2H), 7.49 (d, 2H), 7.75 (d, 2H).

1-6: 4-(5-{4-[5-(2-Iodoethyl)-2-methyl-thiazol-4-yl] phenoxy}pentyloxy)-benzonitrile (12)

45.4 g (0.103 mol) of 4-(5-{4-[5-(2-chloroethyl)-2-methyl-thiazol-4-yl]phenoxy}pentyloxy)-benzonitrile compound (11) obtained in Preparative Example 1-5 and 77 g (0.515 mol) of sodium iodide were sequentially added to 450 ml of 2-butanone, and the mixture was refluxed at 80□ for 12 hrs. The reaction solution was cooled to room temperature, diluted with ethyl acetate, and washed with a sodium bicarbonate solution and a sodium chloride solution. The organic layer was dried over anhydrous magnesium sulfate, the solvent was removed therefrom, and the residue was dried under reduced pressure to obtain 47.6 g (yield: 87%) of a title compound (12).

$^1$H-NMR (DMSO-d$_6$) (ppm) 1.58 (m, 2H), 1.80 (m, 4H), 2.63 (s, 3H), 3.39~3.43 (m, 4H), 4.03~4.10 (m, 4H), 7.01 (d, 2H), 7.11 (d, 2H), 7.49 (d, 2H), 7.76 (d, 2H).

1-7: 4-(5-{4-[5-(2-Isobutylaminoethyl)-2-methyl-thiazol-4-yl]phenoxy}pentyloxy)-benzonitrile (14)

550 mg (1.03 mmol) of 4-(5-{4-[5-(2-iodoethyl)-2-methyl-thiazol-4-yl]phenoxy}pentyloxy)-benzonitrile compound (12) obtained in Preparative Example 1-6 and 0.42 ml (4.13 mmol) of isobutylamine were added to 20 ml of acetonitrile, and the mixture was stirred at room temperature for 8 hrs. The reaction solution was diluted with dichloromethane, and washed with purified water and sodium chloride solution. The organic layer was dried over anhydrous magnesium sulfate, the solvent was removed therefrom, and the residue was recrystallized from dichloromethane and ethyl ether, and dried under reduced pressure to obtain 230 mg (yield: 47%) of a title compound (14).

$^1$H-NMR (DMSO-$d_6$) (ppm) 0.92 (d, 6H), 1.59 (m, 2H), 1.79~1.83 (m, 5H), 2.64 (s, 3H), 2.73 (d, 2H), 3.09 (m, 2H), 3.21 (m, 2H), 4.04~4.10 (m, 4H), 7.02 (d, 2H), 7.10 (d, 2H), 7.52 (d, 2H), 7.76 (d, 2H).

PREPARATIVE EXAMPLE 2

Preparation of Compound (20) in Reaction Scheme 2

2-1: 4-(5-{4-[2-Amino-5-(2-chloroethyl)thiazol-4-yl]phenoxy}pentyloxy)benzonitrile (16)

16.9 g (36.3 mmol) of 4-{5-[4-(2-bromo-4-chlorobutyryl)phenoxy]pentyloxy}-benzonitrile compound (9) of Preparative Example 1-4 and 5.53 g (72.6 mmol) of thiourea were added to 100 ml of ethanol, and the mixture was refluxed at 80□ for 12 hrs. The reaction solution was cooled to room temperature, added with purified water for recrystallization, and filtered under reduced pressure to obtain 3.3 g (yield: 21%) of a title compound (16).

$^1$H-NMR (DMSO-$d_6$) (ppm) 1.57 (m, 2H), 1.79 (m, 4H), 3.36 (m, 2H), 3.78 (m, 2H), 4.01 (m, 4H), 6.90 (m, 4H), 7.40 (d, 2H), 7.58 (d, 2H).

2-2: 4-(5-{4-[2-Amino-5-(2-iodoethyl)thiazol-4-yl]phenoxy}pentyloxy)benzonitrile (17)

3.3 g (7.47 mmol) of 4-(5-{4-[2-amino-5-(2-chloroethyl)thiazol-4-yl]phenoxy}pentyloxy)benzonitrile compound (16) obtained in Preparative Example 2-1 and sodium iodide 4.47 g (29.9 mmol) were sequentially added to 100 ml of 2-butanone, and the mixture was refluxed at 80□ for 12 hrs. The reaction solution was cooled to room temperature, and diluted with ethyl acetate, and washed with a sodium bicarbonate solution and a sodium chloride solution. The organic layer was dried over magnesium sulfate, the solvent was removed therefrom, and the residue was dried under reduced pressure to obtain 2.36 g (yield: 59%) of a title compound (17).

$^1$H-NMR (DMSO-$d_6$) (ppm) 1.57 (m, 2H), 1.79 (m, 4H), 3.36 (m, 2H), 3.89 (m, 2H), 4.02 (m, 4H), 6.90 (m, 4H), 7.40 (d, 2H), 7.58 (d, 2H).

2-3: 4-(5-{4-[2-Amino-5-(2-morpholinoethyl)thiazol-4-yl]phenoxy}pentyloxy)benzonitrile (18)

2.36 g (4.42 mmol) of 4-(5-{4-[2-amino-5-(2-iodoethyl)thiazol-4-yl]phenoxy}pentyloxy)benzonitrile compound (17) obtained in Preparative Example 2-2 and 1.23 ml (8.85 mmol) of triethylamine, and 0.39 ml (4.42 mmol) of morpholine were added to 50 ml of acetonitrile, and the mixture was refluxed at 80□ for 12 hrs. The reaction solution was cooled to room temperature, diluted with dichloromethane, and washed with purified water and a sodium chloride solution. The organic layer was dried over anhydrous magnesium sulfate, the solvent was removed therefrom, and the residue was separated by column chromatography using a mixed solvent of hexane:ethyl acetate:methanol=7:5:1, and dried under reduced pressure to obtain 890 mg (yield: 40%) of a title compound (18).

$^1$H-NMR (DMSO-$d_6$) (ppm) 1.58 (m, 2H), 1.80 (m, 4H), 2.39 (m, 4H), 2.50 (m, 2H), 2.86 (m, 2H), 3.58 (m, 4H), 4.01 (m, 4H), 6.91 (m, 4H), 7.43 (m, 2H), 7.60 (m, 2H).

2-4: 4-(5-{4-[2-Methylamino-5-(2-morpholinoethyl)thiazol-4-yl]phenoxy}pentyloxy)benzonitrile (20)

770 mg (1.6 mmol) of 4-(5-{4-[2-amino-5-(2-morpholinoethyl)thiazol-4-yl]phenoxy}pentyloxy)benzonitrile compound (18) obtained in Preparative Example 2-3 and 130 mg (3.3 mmol) of sodium hydride were added to 50 ml of N,N-dimethylformamide, and the mixture was stirred at room temperature for 30 min. To the reaction solution, 0.25 ml (4.1 mmol) of methyl iodide was added at the same temperature, and the mixture was stirred for 30 min. The mixture was diluted with ethyl acetate, and washed with purified water. The organic layer was dried over anhydrous magnesium sulfate, the solvent was removed therefrom, and the residue was separated by column chromatography using a mixed solvent of hexane:ethyl acetate:methanol=15:5:1, and dried under reduced pressure to obtain 410 mg (yield: 20%) of a title compound (20).

$^1$H-NMR (DMSO-$d_6$) (ppm) 1.58 (m, 2H), 1.80 (m, 4H), 2.38 (m, 4H), 2.51 (m, 2H), 2.81 (s, 3H), 2.85 (m, 2H), 3.59 (m, 4H), 4.01 (m, 4H), 6.91 (m, 4H), 7.43 (m, 2H), 7.60 (m, 2H).

PREPARATIVE EXAMPLE 3

Preparation of Compound (22) in Reaction Scheme 3

3-1: 4-(5-{4-[2-N,N-dimethylamino-5-(2-morpholinoethyl)thiazol-4-yl]phenoxy}pentyloxy)benzonitrile (22)

920 mg (1.8 mmol) of 4-(5-{4-[2-methylamino-5-(2-morpholinoethyl)thiazol-4-yl]phenoxy}pentyloxy)benzonitrile compound (20) obtained in Preparative Example 2-4 and 110 mg (2.7 mmol) of sodium hydride were added to 50 ml of N,N-dimethylformamide, and then the mixture was stirred at room temperature for 30 min. To the reaction solution, 0.12 ml (2.0 mmol) of methyl iodide was added at the same temperature, and the mixture was stirred for 30 min. The mixture was diluted with ethyl acetate, and washed with purified water. The organic layer was dried over anhydrous magnesium sulfate, the solvent was removed therefrom, and the residue was separated by column chromatography using a mixed solvent of hexane:ethyl acetate:methanol=15:5:1, and dried under reduced pressure to obtain 592 mg (yield: 63%) of a title compound (22).

$^1$H-NMR (DMSO-$d_6$) (ppm) 1.57 (m, 2H), 1.79 (m, 4H), 2.38 (m, 4H), 2.49 (m, 2H), 2.85 (m, 2H), 2.99 (s, 6H), 3.58 (m, 4H), 4.00 (m, 4H), 6.93 (m, 4H), 7.44 (d, 2H), 7.59 (d, 2H).

PREPARATIVE EXAMPLE 4

Preparation of Compound (24) in Reaction Scheme 4

4-1: 4-(5-{4-[2-Morpholin-4-yl-5-(2-morpholin-4-yl-ethyl)thiazol-4-yl]phenoxy}pentyloxy)benzonitrile (24)

770 mg (1.6 mmol) of 4-(5-{4-[2-amino-5-(2-morpholinoethyl)thiazol-4-yl]phenoxy}pentyloxy)benzonitrile compound (18) obtained in Preparative Example 2-3 and 130 mg (3.3 mmol) of sodium hydride were added to 50 ml of N,N-dimethylformamide, and then the mixture was stirred at room temperature for 30 min. To the reaction solution, 0.22 ml (1.72 mmol) of dibromoether was added at the same temperature, and the mixture was stirred for 3 hrs. The mixture was diluted with ethyl acetate, and washed with purified water. The organic layer was dried over anhydrous magnesium sulfate, the solvent was removed therefrom, and the residue was separated by column chromatography using a mixed solvent of hexane:ethyl acetate=1:2, and dried under reduced pressure to obtain 80 mg (yield: 9%) of a title compound (24).

$^1$H-NMR (DMSO-d$_6$) (ppm) 1.57 (m, 2H), 1.79 (m, 4H), 2.38 (m, 4H), 2.49 (m, 2H), 2.85 (m, 2H), 2.99 (s, 6H), 3.58 (m, 4H), 4.00 (m, 4H), 6.93 (m, 4H), 7.44 (d, 2H), 7.59 (d, 2H).

PREPARATIVE EXAMPLE 5

Preparation of Compound (14a) in Reaction Scheme 5

5-1: 4-[5-(4-{5-[2-(1,3-Dioxo-1,3-dihydro-isoindol-2-yl)-ethyl]-2-methyl-thiazol-4-yl}phenoxy)pentyloxy]-benzonitrile (25)

2.74 g (5.16 mmol) of 4-(5-{4-[5-(2-iodoethyl)-2-methyl-thiazol-4-yl]phenoxy}pentyloxy)-benzonitrile compound (12) obtained in Preparative Example 1-6 and 3.82 g (20.6 mmol) of potassium phthalimide were added to 30 ml of dimethylsulfoxide, and then the mixture was stirred at room temperature for 12 hrs. The mixture was diluted with ethyl acetate, and washed with purified water. The organic layer was dried over anhydrous magnesium sulfate, the solvent was removed therefrom, and the residue was separated by column chromatography using a mixed solvent of hexane:ethyl acetate=2:1, and dried under reduced pressure to obtain 1.0 g (yield: 35%) of a title compound (25).

$^1$H-NMR (DMSO-d$_6$) (ppm) 1.59 (m, 6H), 1.80 (m, 4H), 2.60 (s, 3H), 3.25 (m, 2H), 3.74 (m, 2H), 3.95~4.11 (m, 4H), 6.78 (d, 2H), 7.12 (d, 2H), 7.37 (d, 2H), 7.77 (m, 6H).

5-2: 4-(5-{4-[5-(2-Aminoethyl)-2-methyl-thiazol-4-yl]phenoxy}pentyloxy)-benzonitrile (26)

800 mg (1.45 mmol) of 4-[5-(4-{5-[2-(1,3-dioxo-1,3-dihydro-isoindol-2-yl)-ethyl]-2-methyl-thiazol-4-yl}phenoxy)pentyloxy]-benzonitrile compound (25) obtained in Preparative Example 5-1 and 290 mg (5.80 mmol) of hydrazine hydrate were added to 10 ml of methanol, and the mixture was refluxed at 65□ for 12 hrs. The mixture was diluted with dichloromethane, and washed with purified water. The organic layer was dried over anhydrous magnesium sulfate, the solvent was removed therefrom, and the residue was dried under reduced pressure to obtain 300 mg (yield: 49%) of a title compound (26).

$^1$H-NMR (DMSO-d$_6$) (ppm) 1.59 (m, 2H), 1.80 (m, 4H), 2.61 (s, 3H), 2.79 (m, 2H), 2.90 (m, 2H), 4.02~4.11 (m, 4H), 6.98 (d, 2H), 7.10 (d, 2H), 7.51 (d, 2H), 7.76 (d, 2H).

5-3: 4-(5-{4-[5-(2-Isobutyrylaminoethyl)-2-methyl-thiazol-4-yl]phenoxy}pentyloxy)-benzonitrile (14a)

300 mg (0.71 mmol) of 4-(5-{4-[5-(2-aminoethyl)-2-methyl-thiazol-4-yl]phenoxy}pentyloxy)-benzonitrile compound (26) obtained in Preparative Example 5-2 was added to 10 ml of dichloromethane, and the mixture was cooled to 0□, to which 0.08 ml (0.78 mmol) of isobutyryl chloride was then added. To the mixture, 0.11 ml (0.78 mmol) of triethylamine was added, and the mixture was stirred at room temperature for 2 hrs. The reaction solution was diluted with dichloromethane, and washed with purified water. The organic layer was dried over anhydrous magnesium sulfate, the solvent was removed therefrom, and the residue was dried under reduced pressure to obtain 150 mg (yield: 43%) of a title compound (14a).

$^1$H-NMR (DMSO-d$_6$) (ppm) 0.97 (d, 6H), 1.58 (m, 2H), 1.83 (m, 4H), 2.30 (m, 1H), 2.62 (s, 3H), 2.96 (m, 2H), 3.25 (m, 2H), 4.03~4.10 (m, 4H), 6.98 (d, 2H), 7.11 (d, 2H), 7.51 (d, 2H), 7.76 (d, 2H), 7.97 (m, 1H).

PREPARATIVE EXAMPLE 6

Preparation of Compound (29) in Reaction Scheme 6

6-1: 4-(5-{4-[5-(2-Isobutylaminoethyl)-2-methyl-thiazol-4-yl]phenoxy}pentyloxy)-benzonitrile (14b)

550 mg (1.03 mmol) of 4-(5-{4-[5-(2-iodoethyl)-2-methyl-thiazol-4-yl]phenoxy}pentyloxy)-benzonitrile compound (12) obtained in Preparative Example 1-6 and 0.42 ml (4.13 mmol) of isobutylamine were added to 20 ml of acetonitrile, and the mixture was stirred at room temperature for 8 hrs. The reaction solution was diluted with dichloromethane, and washed with purified water and a sodium chloride solution. The organic layer was dried over anhydrous magnesium sulfate, the solvent was removed therefrom, and the residue was recrystallized from dichloromethane and ethyl ether, and dried under reduced pressure to obtain 230 mg (yield: 47%) of a title compound (14b).

$^1$H-NMR (DMSO-d$_6$) (ppm) 0.92 (d, 6H), 1.59 (m, 2H), 1.79~1.83 (m, 5H), 2.64 (s, 3H), 2.73 (d, 2H), 3.09 (m, 2H), 3.21 (m, 2H), 4.04~4.10 (m, 4H), 7.02 (d, 2H), 7.10 (d, 2H), 7.52 (d, 2H), 7.76 (d, 2H).

6-2: 4-{5-[4-(5-{2-[Isobutyl-(pyridine-3-carbonyl)-amino]-ethyl}-2-methyl-thiazol-4-yl)phenoxy]pentyloxy}-benzonitrile (29)

310 mg (0.65 mmol) of 4-(5-{4-[5-(2-isobutylaminoethyl)-2-methyl-thiazol-4-yl]phenoxy}pentyloxy)-benzonitrile compound (14b) obtained in Preparative Example 6-1 was added to 20 ml of dimethylformamide, and the mixture was cooled to 0°. To the mixture, 139 mg (0.78 mmol) of nicotinoyl chloride and 65 mg (1.62 mmol) of sodium hydride were added, and the mixture was stirred at room temperature 8 hrs. The reaction solution was diluted with ethyl acetate, and washed with purified water. The organic layer was dried over anhydrous magnesium sulfate, the solvent was removed therefrom, and the residue was purified by column chromatography using ethyl acetate:n-hexane:methanol=7:5:1 as an eluent to obtain 200 mg (yield: 53%) of a title compound (29).

$^1$H-NMR (DMSO-d$_6$) (ppm) 0.62 (d, 3H), 0.86 (d, 3H), 1.22 (s, 2H), 1.57 (m, 2H), 1.79 (m, 5H), 2.56 (s, 2H), 2.66 (s, 1H), 2.98 (m, 2H), 3.15 (m, 1H), 3.21 (m, 1H), 3.42 (m, 1H), 3.63 (m, 1H), 4.02 (t, 2H), 4.09 (m, 2H), 6.91 (d, 2H), 6.98 (d, 2H), 7.09 (d, 4H), 7.23 (d, 2H), 8.59 (d, 2H).

PREPARATIVE EXAMPLE 7

Preparation of Compound (36) in Reaction Scheme 7

7-1: 4-[5-(Acetyl-phenoxy)-pentyloxy]-benzonitrile (31)

20 g (147 mmol) of 4-hydroxyacetophenone was dissolved in 200 ml of dimethylformamide, and 33 g (147 mmol) of the 4-(5-chloropentoxy)-benzonitrile compound (4) obtained in Preparative Example 1-1 and 7 g (176 mmol) of sodium hydroxide were added thereto. The mixture was stirred at 100□ for 6 hrs. The mixture was cooled to room temperature, diluted with ethyl acetate, and washed with water. The mixture was dried over anhydrous magnesium sulfate, the solvent was dried under reduced pressure, and the residue was recrystallized from 50 ml of methanol to obtain 33 g (yield: 60%) of a title compound (31).

$^1$H-NMR (DMSO-$d_6$) (ppm) 1.56 (m, 2H), 1.80 (m, 4H), 2.51 (s, 3H), 4.08 (m, 4H), 7.02 (d, 2H), 7.09 (d, 2H), 7.75 (d, 2H), 7.92 (d, 2H).

7-2: 4-{5-[4-(2-Ethoxycarbonyl-acetyl)phenoxy]pentyloxy]-benzonitrile (32)

5 g (15.46 mmol) of 4-[5-(acetyl-phenoxy)-pentyloxy]-benzonitrile compound (31) obtained in Preparative Example 7-1 was dissolved in 30 ml of dimethylformamide and 30 ml of tetrahydrofuran (THF), and 1.24 g (77.31 mmol) of sodium hydride was added thereto. The mixture was stirred at room temperature for 30 min. 9.4 ml of diethyl carbonate was added thereto, and the mixture was stirred at 80□ for 6 hr, and then cooled to room temperature. The reaction solution was diluted with ethyl acetate, washed with water, and dried over anhydrous magnesium sulfate, and the solvent was removed therefrom. The residue was purified by column chromatography using ethyl acetate:n-hexane=1:2 as an eluent to obtain 2.63 g (yield: 43%) of a title compound (32).

$^1$H-NMR (DMSO-$d_6$) (ppm) 1.16 (t, 3H), 1.57 (m, 2H), 1.81 (m, 4H), 4.09~4.11 (m, 8H), 7.07 (d, 2H), 7.11 (d, 2H), 7.75 (d, 2H), 7.91 (d, 2H).

7-3: 2-bromo-3-{4-[5-(4-cyano-phenoxy)-pentyloxy]-phenyl}-3-oxo-propionic acid ethyl ester (33)

12.12 g (37.5 mmol) of 4-{5-[4-(2-ethoxycarbonyl-acetyl)phenoxy]pentyloxy}-benzonitrile compound (32) obtained in Preparative Example 7-2 was dissolved in 200 ml of ethyl acetate, and 17 g (75 mmol) of copper (II) bromide was added thereto. The mixture was refluxed at 70□ for 8 hrs. The reaction solution was cooled to room temperature, and the salts generated during the reaction were filtered off. The ethyl acetate layer was washed with a sodium bicarbonate solution and a sodium chloride solution. The organic layer was dried over magnesium sulfate, the solvent was removed therefrom, and the residue was recrystallized from 100 ml of methanol to obtain 10 g (yield: 66%) of a title compound (33).

$^1$H-NMR (DMSO-$d_6$) (ppm) 1.18 (t, 3H), 1.59 (m, 2H), 1.82 (m, 4H), 4.56~4.61 (m, 6H), 5.46 (m, 1H), 7.07 (d, 2H), 7.11 (d, 2H), 7.75 (d, 2H), 7.91 (d, 2H).

7-4: 4-{5-[4-(5-Ethoxycarbonyl-2-methyl-thiazol-4-yl)-phenoxy]pentyloxy}-benzonitrile (34)

1.4 g (3 mmol) of 2-bromo-3-{4-[5-(4-cyano-phenoxy)-pentyloxy]-phenyl}-3-oxo-propionic acid ethyl ester compound (33) obtained in Preparative Example 7-3 was added to 50 ml of ethanol, and 450 mg (6 mmol) of thioacetamide was added thereto. The mixture was refluxed at 80□ for 12 hrs. The reaction solution was cooled to room temperature, diluted with ethyl acetate, and washed with a sodium bicarbonate solution and a sodium chloride solution. The organic layer was dried over magnesium sulfate, and then dried under reduced pressure to obtain 550 mg (yield: 41%) of a title compound (34).

$^1$H-NMR (CDCl$_3$) (ppm) 1.28 (m, 3H), 1.68 (m, 2H), 1.84 (m, 4H), 2.75 (s, 3H), 4.00 (m, 4H), 4.08 (m, 2H), 6.91 (m, 4H), 7.72 (d, 2H), 7.89 (d, 2H).

7-5: 4-{5-[4-(5-Carboxy-2-methyl-thiazol-4-yl)phenoxy]pentyloxy}-benzonitrile (35)

550 mg (1.22 mmol) of 4-{5-[4-(5-ethoxycarbonyl-2-methyl-thiazol-4-yl)-phenoxy]pentyloxy}-benzonitrile compound (34) obtained in Preparative Example 7-4 was dissolved in 20 ml of methanol and 20 ml of tetrahydrofuran (THF). 20 mg (4.88 mmol) of lithium hydroxide was added to the solution, and the mixture was stirred for 24 hrs. After removing the solvent, the residue was dissolved in 50 ml of methanol and 50 ml of water, adjusted to around pH 2 using a 1 N hydrochloride solution, and extracted with dichloromethane, and the solvent was removed therefrom to obtain 300 mg (yield: 58%) of a title compound (35).

$^1$H-NMR (DMSO-$d_6$) (ppm) 1.58 (m, 2H), 1.80 (m, 4H), 2.68 (brs, 3H), 4.05 (m, 4H), 6.98 (m, 4H), 7.70 (m, 2H), 7.83 (m, 2H).

7-6: 4-(5-{4-[5-(3-imidazol-1-yl-propylcarbamoyl)-2-methyl-thiazol-4-yl]phenoxy}pentyloxy)-benzonitrile (36)

420 mg (0.99 mmol) of 4-{5-[4-(5-carboxy-2-methyl-thiazol-4-yl)phenoxy]pentyloxy}-benzonitrile compound (35) obtained in Preparative Example 7-5 was dissolved in 20 ml of dichloromethane, and 0.26 ml (1.19 mmol) of N-methylmorpholine and 0.16 ml (1.19 mmol) of isobutyl chloroformate were added thereto. The mixture was stirred at room temperature for 30 min. 0.26 ml (2.39 mmol) of 3-aminopropylimidazole was added thereto, and the mixture was further stirred for 6 hrs. The mixture was diluted with dichloromethane, washed with water, and dried over anhydrous magnesium sulfate. The residue was separated by column chromatography using n-hexane:ethyl acetate=3:1 as an eluent to obtain 200 mg (yield: 38%) of a title compound (36).

$^1$H-NMR (DMSO-$d_6$) (ppm) 1.56 (m, 2H), 1.76 (m, 6H), 2.12 (brs, 3H), 3.35 (m, 2H), 3.90 (m, 2H), 4.01 (m, 4H), 6.80 (m, 2H), 6.94 (m, 4H), 7.25 (m, 2H), 7.56 (m, 1H), 7.75 (m, 1H), 7.84 (m, 1H).

EXAMPLE 1

Preparation of N-hydroxy-4-(5-{4-[5-(2-isobutylaminoethyl)-2-methyl-thiazol-4-yl]phenoxy}pentyloxy)-benzamidine (1)

100 mg (0.21 mmol) of 4-(5-{4-[5-(2-isobutylaminoethyl)-2-methyl-thiazol-4-yl]phenoxy}pentyloxy)-benzonitrile compound (14) obtained in Preparative Example 1-7 was added to 10 ml of ethanol, and 0.12 ml (0.84 mmol) of triethylamine and 58 mg (0.84 mmol) of hydroxylamine hydrochloride were added thereto. The mixture was refluxed at 80□ under stirring for 8 hrs. The mixture was distilled off under reduced pressure, diluted with dichloromethane, washed with water, and dried over anhydrous magnesium sulfate. After distilling the solvent off under reduced pressure, the residue was separated by column chromatography using ethyl acetate:n-hexane:methanol=5:5:1, and dried under reduced pressure to obtain the above title compound.

$^1$H-NMR (DMSO-$d_6$) (ppm) 0.86 (d, 6H), 1.60 (m, 2H), 1.80 (m, 5H), 2.60 (s, 3H), 2.73 (m, 2H), 2.94 (m, 2H), 3.34 (m, 2H), 4.01 (m, 4H), 5.72 (s, 2H), 6.93 (m, 4H), 7.57 (m, 4H), 9.45 (s, 1H)

EXAMPLE 2

Preparation of 4-(5-{4-[5-(2-isobutylaminoethyl)-2-methyl-thiazol-4-yl]phenoxy}pentyloxy)-benzamidine 100 mg (0.21 mmol) of 4-(5-{4-[5-(2-isobutylaminoethyl)-2-methyl-thiazol-4-yl]phenoxy}pentyloxy)-benzonitrile compound (14) obtained in Preparative Example 1-7 was added to 10 ml of an excessive amount of a hydrochloride/methanol solution, and the mixture was stirred at room temperature for 24 hrs. The reaction solvent was distilled off under reduced pressure. The residue was dissolved in 2 ml of ethanol, 10 ml of an ammonia/ethanol solution was added thereto. The mixture was put into a sealed tube, and reaction was carried out at 50□ for 40 hrs. The reaction solution was distilled off under reduced pressure, and the residue was purified by column chromatography using chloroform:methanol=4:1, and dried under reduced pressure to obtain the above title compound.

$^1$H-NMR (DMSO-$d_6$) (ppm) 0.85 (d, 6H), 1.58 (m, 2H), 1.79 (m, 5H), 2.59 (s, 3H), 2.71 (m, 2H), 2.92 (m, 2H), 3.32 (m, 2H), 4.01 (m, 4H), 6.93 (m, 4H), 7.57 (m, 4H), 9.09 (brs, 3H)

EXAMPLES 3 TO 44

The compounds (14) obtained in the same manner as in the Preparative Example 1-7 were prepared in the same manner as Example 1, obtaining the title compounds.

The $^1$H-NMR data of the title compounds are shown in Table 1.

TABLE 1

| Example | Chemical name | $^1$H-NMR | solvent |
|---|---|---|---|
| 3 | N-hydroxy-4-(5-{4-[2-methyl-5-(2-piperidin-1-yl-ethyl)-thiazol-4-yl]-phenoxy}-pentyloxy)-benzamidine | 1.52 (m, 2H), 1.58 (m, 6H), 1.79 (m, 4H), 2.50 (d, 2H), 2.60 (s, 3H), 2.98 (d, 2H), 3.38 (m, 4H), 4.02 (m, 4H), 5.73 (s, 2H), 6.93-7.00 (m, 4H), 7.48-7.60 (m, 4H), 9.46 (s, 1H) | DMSO-$d_6$ |
| 4 | N-hydroxy-4-[5-(4-{2-methyl-5-[2-(2-morpholin-4-yl-ethylamino)-ethyl]-thiazol-4-yl}-phenoxy)-pentyloxy]-benzamidine | 1.58-1.60 (m, 2H), 1.79-1.81 (m, 4H), 2.31-2.33 (m, 6H), 2.51-2.58 (m, 2H), 2.61 (s, 3H), 2.76 (m, 2H), 2.95 (m, 2H), 3.53 (m, 4H), 4.01-4.04 (m, 4H), 5.73 (s, 2H), 6.94-7.00 (m, 4H), 7.51 (d, 2H), 7.60 (d, 2H) | DMSO-$d_6$ |
| 5 | N-hydroxy-4-[5-(4-{5-[2-(3-imidazol-1-yl-propylamino)-ethyl]-2-methyl-thiazol-4-yl}-phenoxy)-pentyloxy]-benzamidine | 1.23 (m, 2H), 1.60 (m, 2H), 1.81 (m, 6H), 1.91 (m, 2H), 2.61 (s, 3H), 2.82 (m, 2H), 3.02 (m, 2H), 4.02 (m, 4H), 6.91-7.00 (m, 5H), 7.15 (s, 1H), 7.51 (d, 2H), 7.59 (d, 2H), 7.85 (d, 1H) | DMSO-$d_6$ |
| 6 | N-hydroxy-4-(5-{4-[5-(2-isopropylamino-ethyl)-2-methyl-thiazol-4-yl]-phenoxy}-pentyloxy)-benzamidine | 1.05 (d, 6H), 1.63 (m, 2H), 1.81-1.85 (m, 4H), 2.65 (s, 3H), 2.85-2.89 (m, 3H), 3.06-3.08 (m, 2H), 3.94-3.97 (m, 4H), 4.84 (brs, 2H), 6.34 (brs, 1H), 6.85-6.89 (m, 4H), 7.46-7.51 (m, 4H) | CDCl$_3$ |
| 7 | N-hydroxy-4-[5-(4-{5-[2-(3-isopropoxy-propylamino)-ethyl]-2-methyl-thiazol-4-yl}-phenoxy)-pentyloxy]-benzamidine | 1.05 (d, 6H), 1.65 (m, 2H), 1.79-1.84 (m, 6H), 2.64 (s, 3H), 2.77 (t, 2H), 2.91 (t, 2H), 3.15 (t, 2H), 3.40 (t, 2H), 3.50 (m, 1H), 3.94-3.97 (m, 4H), 4.93 (brs, 2H), 6.54 (brs, 1H), 6.84-6.88 (m, 4H), 7.45 (m, 4H) | CDCl$_3$ |
| 8 | N-hydroxy-4-(5-{4-[5-(2-butylamino-ethyl)-2-methyl-thiazol-4-yl]-phenoxy}-pentyloxy)-N-hydroxy-benzamidine | 0.85 (t, 3H), 1.29-1.35 (m, 6H), 1.58 (m, 2H), 1.78 (m, 4H), 2.60 (s, 3H), 2.72 (m, 2H), 2.93 (m, 2H), 4.02 (m, 4H), 5.72 (s, 2H), 6.91-6.97 (m, 4H), 7.49-7.58 (m, 4H) | DMSO-$d_6$ |
| 9 | N-hydroxy-4-(5-{4-[5-(2-imidazol-1-yl-ethyl)-2-methyl-thiazol-4-yl]-phenoxy}-pentyloxy)-benzamidine | 1.64 (m, 2H), 1.86 (m, 4H), 2.66 (s, 3H), 3.30 (t, 2H), 4.01-4.14 (m, 6H), 6.89-7.77 (m, 11H) | CDCl$_3$ |
| 10 | N-hydroxy-4-(5-{4-[5-(2-cyclohexylamino-ethyl)-2-methyl-thiazol-4-yl]-phenoxy}-pentyloxy)-benzamidine | 0.98-1.01 (m, 2H), 1.13-1.63 (m, 3H), 1.58-1.70 (m, 5H), 1.78-1.80 (m, 6H), 2.40 (m, 1H), 2.60 (s, 3H), 2.79 (m, 2H), 2.95 (m, 2H), 4.01-4.04 (m, 4H), 5.72 (s, 2H), 6.93-7.00 (m, 4H), 7.50 (d, 2H), 7.60 (d, 2H), 9.46 (s, 1H) | DMSO-$d_6$ |
| 11 | N-hydroxy-4-(5-{4-[5-(2-diethylamino-ethyl)-2-methyl-thiazol-4-yl]-phenoxy}-pentyloxy)-benzamidine | 0.93 (t, 6H), 1.59 (m, 2H), 1.79 (m, 4H), 2.49 (m, 6H), 2.59 (s, 3H), 2.92 (m, 2H), 4.02-4.04 (m, 4H), 5.72 (s, 2H), 6.93-6.70 (m, 4H), 7.48-7.82 (m, 4H), 9.46 (s, 1H) | DMSO-$d_6$ |
| 12 | N-hydroxy-4-{5-[4-(5-{2-[bis-(2-hydroxy-ethyl)-amino]-ethyl}-2-methyl-thiazol-4-yl)-phenoxy]-pentyloxy}-benzamidine | 1.59 (m, 2H), 1.79 (m, 4H), 2.55-2.59 (m, 4H), 2.60 (s, 3H), 2.75 (m, 2H), 2.95 (m, 2H), 3.41-3.43 (m, 4H), 4.01-.04 (m, 4H), 5.72 (s, 2H), 6.93-7.00 (m, 4H), 7.50 (d, 2H), 7.59 (d, 2H), 9.46 (s, 1H) | DMSO-$d_6$ |
| 13 | N-hydroxy-4-(5-{4-[5-(2-diisopropylamino-ethyl)-2-methyl-thiazol-4-yl]-phenoxy}-pentyloxy)-benzamidine | 1.29-1.42 (m, 12H), 1.65 (m, 2H), 1.84-1.89 (m, 4H), 2.71 (s, 3H), 2.93 (m, 2H), 3.52 (m, 2H), 3.64 (m, 2H) 4.00-4.04 (m, 4H), 6.92 (m, 4H), 7.45 (d, 2H), 7.78 (d, 2H) | CDCl$_3$ |
| 14 | N-hydroxy-4-[5-(4-{5-[2-(2,6-dimethyl-morpholin-4-yl)-ethyl]-2-methyl-thiazol-4-yl}-phenoxy)-pentyloxy]-benzamidine | 1.03 (d, 6H), 1.60-1.63 (m, 4H), 1.78-1.80 (m, 4H), 2.47-2.50 (m, 2H), 2.60 (s, 3H), 2.74 (m, 2H), 2.98 (m, 2H), 3.52-3.56 (m, 2H), 4.02-4.04 (m, 4H), 5.72 (s, 2H), 6.93-7.00 (m, 4H), 7.48 (d, 2H), 7.58 (d, 2H) 9.46 (s, 1H) | DMSO-$d_6$ |
| 15 | N-hydroxy-4-(5-{4-[2-methyl-5-(2-thiomorpholin-4-yl-ethyl)-thiazol-4-yl]-phenoxy}-pentyloxy)-benzamidine | 1.58 (m, 2H), 1.78-1.81 (m, 4H), 2.50-2.55 (m, 2H), 2.60 (s, 3H), 2.62 (m, 4H), 2.67 (m, 4H), 2.98 (m, 2H), 4.02-4.04 (m, 4H), 5.72 (s, 2H), | DMSO-$d_6$ |

TABLE 1-continued

| Example | Chemical name | $^1$H-NMR | solvent |
|---|---|---|---|
| | | 6.93-7.00 (m, 4H), 7.49 (d, 2H), 7.58 (d, 2H), 9.46 (s, 1H) | |
| 16 | N-hydroxy-4-(5-{4-[2-amino-5-(2-morpholin-4-yl-ethyl)-thiazol-4-yl]-phenoxy}-pentyloxy)-benzamidine | 1.59 (m, 2H), 1.79 (m, 4H), 2.91 (m, 2H), 3.34 (m, 6H), 3.63 (m, 4H), 4.03 (m, 4H), 5.76 (s, 2H), 6.93 (m, 4H), 7.43 (d, 2H), 7.59 (d, 2H), 9.53 (brs, 1H) | DMSO-$d_6$ |
| 17 | N-hydroxy-4-[5-(4-{5-[2-(2-dimethylamino-ethylamino)-ethyl]-2-methyl-thiazol-4-yl}-phenoxy)-pentyloxy]-benzamidine | 1.57 (m, 2H), 1.78 (m, 4H), 2.09 (s, 6H), 2.60 (s, 3H), 3.22-3.34 (m, 8H), 4.02 (m, 4H), 6.98 (m, 2H), 7.11 (d, 2H), 7.50 (d, 2H), 7.76 (d, 2H) | DMSO-$d_6$ |
| 18 | N-hydroxy-4-(5-{4-[2-methyl-5-(2-morpholin-4-yl-ethyl)-thiazol-4-yl]-phenoxy}-pentyloxy)-benzamidine | 1.63 (m, 2H), 1.83 (m, 4H), 2.49 (m, 4H), 2.59 (m, 2H), 2.65 (s, 3H), 3.03 (m, 2H), 3.71 (m, 4H), 3.98 (m, 4H), 4.95 (brs, 1H), 6.85-6.91 (d-d, 4H), 7.44-7.47 (d-d, 4H) | CDCl$_3$ |
| 19 | N-hydroxy-4-[5-(4-{2-methyl-5-[2-(4-methyl-piperazin-1-yl)-ethyl]-thiazol-4-yl}-phenoxy)-pentyloxy]-benzamidine | 1.64 (m, 2H), 1.83 (m, 4H), 2.29 (m, 3H), 2.58-2.63 (m, 10H), 2.64 (s, 3H), 2.99 (m, 2H), 3.96 (m, 4H), 4.85 (brs, 1H), 6.85-6.89 (d-d, 4H), 7.43-7.71 (d-d, 4H) | CDCl$_3$ |
| 20 | N-hydroxy-4-{5-[4-(5-{2-[bis-(2-methoxy-ethyl)-amino]-ethyl}-2-methyl-thiazol-4-yl)-phenoxy]-pentyloxy}-benzamidine | 1.59 (m, 2H), 1.80 (m, 4H), 2.60 (s, 3H), 2.66 (m, 4H), 2.73 (m, 2H), 2.94 (m, 2H), 3.19 (s, 6H), 3.35 (m, 4H), 4.03 (m, 4H), 5.73 (s, 2H), 6.92 (d, 2H), 6.99 (d, 2H), 7.49 (d, 2H), 7.60 (d, 2H), 9.45 (s, 1H) | DMSO-$d_6$ |
| 21 | N-hydroxy-4-(5-{4-[5-(2-tert-butylamino-ethyl)-2-methyl-thiazol-4-yl]-phenoxy}-pentyloxy)-benzamidine | 1.06 (m, 9H), 1.58 (m, 2H), 1.80 (m, 4H), 2.61 (s, 3H), 2.80 (m, 2H), 2.98 (m, 2H), 4.03 (m, 4H), 6.91-7.01 (m, 4H), 7.50-7.82 (m, 4H) | DMSO-$d_6$ |
| 22 | N-hydroxy-4-(5-{4-[5-(2-isobutylamino-ethyl)-2-methyl-thiazol-4-yl]-phenoxy}-pentyloxy)-benzamidine | 0.86 (d, 6H), 1.59 (m, 2H), 1.80 (m, 5H), 2.60 (s, 3H), 2.73 (m, 2H), 2.94 (m, 2H), 3.34 (m, 2H), 4.02 (m, 4H), 5.72 (s, 2H), 6.93 (m, 4H), 7.49-7.60 (m, 4H), 9.45 (s, 2H) | DMSO-$d_6$ |
| 23 | N-hydroxy-4-(5-{4-[5-(2-morpholin-4-yl-ethyl)-2-pyridine-3-yl-thiazol-4-yl]-phenoxy}-pentyloxy)-benzamidine | 1.65 (m, 2H), 1.88 (m, 4H), 2.10 (m, 2H), 2.92 (m, 4H), 3.43 (m, 2H), 4.04 (m, 8H), 6.90-7.00 (m, 4H), 7.37 (m, 1H), 7.57-7.60 (m, 4H), 8.24 (d, 1H), 8.63 (d, 1H), 9.14 (s, 1H) | CDCl$_3$ |
| 24 | N-hydroxy-4-[5-(4-{5-[2-(4-methyl-piperazin-1-yl)-ethyl]-2-pyridine-3-yl-thiazol-4-yl}-phenoxy)-pentyloxy]-benzamidine | 1.70 (m, 2H), 1.89 (m, 4H), 2.81 (m, 3H), 2.86 (m, 2H), 3.01-3.22 (m, 8H), 3.46 (m, 2H), 4.05 (m, 4H), 6.95-6.97 (m, 4H), 7.53-7.59 (m, 4H), 7.76 (m, 1H), 8.35 (d, 1H), 8.64 (d, 1H), 9.16 (s, 1H) | CDCl$_3$ |
| 25 | N-hydroxy-4-(5-{4-[2-pyridine-3-yl-5-(2-thiomorpholin-4-yl-ethyl)-thiazol-4-yl]-phenoxy}-pentyloxy)-benzamidine | 1.60 (m, 2H), 1.82 (m, 4H), 2.51-2.93 (m, 4H), 3.35-3.41 (m, 8H), 4.08 (m, 4H), 6.97-7.08 (m, 4H), 7.55 (m, 1H), 7.66-7.85 (m, 4H), 8.31 (d, 1H), 8.68 (d, 1H), 9.13 (s, 1H) | DMSO-$d_6$ |
| 26 | N-hydroxy-4-(5-{4-[5-(2-imidazol-1-yl-ethyl)-2-pyridine-3-yl-thiazol-4-yl]-phenoxy}-pentyloxy)-benzamidine | 1.60 (m, 2H), 1.82 (m, 4H), 3.54 (m, 2H), 4.07 (m, 4H), 4.53 (t, 2H), 6.99-7.17 (m, 5H), 7.53-7.75 (m, 6H), 7.85 (m, 1H), 8.30 (d, 1H), 8.71 (m, 1H), 9.07 (s, 1H) | DMSO-$d_6$ |
| 27 | N-hydroxy-4-(5-{4-[2-isopropyl-5-(2-morpholin-4-yl-ethyl)-thiazol-4-yl]-phenoxy}-pentyloxy)-benzamidine | 1.32 (d, 6H), 1.58 (m, 2H), 1.78 (m, 4H), 2.39 (m, 4H), 2.52 (m, 2H), 2.98 (m, 2H), 3.25 (m, 1H), 3.57 (m, 4H), 4.04 (m, 4H), 5.72 (s, 2H), 6.96 (m, 4H), 7.50 (d, 2H), 7.59 (d, 2H), 9.46 (s, 1H) | DMSO-$d_6$ |
| 28 | N-hydroxy-4-[5-(4-{2-isopropyl-5-[2-(4-methyl-piperazin-1-yl)-ethyl]-thiazol-4-yl}-phenoxy)-pentyloxy]-benzamidine | 1.32 (d, 6H), 1.56 (m, 2H), 1.80 (m, 4H), 2.22 (s, 3H), 2.49 (m, 10H), 2.97 (m, 2H), 3.22 (m, 1H), 4.04 (m, 4H), 5.72 (s, 2H), 6.96 (m, 4H), 7.50 (d, 2H), 7.59 (d, 2H), 9.46 (s, 1H) | DMSO-$d_6$ |
| 29 | N-hydroxy-4-(5-{4-[5-(2-imidazol-1-yl-ethyl)-2-isopropyl-thiazol-4-yl]-phenoxy}-pentyloxy)-benzamidine | 1.31 (d, 6H), 1.59 (m, 2H), 1.79 (m, 4H), 3.27 (m, 5H), 4.04 (m, 4H), 5.71 (s, 2H), 6.88 (s, 1H), 6.98 (m, 4H), 7.14 (s, 1H), 7.40 (d, 2H), 7.58 (d, 2H), 7.81 (d, 1H), 9.45 (s, 1H) | DMSO-$d_6$ |
| 30 | N-hydroxy-4-[5-(4-{2-isopropyl-5-[2-(2-morpholin-4-yl-ethylamino)-ethyl]-thiazol-4-yl}-phenoxy)-pentyloxy]-benzamidine | 1.32 (d, 6H), 1.58 (m, 2H), 1.79 (m, 4H), 2.32 (m, 6H), 2.60 (m, 2H), 2.81 (m, 2H), 2.99 (m, 2H), 3.23 (m, 1H), 3.52 (m, 4H), 4.03 (m, 4H), 5.71 (s, 2H), 6.98 (m, 4H), 7.53 (m, 4H) | DMSO-$d_6$ |
| 31 | N-hydroxy-4-[5-(4-{5-[2-(3-imidazol-1-yl-propylamino)-ethyl]-2-isopropyl-thiazol-4-yl}-phenoxy)-pentyloxy]-benzamidine | 1.32 (d, 6H), 1.57 (m, 2H), 1.81 (m, 6H), 2.43 (m, 2H), 2.74 (m, 2H), 2.94 (m, 2H), 3.22 (m, 1H), 4.01 (m, 6H), 5.71 (s, 2H), 6.87 (s, 1H), 6.99 (m, 4H), 7.12 (s, 1H), 7.57 (m, 4H), 7.82 (d, 1H) | DMSO-$d_6$ |
| 32 | N-hydroxy-4-(5-{4-[2-isopropyl-5-(2-thiomorpholin-4-yl-ethyl)-thiazol-4-yl]-phenoxy}-pentyloxy)-benzamidine | 1.32 (d, 6H), 1.58 (m, 2H), 1.80 (m, 4H), 2.60 (m, 10H), 2.97 (m, 2H), 3.22 (m, 1H), 4.01 (m, 4H), 5.70 (s, 2H), 6.92 (d, 2H), 6.98 (d, 2H), 7.47 (d, 2H), 7.59 (d, 2H), 9.44 (s, 1H) | DMSO-$d_6$ |
| 33 | N-hydroxy-4-(5-{4-[2-cyclohexyl-5-(2-morpholin-4-yl-ethyl)-thiazol-4-yl]-phenoxy}-pentyloxy)-benzamidine | 1.21 (m, 2H), 1.42 (m, 4H), 1.59 (m, 2H), 1.62 (m, 1H), 1.79 (m, 6H), 2.02 (m, 2H), 2.50 (m, 4H), 2.90 (m, 1H), 2.98 (m, 2H), | DMSO-$d_6$ |

TABLE 1-continued

| Example | Chemical name | ¹H-NMR | solvent |
|---|---|---|---|
| | | 3.56 (m, 4H), 4.02 (m, 4H), 6.73 (s, 2H), 6.93 (d, 2H), 6.99 (d, 2H), 7.49 (d, 2H), 7.57 (d, 2H), 9.46 (s, 1H) | |
| 34 | N-hydroxy-4-[5-(4-{2-cyclohexyl-5-[2-(4-methyl-piperazin-1-yl)-ethyl]-thiazol-4-yl}-phenoxy)-pentyloxy]-benzamidine | 1.22 (m, 1H), 1.42 (m, 4H), 1.58 (m, 2H), 1.68 (m, 1H), 1.79 (m, 6H), 2.04 (m, 2H), 2.14 (m, 4H), 2.50 (m, 7H), 2.90 (m, 1H), 2.97 (m, 2H), 3.45 (m, 2H), 4.01 (m, 4H), 5.72 (m, 2H), 6.92 (d, 2H), 6.98 (d, 2H), 7.48 (d, 2H), 7.57 (d, 2H), 9.46 (s, 1H) | DMSO-$d_6$ |
| 35 | N-hydroxy-4-[5-(4-{2-cyclohexyl-5-[2-(2-morpholin-4-yl-ethylamino)-ethyl]-thiazol-4-yl}-phenoxy)-pentyloxy]-benzamidine | 1.23 (m, 1H), 1.42 (m, 4H), 1.57 (m, 2H), 1.68 (m, 1H), 1.79 (m, 6H), 2.02 (m, 2H), 2.33 (m, 6H), 2.60 (m, 2H), 2.80 (m, 2H), 2.91 (m, 1H), 2.98 (m, 2H), 3.52 (m, 4H), 4.02 (m, 4H), 5.72 (m, 2H), 6.90 (d, 2H), 6.98 (d, 2H), 7.50 (d, 2H), 7.58 (d, 2H), 9.47 (s, 1H) | DMSO-$d_6$ |
| 36 | N-hydroxy-4-(5-{4-[2-cyclohexyl-5-(2-thiomorpholin-4-yl-ethyl)-thiazol-4-yl]-phenoxy}-pentyloxy)-benzamidine | 1.25 (m, 1H), 1.42 (m, 4H), 1.58 (m, 2H), 1.67 (m, 1H), 1.79 (m, 6H), 2.01 (m, 2H), 2.56 (m, 2H), 2.60 (m, 4H), 2.67 (m, 4H), 2.90 (m, 1H), 2.96 (m, 2H), 4.01 (m, 4H), 5.72 (s, 2H), 6.91 (d, 2H), 6.99 (d, 2H), 7.47 (d, 2H), 7.58 (d, 2H), 9.46 (s, 1H) | DMSO-$d_6$ |
| 37 | N-hydroxy-4-(5-{4-[2-cyclohexyl-5-(2-dimethylamino-ethyl)-thiazol-4-yl]-phenoxy}-pentyloxy)-benzamidine | 1.21 (m, 2H), 1.42 (m, 4H), 1.57 (m, 2H), 1.67 (m, 1H), 1.78 (m, 6H), 2.02 (m, 2H), 2.15 (s, 6H), 2.45 (t, 2H), 2.90 (m, 1H), 2.93 (t, 2H), 4.01 (m, 4H), 5.73 (s, 2H), 6.93 (d, 2H), 6.98 (d, 2H), 7.49 (d, 2H), 7.58 (d, 2H), 9.47 (s, 1H) | DMSO-$d_6$ |
| 38 | N-hydroxy-4-(5-{4-[2-cyclohexyl-5-(2-dipropylamino-ethyl)-thiazol-4-yl]-phenoxy}-pentyloxy)-benzamidine | 0.79 (m, 6H), 1.22 (m, 1H), 1.32 (m, 4H), 1.35 (m, 4H0, 1.58 (m, 2H), 1.66 (m, 1H), 1.76 (m, 7H), 2.00 (m, 2H), 2.33 (m, 3H), 2.60 (m, 2H), 2.92 (m, 3H), 4.01 (m, 4H), 5.72 (s, 2H), 6.90 (d, 2H), 6.97 (d, 2H), 7.47 (d, 2H), 7.57 (d, 2H), 9.46 (s, 1H) | DMSO-$d_6$ |
| 39 | N-hydroxy-4-(5-{4-[2-cyclohexyl-5-(2-cyclopropylamino-ethyl)-thiazol-4-yl]-phenoxy}-pentyloxy)-benzamidine | 0.20 (m, 2H), 0.33 (m, 2H), 1.22 (m, 2H), 1.42 (m, 4H), 1.58 (m, 2H), 1.65 (m, 1H), 1.79 (m, 6H), 2.04 (m, 3H), 2.80 (s, 2H), 2.96 (m, 2H), 4.02 (m, 4H), 5.72 (s, 2H), 6.90 (d, 2H), 6.98 (d, 2H), 7.49 (d, 2H), 7.58 (d, 2H), 9.46 (s, 1H) | DMSO-$d_6$ |
| 40 | N-hydroxy-4-[5-(4-{2-amino-5-[2-(2-morpholin-4-yl-ethylamino)-ethyl]-thiazol-4-yl}-phenoxy)-pentyloxy]-benzamidine | 1.58 (m, 1H), 1.79 (m, 4H), 2.35 (m, 6H), 2.69 (m, 2H), 2.78 (m, 4H), 3.54 (m, 4H), 4.01 (m, 4H), 5.71 (s, 2H), 6.93 (m, 4H), 7.44 (d, 2H), 7.59 (d, 2H) | DMSO-$d_6$ |
| 41 | N-hydroxy-4-(5-{4-[5-(2-morpholin-4-yl-ethyl)-2-phenyl-thiazol-4-yl]-phenoxy}-pentloxy)-benzamidine | 1.57 (m, 2H), 1.79 (m, 4H), 2.41 (m, 4H), 2.55 (m, 2H), 3.06 (m, 2H), 3.59 (m, 4H), 4.02 (m, 4H), 7.01 (m, 4H), 7.57 (m, 7H), 7.92 (m, 2H) | DMSO-$d_6$ |
| 42 | N-hydroxy-4-(5-{4-[2-ethyl-5-(2-morpholin-4-yl-ethyl)-thiazol-4-yl]-phenoxy}-pentyloxy)-benzamidine | 1.28 (t, 3H), 1.59 (m, 2H), 1.79 (m, 4H), 2.39 (m, 4H), 2.49 (m, 2H), 2.92 (q, 2H), 2.98 (t, 2H), 3.56 (t, 4H), 4.01 (q, 4H), 5.70 (s, 2H), 6.92 (d, 2H), 6.98 (d, 2H), 7.49 (d, 2H), 7.57 (d, 2H), 9.43 (s, 1H) | DMSO-$d_6$ |
| 43 | N-hydroxy-4-(5-{4-[2-ethyl-5-(2-thiomorpholin-4-yl-ethyl)-thiazol-4-yl]-phenoxy}-pentyloxy)-benzamidine | 1.28 (m, 3H), 1.57 (m, 2H), 1.79 (m, 5H), 2.50 (m, 2H), 2.54 (m, 1H), 2.60 (m, 2H), 2.66 (m, 2H), 2.91 (m, 4H), 3.16 (m, 2H), 4.00 (m, 4H), 5.70 (s, 2H), 6.91 (d, 2H), 6.98 (d, 2H), 7.47 (d, 2H), 7.58 (d, 2H), 9.43 (s, 1H) | DMSO-$d_6$ |
| 44 | N-hydroxy-4-(4-{4-[2-methyl-5-(2-morpholin-4-yl-ethyl)-thiazol-4-yl]-phenoxy}-butoxy)-benzamidine | 1.89 (m, 4H), 2.39 (m, 4H), 2.50 (m, 2H), 2.60 (s, 3H), 2.98 (t, 2H), 3.57 (t, 4H), 4.06 (m, 4H), 5.71 (s, 2H), 6.94 (d, 2H), 6.99 (d, 2H), 7.49 (d, 2H), 7.58 (d, 2H), 9.45 (s, 1H) | DMSO-$d_6$ |

EXAMPLES 45 AND 46

The compounds (20) obtained in the same manner as in the Preparative Example 2-4 were prepared in the same manner as Example 2, obtaining the title compounds.

The ¹H-NMR data of the title compounds are shown in Table 2.

TABLE 2

| Example | Chemical name | ¹H-NMR | solvent |
|---|---|---|---|
| 45 | 4-(5-{4-[2-cyclohexyl-5-(2-morpholin-4-yl-ethyl)-thiazol-4-yl]-phenoxy}-pentyloxy)-benzamidine | 1.20 (m, 2H), 1.41 (m, 4H), 1.59 (m, 2H), 1.62 (m, 1H), 1.78 (m, 6H), 2.01 (m, 2H), 2.49 (m, 4H), 2.90 (m, 1H), 2.98 (m, 2H), 3.56 (m, 4H), 4.02 (m, 4H), 6.93 (d, 2H), 6.99 (d, 2H), 7.49 (d, 2H), 7.57 (d, 2H), 9.10 (brs, 3H) | DMSO-$d_6$ |
| 46 | 4-(5-{4-[2-methyl-5-(2-morpholin-4-yl-ethyl)-thiazol-4-yl]-phenoxy}-pentyloxy)-benzamidine | 1.59 (m, 2H), 1.81 (m, 4H), 2.40 (m, 4H), 2.60 (s, 3H), 2.96 (m, 2H), 3.31 (m, 2H), 3.57 (m, 4H), 4.10 (m, 4H), 6.98 (d, 2H), 7.16 (d, 2H), 7.49 (d, 2H), 7.80 (d, 2H), 9.09 (brs, 3H) | DMSO-$d_6$ |

EXAMPLES 47 TO 51

The compounds (20) obtained in the same manner as in the Preparative Example 2-4 were prepared in the same manner as Example 1, obtaining the title compounds.

The ¹H-NMR data of the title compounds are shown in Table 3.

EXAMPLES 53 TO 58

The compounds (22) obtained in the same manner as in the Preparative Example 3-1 were prepared in the same manner as Example 1, obtaining the title compounds.

The ¹H-NMR data of the title compounds are shown in Table 5.

TABLE 3

| Example | Chemical name | ¹H-NMR | solvent |
|---|---|---|---|
| 47 | N-hydroxy-4-(5-{4-[2-methylamino-5-(2-morpholin-4-yl-ethyl)-thiazol-4-yl]-phenoxy}-pentyloxy)-benzamidine | 1.57 (m, 2H), 1.79 (m, 4H), 2.39 (m, 4H), 2.50 (m, 2H), 2.81 (s, 3H), 2.84 (m, 2H), 3.58 (m, 4H), 4.00 (m, 4H), 5.74 (brs, 2H), 6.92 (m, 4H), 7.27 (m, 1H), 7.44 (m, 2H), 7.59 (m, 2H), 9.47 (brs, 1H) | DMSO-$d_6$ |
| 48 | N-hydroxy-4-[5-(4-{2-methylamino-5-[2-(4-methyl-piperazin-1-yl)-ethyl]-thiazol-4-yl}-phenoxy)-pentyloxy]-benzamidine | 1.58 (m, 2H), 1.80 (m, 4H), 2.50 (s, 3H), 2.79 (m, 6H), 2.85 (m, 3H), 3.38 (m, 6H), 4.01 (m, 4H), 5.75 (brs, 2H), 6.92 (m, 4H), 7.43 (m, 2H), 7.60 (m, 2H), 9.46 (brs, 1H) | DMSO-$d_6$ |
| 49 | N-hydroxy-4-(5-{4-[2-methylamino-5-(2-thiomorpholin-4-yl-ethyl)-thiazol-4-yl]-phenoxy}-pentyloxy)-benzamidine | 1.58 (m, 2H), 1.79 (m, 4H), 2.60 (m, 4H), 2.65 (m, 4H), 2.78 (m, 4H), 3.33 (s, 3H), 5.71 (s, 2H), 6.93 (m, 4H), 7.43 (d, 2H), 7.58 (d, 2H), 9.44 (s, 1H) | DMSO-$d_6$ |
| 50 | N-hydroxy-4-[5-(4-{2-methylamino-5-[2-(2-morpholin-4-yl-ethylamino)-ethyl]-thiazol-4-yl}-phenoxy)-pentyloxy]-benzamidine | 1.58 (m, 2H), 1.79 (m, 4H), 2.30 (m, 4H), 2.55 (m, 4H), 2.71 (m, 2H), 2.79 (m, 4H), 3.34 (s, 3H), 3.52 (m, 4H), 4.00 (m, 4H), 5.71 (s, 2H), 6.94 (m, 4H), 7.46 (d, 2H), 7.59 (d, 2H), 9.46 (s, 1H) | DMSO-$d_5$ |
| 51 | N-hydroxy-4-[5-(4-{5-[2-(3-imidazol-1-yl-propylamino)-ethyl]-2-methylamino-thiazol-4-yl}-phenoxy)-pentyloxy]-benzamidine | 1.58 (m, 2H), 1.78 (m, 6H), 2.42 (m, 2H), 2.66 (m, 2H), 2.78 (m, 4H), 3.34 (s, 3H), 4.01 (m, 4H), 5.71 (s, 2H), 6.86 (s, 1H), 6.94 (m, 4H), 7.13 (s, 1H), 7.25 (d, 1H), 7.44 (d, 2H), 7.58 (d, 2H), 9.46 (s, 1H) | DMSO-$d_6$ |

EXAMPLES 52

The compound (20) obtained in the same manner as in the Preparative Example 2-4 was prepared in the same manner as Example 2, obtaining the title compound.

The ¹H-NMR data of the title compound are shown in Table 4.

TABLE 4

| Example | Chemical name | ¹H-NMR | solvent |
|---|---|---|---|
| 52 | 4-(5-{4-[2-methylamino-5-(2-morpholin-4-yl-ethyl)-thiazol-4-yl]-phenoxy}-pentyloxy)-benzamidine | 1.58 (m, 2H), 1.78 (m, 4H), 2.40 (m, 4H), 2.49 (m, 2H), 2.80 (s, 3H), 2.84 (m, 2H), 3.58 (m, 4H), 4.01 (m, 4H), 6.92 (m, 4H), 7.27 (m, 1H), 7.44 (m, 2H), 7.59 (m, 2H), 9.09 (brs, 3H) | DMSO-$d_6$ |

TABLE 5

| Example | Chemical name | $^1$H-NMR | solvent |
|---|---|---|---|
| 53 | N-hydroxy-4-(5-{4-[2-dimethylamino-5-(2-morpholin-4-yl-ethyl)-thiazol-4-yl]-phenoxy}-pentyloxy)-benzamidine | 1.58 (m, 2H), 1.79 (m, 4H), 2.38 (m, 4H), 2.48 (m, 2H), 2.86 (t, 2H), 3.00 (s, 6H), 3.57 (m, 4H), 4.01 (m, 4H), 5.71 (s, 2H), 6.94 (m, 4H), 7.45 (d, 2H), 7.58 (d, 2H), 9.45 (s, 1H) | DMSO-d$_6$ |
| 54 | N-hydroxy-4-(5-{4-[2-dimethylamino-5-(2-thiomorpholin-4-yl-ethyl)-thiazol-4-yl]-phenoxy}-pentyloxy)-benzamidine | 1.58 (m, 2H), 1.79 (m, 4H), 2.51 (m, 2H), 2.61 (m, 4H), 2.66 (m, 4H), 2.89 (m, 2H), 3.00 (s, 6H), 4.01 (m, 4H), 5.71 (s, 2H), 6.95 (m, 4H), 7.44 (d, 2H), 7.59 (d, 2H), 9.44 (s, 1H) | DMSO-d$_6$ |
| 55 | N-hydroxy-4-(5-{4-[2-(isobutyryl-methyl-amino)-5-(2-morpholin-4-yl-ethyl)-thiazol-4-yl]-phenoxy}-pentyloxy)-benzamidine | 1.15 (d, 6H), 1.58 (m, 2H), 1.79 (m, 4H), 2.40 (m, 4H), 2.78 (m, 1H), 2.97 (m, 2H), 3.33 (s, 3H), 3.57 (m, 4H), 3.59 (m, 2H), 4.01 (m, 4H), 5.71 (s, 2H), 6.93 (d, 2H), 6.99 (d, 2H), 7.51 (d, 2H), 7.60 (d, 2H), 9.44 (s, 1H) | DMSO-d$_6$ |
| 56 | N-hydroxy-4-(5-{4-[2-[benzyl-(2-morpholin-4-yl-ethyl)-amino]-5-(2-morpholin-4-yl-ethyl)-thiazol-4-yl]-phenoxy}-pentyloxy)-benzamidine | 1.57 (m, 2H), 1.78 (m, 4H), 2.37 (m, 8H), 2.49 (m, 2H), 2.83 (m, 2H), 3.16 (m, 2H), 3.53 (m, 10H), 3.98 (m, 4H), 4.66 (s, 2H), 5.72 (s, 2H), 6.95 (m, 4H), 7.27 (m, 1H), 7.33 (m, 4H), 7.43 (m, 2H), 7.56 (m, 2H), 9.46 (s, 1H) | DMSO-d$_6$ |
| 57 | N-hydroxy-4-(5-{4-[2-diethylamino-5-(2-morpholin-4-yl-ethyl)-thiazol-4-yl]-phenoxy}-pentyloxy)-benzamidine | 1.15 (m, 6H), 1.57 (m, 2H), 1.79 (m, 4H), 2.38 (m, 4H), 2.48 (m, 2H), 2.83 (m, 2H), 3.40 (m, 4H), 3.57 (m, 4H), 4.02 (m, 4H), 5.71 (s, 2H), 6.94 (m, 4H), 7.45 (d, 2H), 7.58 (d, 2H), 9.45 (s, 1H) | DMSO-d$_6$ |
| 58 | N-hydroxy-4-(5-{4-[2-[bis-(2-methoxy-ethyl)-amino]-5-(2-morpholin-4-yl-ethyl)-thiazol-4-yl]-phenoxy}-pentyloxy)-benzamidine | 1.57 (m, 2H), 1.79 (m, 4H), 2.39 (m, 4H), 2.49 (m, 2H), 2.84 (m, 2H), 3.27 (s, 6H), 3.56 (m, 12H), 4.01 (m, 4H), 5.71 (s, 2H), 6.93 (m, 4H), 7.43 (d, 2H), 7.59 (d, 2H), 9.44 (s, 1H) | DMSO-d$_6$ |

EXAMPLES 59 TO 63

The compounds (24) obtained in the same manner as in the Preparative Example 4-1 were prepared in the same manner as Example 1, obtaining the title compounds.

The $^1$H-NMR data of the title compounds are shown in Table 6.

TABLE 6

| Example | Chemical name | $^1$H-NMR | solvent |
|---|---|---|---|
| 59 | N-hydroxy-4-(5-{4-[2-morpholin-4-yl-5-(2-morpholin-4-yl-ethyl)-thiazol-4-yl]-phenoxy}-pentyloxy)-benzamidine | 1.58 (m, 2H), 1.80 (m, 4H), 2.43 (m, 4H), 3.32 (m, 8H), 3.58 (m, 8H), 4.05 (m, 4H), 5.71 (brs, 2H), 6.92 (m, 4H), 7.43 (m, 2H), 7.59 (m, 2H), 9.45 (brs, 1H) | DMSO-d$_6$ |
| 60 | N-hydroxy-4-(5-{4-[2-morpholin-4-yl-5-(2-thiomorpholin-4-yl-ethyl)-thiazol-4-yl]-phenoxy}-pentyloxy)-benzamidine | 1.58 (m, 2H), 1.80 (m, 4H), 2.68 (m, 8H), 2.85 (m, 2H), 3.33 (m, 6H), 3.70 (m, 4H), 4.02 (m, 4H), 5.71 (s, 2H), 6.95 (m, 4H), 7.44 (d, 2H), 7.59 (d, 2H), 9.44 (s, 1H) | DMSO-d$_6$ |
| 61 | N-hydroxy-4-[5-(4-{5-[2-(4-methyl-piperazin-1-yl)-ethyl]-2-morpholin-4-yl-thiazol-4-yl}-phenoxy)-pentyloxy]-benzamidine | 1.58 (m, 2H), 1.78 (m, 4H), 2.41 (s, 3H), 2.51 (m, 5H), 2.75 (m, 3H), 2.88 (m, 2H), 3.08 (m, 6H), 3.70 (m, 4H), 4.01 (m, 4H), 6.96 (m, 4H), 7.45 (d, 2H), 7.69 (d, 2H) | DMSO-d$_6$ |
| 62 | N-hydroxy-4-[5-(4-{2-morpholin-4-yl-5-[2-(2-morpholin-4-yl-ethylamino)-ethyl]-thiazol-4-yl}-phenoxy)-pentyloxy]-benzamidine | 1.59 (m, 2H), 1.79 (m, 4H), 2.30 (m, 4H), 2.50 (m, 4H), 2.97 (m, 2H), 3.37 (m, 4H), 3.50 (m, 6H), 3.71 (t, 4H), 4.01 (t, 4H), 5.70 (d, 2H), 6.94 (m, 4H), 7.42 (d, 2H), 7.51 (d, 2H), 7.58 (d, 2H), 9.44 (s, 1H) | DMSO-d$_6$ |
| 63 | N-hydroxy-4-(5-{4-[5-(2-morpholin-4-yl-ethyl)-2-piperidin-1-yl-methyl-thiazol-4-yl]-phenoxy}-pentyloxy)-benzamidine | 1.38 (m, 2H), 1.49-1.56 (m, 6H), 1.76 (m, 4H), 2.37-2.49 (m, 8H), 2.98 (m, 2H), 3.54 (m, 4H), 3.67 (m, 2H), 3.99 (m, 6H), 6.90-6.97 (m, 4H), 7.47-7.56 (m, 4H) | DMSO-d$_6$ |

The compound (24) obtained in the same manner as in the Preparative Example 4-1 was prepared in the same manner as Example 2, obtaining the title compound. The $^1$H-NMR data of the title compound are shown in Table 7.

EXAMPLE 64

TABLE 7

| Example | Chemical name | $^1$H-NMR | solvent |
|---|---|---|---|
| 64 | 4-(5-{4-[2-morpholin-4-yl-5-(2-morpholin-4-yl-ethyl)-thiazol-4-yl]-phenoxy}-pentyloxy)-benzamidine | 1.59 (m, 2H), 1.80 (m, 4H), 2.43 (m, 4H), 3.32 (m, 8H), 3.598 (m, 8H), 4.05 (m, 4H), 6.92 (m, 4H), 7.42 (m, 2H), 7.59 (m, 2H), 9.10 (brs. 3H) | DMSO-$d_6$ |

EXAMPLE 65

The compound (14a) obtained in the same manner as in the Preparative Example 5-3 was prepared in the same manner as Example 1, obtaining the title compound.
The $^1$H-NMR data of the title compound are shown in Table 8.

TABLE 8

| Example | Chemical name | $^1$H-NMR | solvent |
|---|---|---|---|
| 65 | N-hydroxy-(5-{4-[5-(2-isobutyrylamino-ethyl)-2-methyl-thiazol-4-yl]-phenoxy}-pentyloxy)-benzamidine | 0.97 (d, 6H), 1.59 (m, 2H), 1.80 (m, 4H), 2.30 (m, 1H), 2.62 (s, 3H), 2.97 (m, 2H), 3.26 (m, 2H), 4.03 (m, 4H), 5.71 (s, 2H), 6.97 (m, 4H), 7.50 (d, 2H), 7.59 (d, 2H), 7.96 (m, 1H), 9.45 (s, 1H) | DMSO-$d_6$ |

EXAMPLES 66 TO 68

The compounds (29) obtained in the same manner as in the Preparative Example 6-2 were prepared in the same manner as Example 1, obtaining the title compounds.
The $^1$H-NMR data of the title compounds are shown in Table 9.

TABLE 9

| Example | Chemical name | $^1$H-NMR | solvent |
|---|---|---|---|
| 66 | N-hydroxy-4-{5-[4-(5-{2-[isobutyl-(pyridine-3-carbonyl)-amino]-ethyl}-2-methyl-thiazol-4-yl)-phenoxy]-pentyloxy}-benzamidine | 0.62 (d, 3H), 0.86 (d, 3H), 1.22 (s, 3H), 1.57 (m, 2H), 1.79 (m, 5H), 2.56 (s, 2H), 2.66 (s, 1H), 2.98 (m, 2H), 3.15 (m, 1H), 3.21 (m, 1H), 3.42 (m, 1H), 3.63 (m, 1H), 4.02 (t, 2H), 4.09 (m, 2H), 5.72 (s, 2H), 6.91 (d, 2H), 6.98 (d, 2H), 7.09 (d, 4H), 7.23 (d, 2H), 8.59 (d, 2H), 9.45 (s, 1H) | DMSO-$d_6$ |
| 67 | N-hydroxy-4-{5-[4-(5-{2-[cyclopropyl-(pyridine-4-carbonyl)-amino]-ethyl}-2-isopropyl-thiazol-4-yl)-phenoxy]-pentyloxy}-benzamidine | 0.37 (m, 2H), 0.44 (m, 2H), 1.33 (d, 6H), 1.58 (m, 2H), 1.79 (m, 4H), 2.70 (m, 1H), 3.24 (m, 2H), 3.35 (m, 2H), 3.68 (m, 1H), 4.00 (m, 4H), 5.72 (s, 2H), 6.90 (d, 2H), 7.00 (m, 2H), 7.35 (m, 2H), 7.59 (m, 4H), 8.63 (m, 2H), 9.45 (s, 1H) | DMSO-$d_6$ |
| 68 | N-hydroxy-4-{5-[4-(2-cyclohexyl-5-{2-[cyclopropyl-(pyridine-3-carbonyl)-amino]ethyl}-thiazol-4-yl)-phenoxy]-pentyloxy}-benzamidine | 0.36 (m, 2H), 0.47 (m, 2H), 1.22 (m, 1H), 1.43 (m, 4H), 1.57 (m, 2H), 1.66 (m, 1H), 1.78 (m, 6H), 2.02 (m, 2H), 2.77 (m, 1H), 2.95 (m, 1H), 3.27 (m, 2H), 3.70 (m, 2H), 4.02 (m, 4H), 5.72 (s, 2H), 6.90 (d, 2H), 6.97 (m, 2H), 7.43 (m, 1H), 7.59 (m, 3H), 7.82 (m, 2H), 8.60 (m, 2H), 9.46 (s, 1H) | DMSO-$d_6$ |

EXAMPLES 69 TO 72

The compounds (36) obtained in the same manner as in the Preparative Example 7-6 were prepared in the same manner as Example 1, obtaining the title compounds.

The $^1$H-NMR data of the title compounds are shown in Table 10.

TABLE 10

| Example | Chemical name | $^1$H-NMR | solvent |
|---|---|---|---|
| 69 | N-hydroxy-4-{5-4-(5-methylcarbamoyl-2-methyl-thiazol-4-yl)-phenoxy]-pentyloxy}-benzamidine | 1.57 (m, 2H), 1.80 (m, 4H), 2.69 (s, 6H), 4.03 (m, 4H), 5.73 (brs, 2H), 6.97 (m, 4H), 7.61 (m, 4H), 9.46 (brs, 1H) | DMSO-$d_6$ |
| 70 | N-hydroxy-4-{5-[4-(5-isopropylcarbamoyl-2-methyl-thiazol-4-yl)-phenoxy]-pentyloxy}-benzamidine | 1.04 (d, 6H), 1.58 (m, 2H), 1.80 (m, 4H), 2.70 (s, 3H), 4.02 (m, 4H), 4.16 (m, 1H), 5.73 (brs, 2H), 6.98 (m, 4H), 7.60 (m, 4H), 9.46 (brs, 1H) | DMSO-$d_6$ |
| 71 | N-hydroxy-4-{5-[4-(5-{3-imidazol-1-yl-propylcarbamoyl}-2-methyl-thiazol-4-yl)-phenoxy]-pentyloxy}-benzamidine | 1.57 (m, 2H), 1.77 (m, 6H), 2.11 (brs, 3H), 3.36 (m, 2H), 3.91 (m, 2H), 4.00 (m, 4H), 5.71 (m, 2H), 6.80 (m, 2H), 6.94 (m, 4H), 7.25 (m, 2H), 7.56 (m, 1H), 7.75 (m, 1H), 7.84 (m, 1H), 8.30 (brs, 1H) | DMSO-$d_6$ |
| 72 | N-hydroxy-4-{5-[4-(2-amino-5-methylcarbamoyl-thiazol-4-yl)-phenoxy]-pentyloxy}-benzamidine | 1.57 (m, 2H), 1.78 (m, 4H), 2.60 (s, 3H), 4.01 (m, 4H), 5.75 (brs, 2H), 6.914 (m, 4H), 7.46 (m, 2H), 7.58 (m, 2H), 9.48 (brs, 1H) | DMSO-$d_6$ |

EXPERIMENTAL EXAMPLE 1

Inhibitory Effects on Osteoclast Differentiation

The effect of the benzamidine derivative of the present invention on osteoclast formation and differentiation process was evaluated via co-culture with an osteoblast.

1-1: Preparation of Cells a) Preparation of Bone Marrow Cells

Tibia was aseptically ectomized from male 6 to 8-week-old ddY mice to harvest bone marrow cells by using a syringe (21G, Korea Green Cross). The bone marrow cells were suspended in 5 mL of an α-MEM medium (Gibco BRL Co., added with sodium bicarbonate (2.0 g/L), streptomycin (100 mg/L) and penicillin (100,000 unit/mL), filtered and then sterilized). The harvested cells were centrifuged at 600×g for 5 mins to collect the whole quantity. To remove the red blood cells in the bone marrow cells, 3 mL of Tris HCl (0.83% $NH_4Cl$, pH 7.5) was added and well mixed. After centrifuging above cells, the numbers of the eukaryotic cells in the harvested bone marrow cells were counted and then immediately used for a co-culture system.

b) Preparation of Osteoblast

The progenitor bone and the parietal bone were aseptically ectomized from 1 to 2-day-old neonate ICR mice, washed with a phosphate butter solution (PBS) and treated with a mixed enzyme solution (of 0.2% collagenase and 0.1% dispase) sequentially (10, 10, 10, 20, 20 and 20 min), and then 3 to 6 groups of the cells which comprise lot of cells having the characteristics of the osteoblast were intensively collected and washed with a medium (a serum-free α-MEM). The washed cells were cultured in the α-MEM medium containing 10% FBS for 2 to 3 days. After subculturing, the collected cells were used for this experiment, and diluted to a concentration of 1×10$^6$ cells/mL for storage at −70□.

1-2. Measurement of Osteoclast Differentiation a) Preparation of Sample

The benzamidine derivative of the present invention was dissolved in a sterile distilled water or ethanol to dilute to a desired concentration. The final volume of the sample added to the cell culture medium was set at a ratio of 1:1000.

b) Reaction with Sample Via Co-Culture System

The bone marrow cells prepared in the above 1-1 and the osteoblast were co-cultured for osteoclast differentiation. Both the bone marrow cells (25,000 cells/cm$^2$) and the osteoblast (10,000 cells/cm$^2$) were plated in a 96-well plate using α-MEM medium containing FBS, and then cultured with the samples to be tested for 7 days. Differentiation factors, such as dexamethasone (10$^{-7}$ M) and vitamin $D_3$ (10$^{-8}$ M), were also co-added to the medium from the first day of cultivation. The medium was changed with a fresh media containing a mixture of the samples and the differentiation factors every 2 to 3 days.

c) Evaluation of Osteoclast Differentiation

1) Preparation of Tartaric Acid Resistance Phosphatase (TRAP) Staining Solution

TRAP was used as a marker to measure the matured osteoclast in consideration of its characteristics showing a positive reaction to a TRAP staining solution. The TRAP staining solution was prepared in such the manner that 5 mg of naphtol AS-MS phosphate (sigma N-4875) as a substrate, and 25 mg of a coloring agent (Fast Red Violet LB salt) were dissolved in N,N-dimethylformamide (about 0.5 mL). 50 ml of a 0.1 N $NaHCO_3$ buffer solution containing 50 mM tartaric acid (pH 5.0) was added thereto, and the mixture was stored at a refrigerator prior to use as a staining solution.

2) Staining Method

After culturing the cells for 7 days, the medium was removed from the wells, the cells were once washed with PBS, and then fixed with PBS containing 10% formalin for 2 to 5 min. The cells were fixed again in a mixed solution of ethanol and acetone (1/1) for about 1 min, and dried off. The cells were further treated by the TRAP staining solution for 15 mins and washed with water and dried off. The osteoclasts with 3 or more nuclei showing a TRAP-positive reaction were counted under a microscopic examination. Each of tests was confirmed over at least three times. The inhibitory effect on osteoclast differentiation of each experimental group, relative to negative controls, was expressed as a percentage (%).

The results are shown in Table 11.

TABLE 11

| Example | inhibitory effect on osteoclast differentiation(%) 1 μm |
|---|---|
| 1 | 61 |
| 3 | 90.7 |
| 4 | 72.8 |
| 5 | 93.5 |
| 6 | 59 |
| 7 | 48 |
| 8 | 11 |
| 9 | 91.7 |
| 10 | 55 |
| 11 | 70 |
| 12 | 56 |
| 13 | 43 |
| 14 | 100 |
| 15 | 99 |
| 16 | 51 |

TABLE 11-continued

| Example | inhibitory effect on osteoclast differentiation(%) 1 μm |
|---|---|
| 17 | 40 |
| 18 | 100 |
| 19 | 100 |
| 20 | 94 |
| 21 | 58 |
| 22 | 61 |
| 23 | 91 |
| 24 | 86 |
| 25 | 65 |
| 26 | 24 |
| 27 | 81 |
| 28 | 90 |
| 29 | 85 |
| 30 | 78 |
| 31 | 97 |
| 32 | 97 |
| 33 | 92 |
| 34 | 100 |
| 35 | 100 |
| 36 | 100 |
| 37 | 100 |
| 38 | 100 |
| 39 | 100 |
| 40 | 24.6 |
| 41 | 100 |
| 42 | 100 |
| 43 | 97.7 |
| 46 | 63.4 |
| 47 | 89.6 |
| 48 | 60.6 |
| 49 | 84 |
| 50 | 37 |
| 51 | 32 |
| 53 | 99.3 |
| 54 | 88 |
| 55 | 69 |
| 56 | 100 |
| 57 | 100 |
| 58 | 100 |
| 59 | 58 |
| 60 | 88 |
| 61 | 76 |
| 62 | 43.6 |
| 63 | 99.2 |
| 65 | 29 |
| 69 | 90.3 |
| 70 | 84.8 |
| 71 | 90.4 |
| 72 | 97.6 |

As shown in Table 11, the results indicate that the thiazole derivative-substituted benzamidine derivative of the present invention effectively inhibited the osteoclast differentiation at an extremely low concentration.

EXPERIMENTAL EXAMPLE 2

Cytotoxicity Test

The cytotoxic effect of the benzamidine derivative of the present invention was evaluated by carrying out the experiment described below.

The test substance was diluted in an appropriate solvent at a $10^{-2}$ M concentration. This substance was diluted in an appropriate culture medium for the cells used in the cytotoxicity test to a concentration of 10 M, and loaded into a 96-well plate in 100 μl per well. The cell lines to be used in the cytotoxicity test were plated on a 96-well plate in a dose of $1.0 \times 10^4$ cells/100 μl per well and cultured for 72 hrs. 25 μl of MTT [3-(4,5-dimethyl-2-thiazolyl)-2,5-diphenyl-2H-tetrazolium bromide] dissolved in PBS (2 mg/mL) were added before 4 hrs of the end of culture. After completion of the reaction, the plates were centrifuged, the medium was discarded and 100 μl of DMSO was added to dissolve formazan. Finally, the absorbance of the developed plates was measured at 540 nm. The survival rates of the cells were expressed as % concentration values in comparison with the control group.

The results are shown in Table 12.

TABLE 12

| Example | survival rates of the cells ($10^{-6}$M) | | |
|---|---|---|---|
| | MC3T3 | calvaria | HOS |
| 18 | 94.4 | 97.3 | 99.7 |
| 35 | 98.6 | 81.6 | 115.7 |
| 36 | 97.6 | 89.1 | 81.4 |
| 37 | 94.9 | 84.7 | 116.7 |
| 38 | 104.7 | 94.9 | 96.2 |
| 39 | 85.0 | 93.1 | 111.0 |
| 40 | 102.2 | 99.7 | 103.2 |
| 41 | 85.9 | 78.6 | 78.8 |
| 42 | 81.5 | 73.8 | 98.9 |
| 43 | 86.5 | 91.9 | 80.4 |
| 44 | 101.3 | 90.6 | 105.6 |
| 45 | 108.2 | 90.5 | 106.9 |
| 46 | 95.3 | 99.9 | 94.1 |
| 50 | 97.2 | 92.8 | 93.6 |
| 51 | 93.8 | 91.7 | 99.6 |
| 52 | 115.6 | 100.1 | 98.8 |
| 56 | 86.0 | 84.0 | 98.8 |
| 57 | 86.8 | 87.0 | 90.7 |
| 58 | 79.2 | 76.8 | 85.4 |
| 62 | 97.0 | 92.7 | 95.1 |
| 63 | 89.4 | 86.9 | 86.5 |
| 64 | 119.8 | 99.4 | 107.8 |
| 66 | 111.1 | 99.0 | 105.9 |
| 67 | 80.7 | 95.3 | 97.5 |
| 68 | 90.3 | 91.4 | 82.9 |

As shown in Table 12, the results indicate that the benzamidine derivative of the present invention shows little cytotoxicity.

EXPERIMENTAL EXAMPLE 3

Therapeutic Effect in Osteoporosis in Mouse Model Suffering Osteoporosis Induced by Ovariectomy The therapeutic effect of each benzamidine derivate of the present invention was evaluated on the ovariectomized white mouse. The substances of Examples 18, 19 and 72 were administered from 4 weeks after operation for 4 weeks and the substances of Examples 27, 33, 36, 47, 53 and 59 were administered from 3 days after operation for 29 days. Thereafter, the changes in the trabecular bone volume (TBV) of the femur were observed via histomorphometry.

3-1. Animals and Husbandry

Female ddY mice (6-week-old, SLC, Japan) were used after acclimatization for 7 days. Animals to be test were allocated 5 per a plastic cage for mice, and raised in a temperature (20 to 25□) and humidity (30 to 35%) controlled room. Feed and water were supplied free to access.

3-2: Preparations and Administration of Samples

Salts of the benzamidine derivative of the present invention (methanesulfonic acid or HCl) were dissolved or suspended in sterilized, distilled water or 5% DMSO, and administered at a dose of 10 ml per body weight (kg) in the form of a solution. The substances of Examples 18, 19 and 72 were administered from 4 weeks after operation for 4 weeks, and the substances of Examples 27, 33, 36, 47, 53 and 59 were administered from 3 days after operation for 29 days each at 50 mg/kg/day.

3-3: Osteoporosis Induced by Ovariectomy

After all animals anesthetize using ketamine hydrochloride and xylazine hydrochloride, bilateral ovaries were removed in order to induce estrogen-deficient osteoporosis. After ovariectomy, the ovaries were closed by routine methods.

3-4: Histology

The left femur was separated at a final sacrifice day, and fixed in 10% neutral formalin, then decalcified in a decalcifying solution (solution composed of 2.44% formic acid, and 0.5 N sodium hydroxide). The decalcifying solution was exchanges once a day for 5 days. After completion of the decalcification, the femur was embedded in paraffin, sectioned (3 to 4 µM), and stained with a hematoxylin-eosin stain. Observation was made using optical micrography.

3-5: Histomorphometry

The trabecular bone volume was calculated using automated image analysis (analysis Image Processing; SIS, Germany) in the femur using a femur histological specimen prepared in the above manner. The trabecular bone volume was calculated as percentage (%) levels.

3-6: Changes in Trabecular Bone Volume

All the numeral values were determined and compared to that of the vehicle control used in each experiment, using the calculation by the following Equation 1. The results are shown in Table 13.

Change(%)=[(trabecular bone volume of $a$–trabecular bone volume of $b$)/trabecular bone volume of $b$]×100          [Equation 1]

a: Experiment group, b: Vehicle group

TABLE 13

| Example | Changes in trabecular bone volume (% relative to vehicle control) |
|---|---|
| 18 | 139.09 |
| 19 | 2.99 |
| 27 | 23.62 |
| 33 | 26.32 |
| 36 | 26.59 |
| 59 | 5.66 |
| 72 | 95.57 |
| 47 | 5.77 |
| 53 | 25.65 |

As shown in the table 13, the benzamidine derivative of the present invention greatly increased the trabecular bone volume. Thus, the benzamidine derivative of the present invention proves to be effective for the prevention and treatment of osteoporosis.

Hereinbelow, Formulation Example for the composition of the present invention is described.

FORMULATION EXAMPLE

Pharmaceutical Preparation

1. Preparation of powders

| | |
|---|---|
| Benzamidine derivative of the formula 1 | 2 g |
| Lactose | 1 g |

The above-components were mixed and then filled into an air tight bag, thus to prepare a powder.

2. Preparation of tablets

| | |
|---|---|
| Benzamidine derivative of the formula 1 | 100 mg |
| Corn starch | 100 mg |
| Lactose | 100 mg |
| Magnesium stearate | 2 mg |

The above-components were mixed, and then tabletted with a common tableting method to prepare a tablet.

3. Preparation of capsules

| | |
|---|---|
| Benzamidine derivative of the formula 1 | 100 mg |
| Corn starch | 100 mg |
| Lactose | 100 mg |
| Magnesium stearate | 2 mg |

The above-components were mixed, and then filled into a gelatin capsule with a common method for capsule preparation to prepare a capsule.

4. Preparation of injections

| | |
|---|---|
| Benzamidine derivative of the formula 1 | 10 µg/ml |
| Dilute hydrochloric acid BP | to pH 3.5 |
| NaCl for injections BP | max. 1 ml |

The benzamidine derivatives of the formula 1 was dissolved in an adequate volume of injection sodium chloride BP, then pH of the resulting solution was controlled to pH 3.5 with dilute hydrochloric acid BP. The volume of the solution was adjusted with injectablr sodium chloride BP, and the solution was mixed fully. The solution was filled into a type I ampoule made with glass, and then the ampoule was sealed under the upper air lattice by melting glass. The sealed ampoule was autoclaved at 120□ for 15 mins or longer for sterilization to prepare an injection.

INDUSTRIAL APPLICATION

The benzamidine derivative of the present invention effectively inhibits asteoclast differentiation at an extremely low concentration, and greatly increases the trabecular bone volume, and thus it can be advantageously used for the prevention and treatment of asteoporosis.

The invention claimed is:

1. A benzamidine derivative represented by the following formula 1:

<Formula 1>

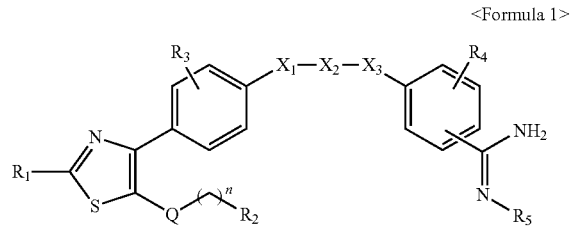

wherein R₁ is C₁ to C₆ alkyl which is unsubstituted or substituted with one group selected from pyridine and

C₃ to C₆ cycloalkyl; phenyl; benzyl; pyridinyl which is unsubstituted or substituted with C₁ to C₆ alkyl; guanidino; NR₆R₇;

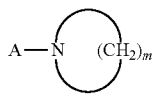

(wherein A is C₁ to C₆ alkyl, and m is an integer of 2 to 6); or

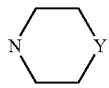

group which is unsubstituted or substituted with C₁ to C₆ alkyl;

R₂ is a primary or secondary amine, which is NR₈R₉,

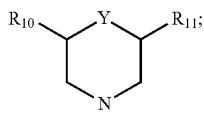

pyrrolidine, piperidine or imidazole;

R₃ and R₄ are each independently hydrogen; halogen; hydroxy; C₁ to C₆ alkyl which is unsubstituted or substituted with halogen; C₃ to C₆ cycloalkylamino; C₁ to C₆ alkoxy; C₁ to C₆ alkanoyloxy; C₂ to C₆ alkenyloxy; phenyl -C₁ to C₆ alkoxy; phenoxy; C₂ to C₆ alkenoyloxy or phenyl -C₁ to C₆ alkanoyloxy; or C₃ to C₆ cycloalkyloxy which is substituted with one group selected from carboxy, esterified carboxy and amidated carboxy; or aminooxy;

R₅ is hydrogen or hydroxy group;

R₆ and R₇ are each independently hydrogen; C₁ to C₆ alkyl which is unsubstituted or substituted with one group selected from hydroxy, C₁ to C₆ alkoxy, pyridine and

phenyl; benzyl; pyridinyl; carbonyl which is unsubstituted or substituted with one group selected from C₁ to C₆ alkyl, hydroxy, C₁ to C₆ alkoxy, phenyl, benzyl, pyridine and

or C₁ to C₆ alkanesulfonyl;

R₈ and R₉ are each independently hydrogen; C₁ to C₆ alkyl which is unsubstituted or substituted with one group selected from hydroxy, C₁ to C₆ alkoxy, morpholine, imidazole and NR₆R₇; C₁ to C₆ alkoxy; C₃ to C₆ cycloalkyl; phenyl; benzyl; pyridinyl; morpholine; carbonyl which is unsubstituted or substituted with one group selected from C₁ to C₆ alkyl, C₁ to C₆ alkoxy, phenyl, benzyl, pyridine and

carbonyl substituted with C₁ to C₆ alkyl which is substituted with one group selected from halogen, C₁ to C₆ alkoxy and imidazole; or C₁ to C₆ alkanesulfonyl;

R₁₀ and R₁₁ are each independently hydrogen, C₁ to C₂ alkyl, C₁ to C₃ alkoxy or halide;

X₁ and X₃ are each independently O; S; NH; or N—C₁ to C₆ alkyl, N—C₃ to C₆ cycloalkyl, N-benzyl or N-phenyl;

X₂ is C₃ to C₇ alkylene; C₁ to C₃ alkylene-C₂ to C₇ alkenylene-C₁ to C₃ alkylene; C₁ to C₃ alkylene-O—C₁ to C₃ alkylene; C₁ to C₃ alkylene-S—C₁ to C₃ alkylene; C₁ to C₃ alkylene-NH—C₁ to C₃ alkylene; C₁ to C₃ alkylene -phenylene-C₁-C₃ alkylene; C₁-C₃ alkylene-pyridylene-C₁-C₃ alkylene or C₁-C₃ alkylene -naphthylene-C₁ to C₃ alkylene; C₃ to C₇ alkylene which is substituted with C₁ to C₃ alkyl and hydroxyl; C₃ to C₇ alkylene carbonyl; or C₃ to C₇ alkylene which is interrupted by piperazine;

Y is O, S, NR₆ or CH₂;

Q is CH₂ or carbonyl; and n is an integer of 0 to 6, or a pharmaceutically acceptable salt thereof.

2. The benzamidine derivative or the pharmaceutically acceptable salt thereof according to claim 1, wherein R₁ is methyl, ethyl, isopropyl, cyclohexyl, phenyl, pyridinyl, NR₆R-7, CHZNR₆R,7,

or

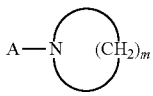

(wherein A is C, to $C_2$ alkyl, and m is an integer of 4 to 5);
$R_2$ is a primary or secondary amine, which is $NR_8R_9$,

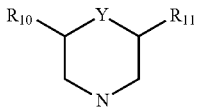

piperdine or imidazole;
  $R_3$ and $R_4$ are each independently hydrogen, methyl, ethyl, halogen, hydroxy or methoxy;
  $R_5$ is hydrogen or hydroxy;
  $R_6$ and $R_7$ are each independently hydrogen, methyl, ethyl, isobutyryl, methoxyethyl, 2-morpholinoethyl or benzyl;
  $R_8$ and $R_9$ are each independently hydrogen; methyl; ethyl; propyl; isopropyl; butyl; isobutyl ; t-butyl; cyclopropyl; cyclohexyl; ethyl which is substituted with one group selected from hydroxy, methoxy, 2-morpholino and $NR_6R_7$ ; propyl which is substituted with one group selected from 3-isopropoxy and 3-imidazole ; carbonyl which is substituted with one group selected from 3-pyridinyl 4-pyridinyl and isopropyl;
  $R_{10}$ and $R_{11}$ are each independently hydrogen or methyl;
  $X_1$ and $X_3$ are each independently oxygen, sulfur, amine or methylamine;
  $X_2$ is propylene, butylene, pentylene, hexylene, ethylene-O-ethylene, ethylene-NH-ethylene, butylene carbonyl, 2-butenyl, methylene-1,2-phenylene-methylene, methylene-1, 3-phenylene-methylene, methylene-1,4-phenylene-methylene or methylen e-pyridinyl-methylene;
  Y is O, S or methylamino;
  Q is $CH_2$ or carbonyl; and n is an integer of 0 to 3.

3. The benzamidine derivative or the pharmaceutically acceptable salt thereof according to claim 1, wherein the pharmaceutically acceptable salt is hydrochloride or methanesulfonate.

4. The benzamidine derivative or the pharmaceutically acceptable salt thereof according to claim 1, which is selected from the group consisting of:
1)   N-hydroxy-(5-{4-[-5-(2-isobutylamino-ethyl)-2-methyl-thiazol-4-yl]-phenoxy}-pentyloxy) -benzamidine,
2) 4-(5-{4-[5-(2-isobutylaminoethyl)-2-methyl-thiazol-4-yl]-phenoxy}pentyloxy)-benzamidine,
3)   N-hydroxy-4-(5-{4-[2-methyl-5-(2-piperidin-1-yl-ethyl)-thiazol-4-yl]-phenoxy}-pentyloxy)   -benzamidine,
4) N-hydroxy-4-[5-(4-{2-methyl-5-[2-(2-morpholin-4-yl-ethylamino)-ethyl]-thiazo1-4-y 1}-phenoxy)-pentyloxy]-benzamidine,
5)   N-hydroxy-4-[5-(4-{5-[2-(3-imidazol-l-yl-propylamino)-ethyl]-2-methyl-thiazol-4-yl]-phenoxy)-pentyloxy]-benzamidine,
6)   N-hydroxy-4-(5-{4-[5-(2-isopropyl amino-ethyl)-2-methyl-thiazol-4-yl]-phenoxy}-pentyloxy)   -benzamidine,
7)   N-hydroxy-4-[5-(4-{5-[2-(3-isopropoxy-propylamino)-ethyl]-2-methyl-thiazol-4-yl]-phenoxy) -pentyloxy]-benzamidine, 8) N-hydroxy-4-(5-{4-[5-(2-butylamino-ethyl)-2-methyl-thiazol-4-yl]-phenoxy}-p entyloxy)-N-hydroxy-benzamidine,
9)   N-hydroxy-4-(5-{4-[5-(2-imidazol-1-yl-ethyl)-2-methyl-thiazol-4-yl]-phenoxy}-pentyloxy)-benzamidine,
10)  N-hydroxy-4-(5-{4-[5-(2-cyclohexylamino-ethyl)-2-methyl-thiazol-4-yl]-phenoxy-pentyloxy)   -benzamidine,
11)  N-hydroxy-4-(5-{4-[5-(2-diethylamino-ethyl)-2-methyl-thiazol-4-yl]-phenoxy}-pentyloxy)-benzamidine,
12)   N-hydroxy-4-{5-[4-(5-{2[bis-(2-hydroxy-ethyl)-amino]-ethyl}-2-methyl-thiazo1-4-yl) -phenoxy]pentyloxy}-benzamidine,
13)  N-hydroxy-4-(5-{4-[5-(2-diisopropylamino-ethyl)-2-methyl-thiazol-4-yl]-phenoxy}-pentyloxy)-benzamidine,
14) N-hydroxy-4-[5-(4-{5-[2-(2,6-dimethyl-morpholin-4-yl)-ethyl]-2-methyl-thiazol-4-y1}-phenoxy)-pentyloxy]-benzamidine,
15)  N-hydroxy-4-(5-{4-[2-methyl-5-(2-thiomorpholin-4-yl-ethyl)-thiazol-4-yl]-phenoxy}-pentyloxy)-benzamidine,
16)   N-hydroxy-4-(5-{4-[2-amino-5-(2-morpholin-4-yl-ethyl)-thiazol-4-yl]-phenoxy}-pentyloxy)-benzamidine,
17)   N-hydroxy-4[5-(4-{5-[2-(2-dimethylamino-ethylamino)-ethyl]-2-methyl-thiazol-4-yl}-phenoxy)-pentyloxy]-benzamidine,
18)  N-hydroxy-4-(5-{4-[2-methyl -5-(2-morpholin-4-yl-ethyl)-thiazol-4-yl]-phenoxy}-pentyloxy)-benzamidine,
19)  N-hydroxy-4-[5-( 4-{2-methyl-5-[2-(4-methyl-piperazin-1-yl)-ethyl]-thiazol-4-yl}-phenoxy)-pentyloxy]-benzamidine,
20)   N-hydroxy-4-{5-[4-(5-{2-[bis-(2-methoxy-ethyl)-amino]-ethyl}-2-methyl-thiazol-4-yl}-phenoxy]-pentyloxy) -benzamidine,
21)   N-hydroxy-4-(5-{4-[5-(2-tert-butylamino-ethyl)-2-methyl-thiazol-4-yl]-phenoxy}-pentyloxy)-benzamidine,
22) N-hydroxy-4-(5-{4-[5-(2-isobutylamino-ethyl)-2-methyl-thiazol-4-yl]-phenoxy}-pentyloxy)-benzamidine,
23)   N-hydroxy-4-(5-{4-[5-(2-morpholin-4-yl-ethyl)-2-pyridine-3-yl-thiazol-4-yl]-phenoxy}-pentyloxy)-benzamidine,
24)   N-hydroxy-4-[5-(4-{5-[2-(4-methyl-piperazin-l-yl)-ethyl]-2-pyridine-3-yl-thiazol-4-yl}-phenoxy)-pentyloxy]-benzamidine,
25) N-hydroxy-4-(5-{4[2-pyridine-3-yl-5-(2-thiomorpholin-4-yl-ethyl)-thiazol-4-yl]-phenoxy}pentyloxy)-benzamidine,
26) N-hydroxy-4-(5-{4[5-(2-imidazol-1-yl-ethyl)-2-pyridine-3-yl-thiazol-4-]-phenoxy}-pentyloxy)-benzamidine,
27) N-hydroxy-4-(5-{4[2-isopropyl-5-(2-morpholin-4-yl-ethyl)-thiazol-4-yl]-phenoxy}-pentyloxy)-benzamidine,
28)  N-hydroxy-4-[5-(4-{2-isopropyl-5[2-(4-methyl-piperazin-l-yl)-ethyl]-thiazol-4-   y1}-phenoxy)-pentyloxy]-benzamidine,
29)  N-hydroxy-4-(5-{4-[5-(2-imidazol-1-yl-ethyl)-2-isopropyl-thiazol-4-yl]-phenoxy}-pentyloxy)-benzamidine,
30)  N-hydroxy-4-[5-(4-{2-isopropyl-5-[2-(2-morpholin-4-yl-ethyl  amino)-ethyl]-thiazol-4-yl}-phenoxy)-pentyloxy]-benzamidine, 31) N-hydroxy-4-[5-(4-{5-[2-(3-imidazol-1-yl-propylamino)-ethyl]-2-isopropyl-thiazol -yl}phenoxy)-pentyloxy]-benzamidine,
32) N-hydroxy-4-(5-{4-[2-isopropyl-5-(2-thiomorpholin-4-yl-ethyl)-thiazol-4-yl]-phenoxy}-pentyloxy)-benzamidine,
33) N-hydroxy-4-(5-{4-[2-cyclohexyl-5-(2-morpholin-4-yl-ethyl)-thiazol-4-yl]-phenoxy}-pentyloxy)-benzamidine,
34) N-hydroxy-4[5-(4-{2-cyclohexyl-5-[2-(4-methyl-piperazin-1-yl)-ethyl]-thiazol-4-yl}-phenoxy)-pentyloxy]-benzamidine,
35) N-hydroxy-4[5-(4-{2-cyclohexyl-5-[2-(2-morpholin-4-yl-ethylamino)-ethyl]-thiazol-4-yl}-phenoxy)-pentyloxy]benzamidine,
36) N-hydroxy-4-(5-{4-[2-cyclohexyl-5-(2-thiomorpholin-4-yl-ethyl)-thiazol-4-yl]-phenoxy}-pentyloxy)-benzamidine,
37) N-hydroxy-4-(5-{4-[2-cyclohexyl-5-(2-dimethylamino-ethyl)-thiazol-4-y1]-phenoxy}-pentyloxy)-benzamidine,
38) N-hydroxy-4-(5-{4-[2-cyclohexyl-5-(2-dipropylamino-ethyl)-thiazol-4-yl]-phenoxy}-pentyloxy)-benzamidine,
39) N-hydroxy-4-(5-{4[2-cyclohexyl-5-(2-cyelopropylamino-ethyl)-thiazol-4-yl]-phenoxy}-pentyloxy)-benzamidine,
40) N-hydroxy-4[5-(4-{2-amino-5-[2-(2-morpholin-4-yl-ethylamino)-ethyl]-thiazol-4-yl}-phenoxy)-pentyloxy]-benzamidine,
41) N-hydroxy-4-(5-{4-[5-(2-morpholin-4-yl-ethyl)-2-phenyl-thiazol-4-yl]-phenoxy}-pentyloxy)-benzamidine,
42) N-hydroxy-4-(5-{4[2-ethyl-5-(2-morpholin-4-yl-ethyl)-thiazol-4-yl]-phenoxy}-pentyloxy)-benzamidine,
43) N-hydroxy-4-(5-{4-[2-ethyl-5-(2-thiomorpholin-4-yl-ethyl)-thiazol-4-yl]-phenoxy}pentyloxy)-benzamidine,
44) N-hydroxy-4-(4-{4-[2-methyl-5-(2-morpholin-4-yl-ethyl)-thiazol-4-yl]-phenoxy}butoxy)-benzamidine,
45) 4-(5-{4-[2-cyclohexyl-5-(2-morpholin-4-yl-ethyl)-thiazol-4-yl]-phenoxy}pentyloxy) -benzamidine,
46) 4-(5-{4[2-methyl-5-(2-morpholin-4-yl-ethyl)-thiazol-4-yl]-phenoxy]-pentyloxy) -benzamidine,
47) N-hydroxy-4-(5-{4-[2-methylamino-5-(2-morpholin-4-yl-ethyl)-thiazol-4-yl]-phenoxy}-pentyloxy)-benzamidine,
48) N-hydroxy-4-[5-(4-{2-methylamino-5-[2-(4-methyl-piperazin-1-yl)-ethyl]thiazol-4-yl}-phenoxy)-pentyloxy]-benzamidine,
49) N-hydroxy-4-(5-{4[2-methylamino-5-(2-thiomorpholin-4-yl-ethyl)-thiazol-4-yl]-phenoxy}-pentyloxy)-benzamidine,
50) N-hydroxy-4-[5-(4-{2-methylamino-5[2-(2-morpholin-4-yl-ethylamino)-ethyl]-thiazol-4-yl}-phenoxy)-pentyloxy]-benzamidine,
51) N-hydroxy-4-[5-(4-{5-[2-(3-imidazol-1-yl-propylamino)-ethyl]-2-methylaminothiazol-4-yl}-phenoxy)-pentyloxy]-benzamidine,
52) 4-(5-{4-[2-methylamino-5-(2-morpholin-4-yl-ethyl)-thiazol-4-yl]-phenoxy}-pentyloxy) -benzamidine,
53) N-hydroxy-4-(5-{4-[2-dimethylamino-5-(2-morpholin-4-yl-ethyl)-thiazol-4-yl]-phenoxy}-pentyloxy)-benzamidine,
54) N-hydroxy-4-(5-{4-[2-dimethylamino-5-(2-thiomorpholin-4-yl-ethyl)-thiazol-4-yl]-phenoxy}-pentyloxy)-benzamidine,
55) N-hydroxy-4-(5-{4-[2-(isobutyryl-methyl-amino)-5-(2-morpholin-4-yl-ethyl)-thiazol -4-yl]-phenoxy}-pentyloxy)-benzamidine,
56) N-hydroxy-4-(5-{4-[2-[benzyl-(2-morpholin-4-yl-ethyl)-amino]-5-(2-morpholin-4-yl-ethyl)-thiazol-4-yl]-phenoxy}-pentyloxy)-benzamidine,
57) N-hydroxy-4-(5-14-[2-diethylamino-5-(2-morpholin-4-yl-ethyl)-thiazol-4-yl]-phenoxy}-pentyloxy)-benzamidine,
58) N-hydroxy-4-(5{4-[2-[bis-(2-methoxy-ethyl)-amino]-5-(2-morpholin-4-yl-ethyl) -thiazol-4-yl]-phenoxy}-pentyloxy)-benzamidine,
59) N-hydroxy-4-(5-{4-[2-morpholin-4-yl-5-(2-morpholin-4-yl-ethyl)-thiazol-4-yl]-phenoxy}-pentyloxy)-benzamidine,
60) N-hydroxy-4-(5-14-[2-morpholin-4-yl-5-(2-thiomorpholin-4-yl-ethyl)-thiazol-4-yl]-phenoxy}-pentyloxy)-benzamidine,
61) N-hydroxy-4-[5-(4-{5-[2-(4-methyl-piperazin-1-yl)-ethyl]-2-morpholin-4-yl-thiazol-4-yl}-phenoxy)-pentyloxy]-benzamidine,
62) N-hydroxy-4-[5-(4-{2-morpholin-4-y1-5-[2-(2-morpholin-4-yl-ethylamino)-ethyl]-thiazol-4-yl}-phenoxy)-pentyloxy]-benzamidine,
63) N-hydroxy-4-(5-14-[5-(2-morpholin-4-yl-ethyl)-2-piperidin-1-yl-methyl-thiazol-4-yl]-phenoxy}-pentyloxy)-benzamidine,
64) 4-(5-{4-[2-morpholin-4-yl-5-(2-morpholin-4-yl-ethyl)-thiazol-4-yl]-phenoxy}-pentyloxy)-benzamidine,
65) N-hydroxy-(5-{4-[5-(2-isobutyrylamino-ethyl)-2-methyl-thiazol-4-yl]-phenoxy}-pentyloxy)-benzamidine
66) N-hydroxy-4-{5-[4-(5-{2-[isobutyl-(pyridine-3-carbonyl)-amino]-ethyl}-2-methylthiazol-4-yl)-phenoxy]-pentyloxy}-benzamidine,
67) N-hydroxy-4-{5-[4-(5-{2-[cyclopropyl-(pyridine-4-carbonyl)-amino]-ethyl}-2-isopropyl-thiazol-4-yl)-phenoxy]-pentyloxy}-benzamidine,
68) N-hydroxy-4-{5[4-(2-cyclohexyl-5-{2-[cyclopropyl-(pyridine-3-carbonyl)-amino]-ethyl}-thiazol-4-yl)-phenoxy]-pentyloxy}-benzamidine,
69) N-hydroxy-4-{5-4-(5-methylcarbamoyl-2-methyl-thiazol-4-yl)-phenoxy]-pentyloxy}benzamidine,
74) N-hydroxy-4-{5-[4-(5-isopropylcarbamoyl-2-methyl-thiazol-4-yl)-phenoxy]-pentyloxy}-benzamidine,
71) N-hydroxy-4-{5-[4-(5-{3-imidazol-1-yl-propylcarbamoyl}-2-methyl-thiazol-4-yl)-phenoxy]-pentyloxy}-benzamidine, and
72) N-hydroxy-4-{5-[4-(2-amino-5-methylcarbamoyl-thiazol-4-yl)-phenoxy]-pentyloxy}-benzamidine.

5. A method for preparing a benzamidine derivative represented by the following formula 1a, or a pharmaceutically acceptable salt thereof, comprising the steps of:
1) reacting a compound of the formula 2 with a compound of the formula 3 in the presence of an inorganic base to prepare a compound of the formula 4;
2) reacting a compound of the formula 5 with the compound of the formula 4 obtained in the step 1) in the presence of an inorganic acid to prepare a compound of the formula 6;
3) reacting the compound of the formula 6 obtained in the step 2) with an acid chloride compound (7) to prepare a benzonitrile derivative of the formula 8;
4) reacting the compound of the formula 8 obtained in the step 3) with a bromine compound to prepare an alpha-brominated compound of the formula 9;

5) reacting the alpha-brominated compound of the formula 9 obtained in the step 4) with a thioamide compound of the formula 10 to prepare a benzonitrile derivative of the formula 11 with a thiazole ring;
6) reacting the compound of the formula 11 obtained in the step 5) with sodium iodide to prepare a benzonitrile derivative of the formula 12;
7) reacting the compound of the formula 12 obtained in the step 6) with a primary or secondary amine compound of the formula 13 to prepare a benzonitrile derivative of the formula 14; and
8) reacting the compound of the formula 14 obtained in the step 7) with hydroxylamine hydrochloride or an ammonia ethanol solution to prepare a benzamidine derivative of the formula 1a or a pharmaceutically acceptable salt thereof;

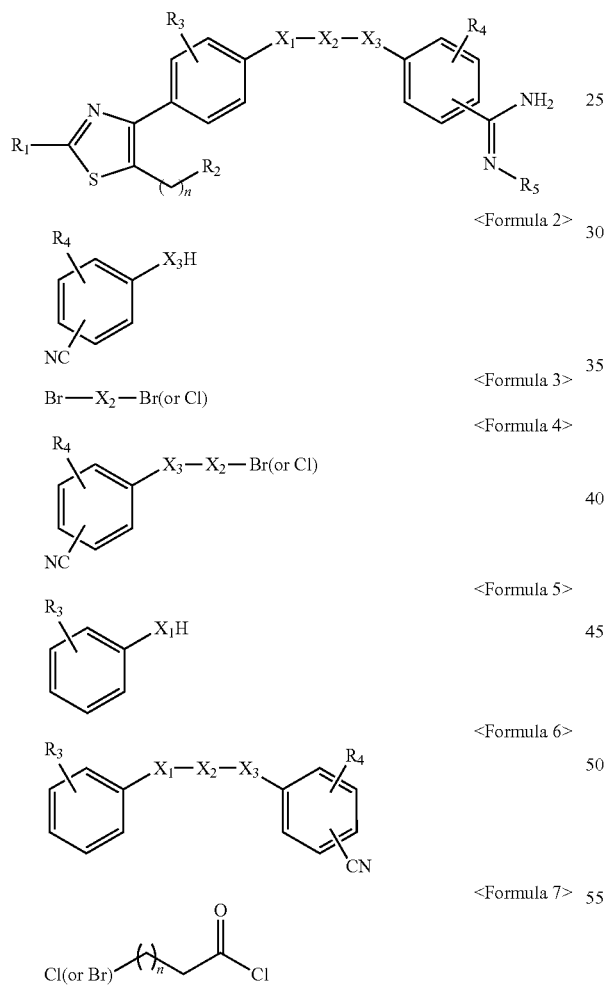

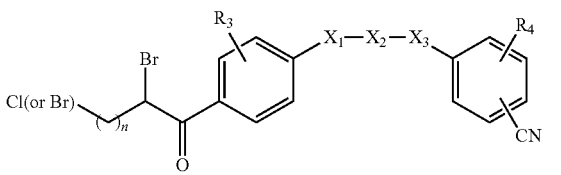

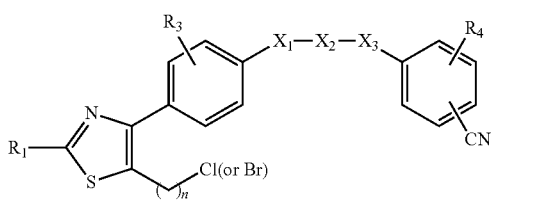

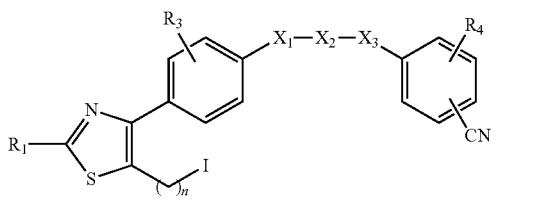

$R_2$ (=1° or 2° amine)

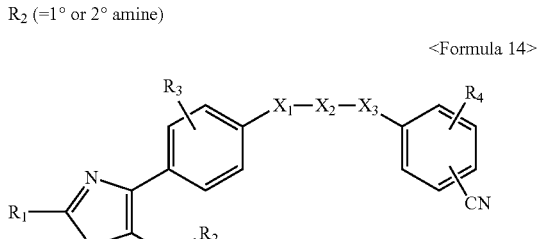

wherein $R_1$ is $C_1$ to $C_6$ alkyl; $C_1$ to $C_6$ alkyl which is substituted with pyridine; $C_3$ to $C_6$ cycloalkyl; benzyl; phenyl; amino; guanidino; pyridinyl; pyridinyl which is substituted with $C_1$ to $C_6$ alkyl;

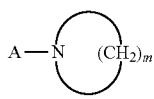

or (wherein A is $C_1$ to $C_6$ alkyl, and m is an integer of 2 to 6), and $R_2$, $R_3$, $R_4$, $R_5$, $X_1$, $X_2$, $X_3$ and n are the same as defined in claim 1.

6. A method for preparing a benzamidine derivative represented by the following formula 1b, or a pharmaceutically acceptable salt thereof, comprising the steps of:
1) reacting the alpha-brominated compound of the formula 9 obtained in the step 4) of claim 5 with the thioamide compound of the formula 15 to prepare a benzonitrile derivative of the formula 16 with a thiazole ring;
2) reacting the compound of the formula 16 obtained in the step 1) with sodium iodide to prepare a benzonitrile derivative of the formula 17;

3) reacting the compound of the formula 17 obtained in the step 2) with a primary or secondary amine compound of the formula 13 to prepare a benzonitrile derivative of the formula 18;
4) reacting the compound of the formula 18 obtained in the step 3) with a halide compound of the formula 19 to prepare a benzonitrile derivative of the formula 20 with a thiazole ring, which is substituted with a primary amine; and
5) reacting the compound of the formula 20 obtained in the step 4) with hydroxylamine hydrochloride or an ammonia ethanol solution to prepare a benzamidine derivative of the formula 1b or a pharmaceutically acceptable salt thereof:

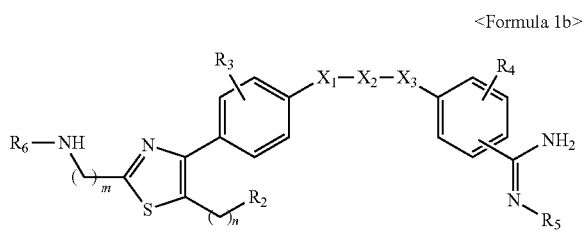

<Formula 1b>

<Formula 15>

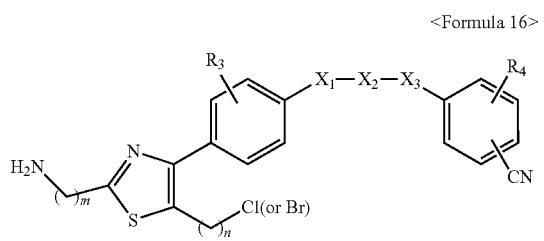

<Formula 16>

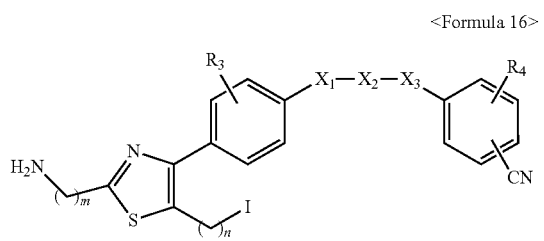

<Formula 16>

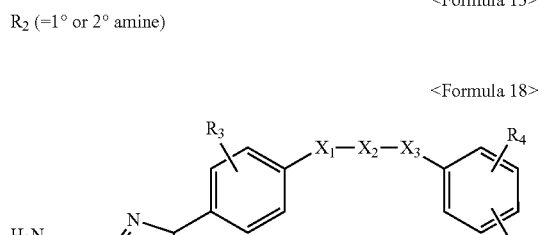

<Formula 13>

R$_2$ (=1° or 2° amine)

<Formula 18>

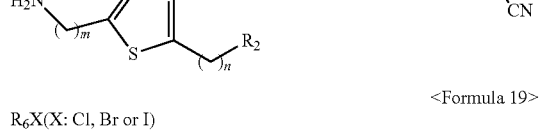

<Formula 19>

R$_6$X(X: Cl, Br or I)

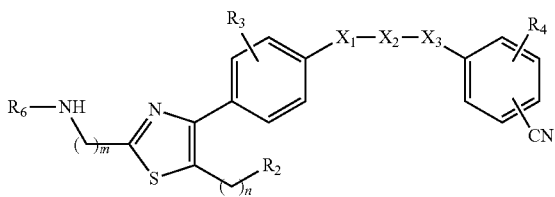

<Formula 20> wherein R$_2$, R$_3$, R$_4$, R$_5$, R$_6$, X$_1$, X$_2$, X$_3$ and n are the same as defined in claim 1 and m is an integer of 0 to 6, with the proviso that R$_6$ is not hydrogen.

7. A method for preparing a benzamidine derivative represented by the following formula 1c, or a pharmaceutically acceptable salt thereof, comprising the steps of:
1) reacting the compound of the formula 20 obtained in the step 4) of claim 6 with a halide compound of the formula 21 to prepare a benzonitrile derivative of the formula 22 with a thiazole ring, which is substituted with a secondary amine; and
2) reacting a compound of the formula 22 obtained in the step 1) with hydroxylamine hydrochloride or an ammonia ethanol solution to prepare a benzamidine derivative of the formula 1e or a pharmaceutically acceptable salt thereof:

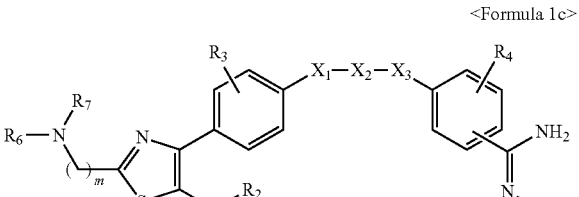

<Formula 1c>

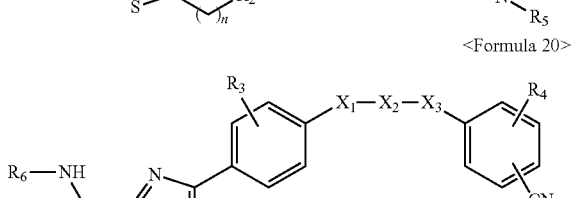

<Formula 20>

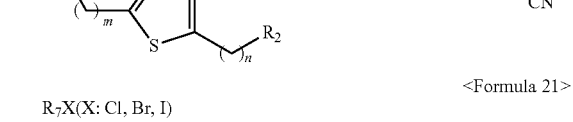

<Formula 21>

R$_7$X(X: Cl, Br, I)

<Formula 22>

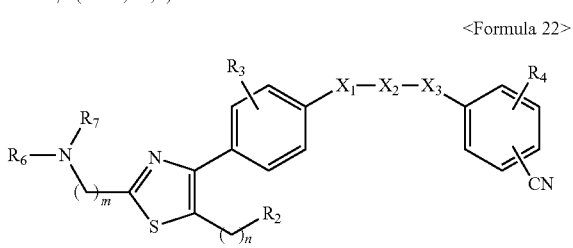

wherein R$_2$, R$_3$, R$_4$, R$_5$, R$_6$ R$_7$, X$_1$, X$_2$, X$_3$ and n are the same as defined in claim 1 and m is an integer of 0 to 6, with the proviso that R$_6$ and/or R$_7$ is/are not hydrogen.

8. A method for preparing a benzamidine derivative represented by the following formula 1d, or a pharmaceutically acceptable salt thereof, comprising the steps of:
1) reacting the compound of the formula 18 obtained in the step 3) of claim 6 with a compound, of which both terminals are substituted with a halogen, of the formula 23 to prepare a benzonitrile derivative of the formula 24 with a thiazole ring, which is substituted with a heteroring; and 2) reacting a compound of the formula 24 obtained in the step 1) with hydroxylamine hydrochloride or an ammonia ethanol solution to prepare a benzamidine derivative of the formula 1d or a pharmaceutically acceptable salt thereof:

<Formula 1d>

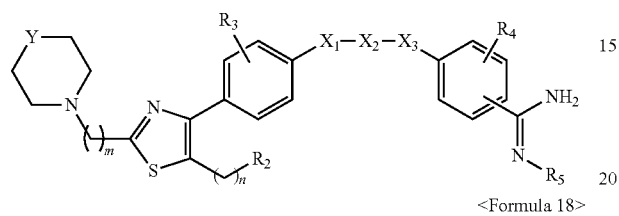

<Formula 23>

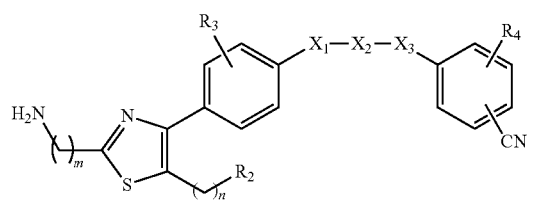

(or Cl)Br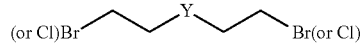Br(or Cl)

<Formula 24>

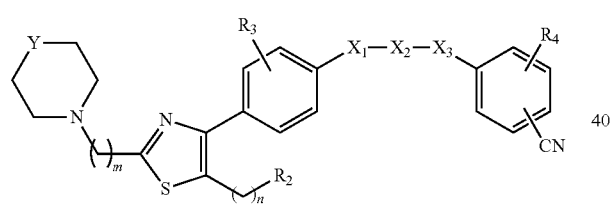

wherein $R_2$, $R_3$, $R_4$, $R_5$, $X_1$, $X_2$, $X_3$, Y and n are the same as defined in claim 1, and m is an integer of 0 to 6.

9. A method for preparing a benzamidine derivative represented by the following formula 1e, or a pharmaceutically acceptable salt thereof, comprising the steps of:

1) reacting the compound of the formula 12 obtained in the step 6) of claim 5 with potassium phthalimide to prepare a benzonitrile derivative of the formula 25;

2) reacting the compound of the formula 25 obtained in the step 1) with hydrazine hydrate to prepare a benzonitrile derivative containing an amino group of the formula 26;

3) reacting the compound of the formula 26 obtained in the step 2) with a halide compound of the formula 27 to prepare a benzonitrile derivative which is substituted with a primary amine compound of the formula 14a; and 4) reacting the compound of the formula 14a obtained in the step 3) with hydroxylamine hydrochloride or an ammonia ethanol solution to prepare a benzamidine derivative of the formula 1e or a pharmaceutically acceptable salt thereof:

<Formula 1e>

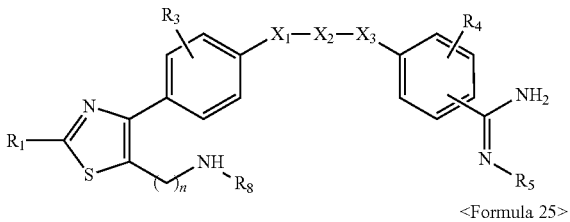

<Formula 25>

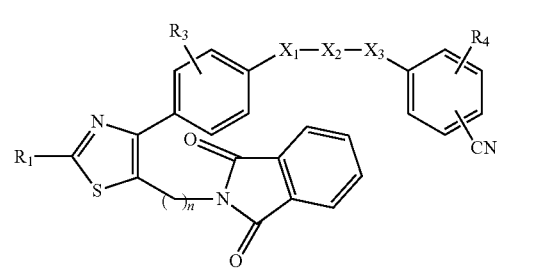

<Formula 26>

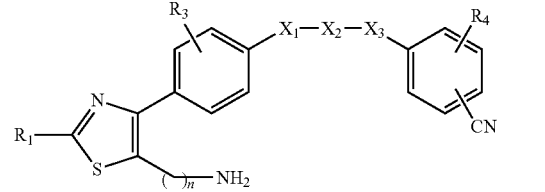

$R_8X(X: Cl, Br, I)$

<Formula 27>

<Formula 14a>

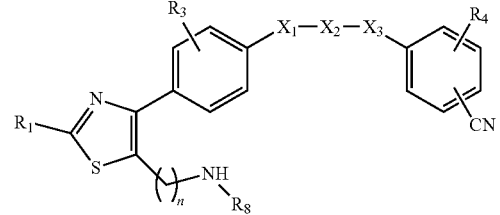

wherein $R_1$, $R_3$, $R_4$, $R_5$, $X_1$, $X_2$, $X_3$ and n are the same as defined in claim 1 with proviso that $R_8$ is not hydrogen; and R8 is carbonyl which is unsubstituted or substituted with one group selected from $C_1$ to $C_6$ alkyl, $C_1$ to $C_6$ alkoxy, phenyl, benzyl, pyradine and

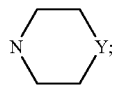

or carbonyl substituted with $C_1$ to $C_6$ alkyl which is substituted with one group selected from halogen, $C_1$ to $C_6$ alkoxy and imidazole.

10. A method for preparing a benzamidine derivative represented by the following formula 1f, or a pharmaceutically acceptable salt thereof, comprising the steps of:

1) reacting the compound of the formula 12 obtained in the step 6) of claim 5 with a primary amine compound of the formula 13 to prepare a benzonitrile derivative of the formula 14b;

2) reacting the compound of the formula 14b obtained in the step 1) with a halide compound of the formula 28 to prepare a benzonitrile derivative which is substituted with a secondary amine compound of the formula 29; and 3) reacting the compound of the formula 29 obtained in the step 2) with hydroxylamine hydrochloride or an ammonia ethanol solution to prepare a benzamidine derivative of the formula 1f or a pharmaceutically acceptable salt thereof:

<Formula 1f>

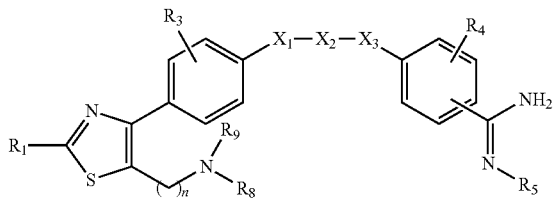

<Formula 14b>

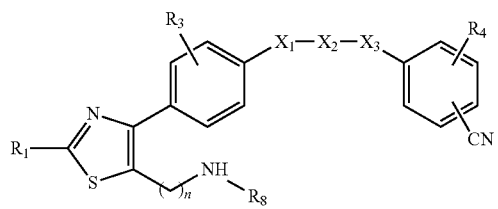

R₉X(X: Cl, Br, I)

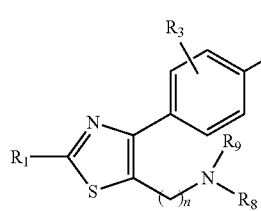

<Formula 28>

<Formula 29>

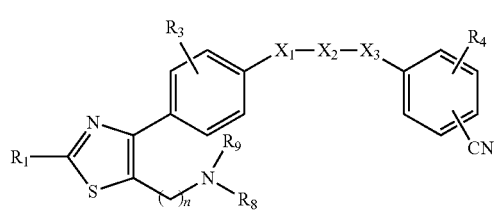

wherein R₁, R₂, R₄, R₅, R₉, X₁, X₂, X₃ and n are the same as defined in claim 1 with proviso that both of R₈ R₉ are not hydrogen; and R₈ is hydrogen which is unsubstituted or substituted with one group selected from the group consisting of hydroxy, $C_1$ to $C_6$ alkoxy, morpholine, imidazole and NR₆R₇; $C_1$ to $C_6$ alkoxy; $C_3$ to $C_6$ cycloalkyl; phenyl; benzyl; pyridinyl; morpholine; or $C_1$ to $C_6$ alkanesulfonyl.

11. A method for preparing a benzamidine derivative represented by the following formula 1g, or a pharmaceutically acceptable salt thereof, comprising the steps of:

1) reacting a compound of the formula 30 with the compound of the formula 4 obtained in the step 1) of claim 5 in the presence of an inorganic base to prepare a compound of the formula 31;
2) reacting the compound of the formula 31 obtained in the step 1) with sodium hydride, and diethyl carbonate to prepare a compound of the formula 32;
3) reacting the compound of the formula 32 obtained in the step 2) with a bromine compound to prepare an alpha-brominated compound of the formula 33;
4) reacting the alpha-brominated compound of the formula 33 obtained in the step 3) with a thioamide compound of the formula 10 to prepare a compound of the formula 34 with a thiazole ring;
5) reacting the compound of the formula 34 obtained in the step 4) with lithium hydroxide to prepare a compound of the formula 35;
6) reacting the compound of the formula 35 obtained in the step 5) with isobutyl chloroformate and an amine to prepare a benzonitrile derivative of the formula 36; and
7) reacting the compound of the formula 36 obtained in the step 6) with hydroxylamine hydrochloride or an ammonia ethanol solution to prepare a benzamidine derivative of the formula 1g:

<Formula 1g>

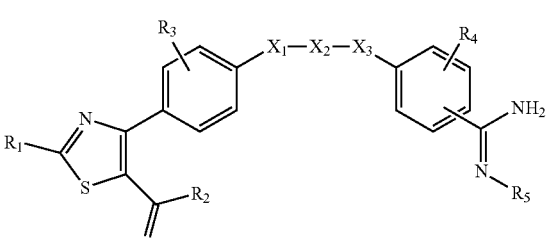

<Formula 30>

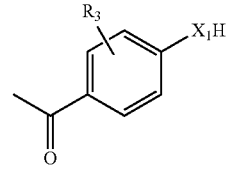

<Formula 31>

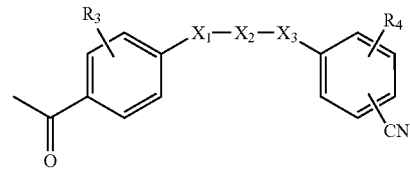

<Formula 32>

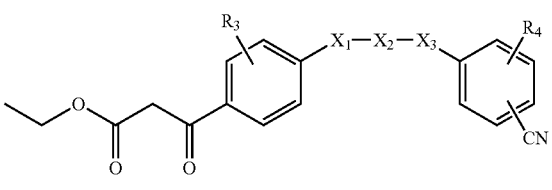

<Formula 33>

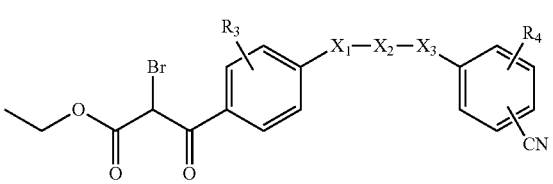

<Formula 34>

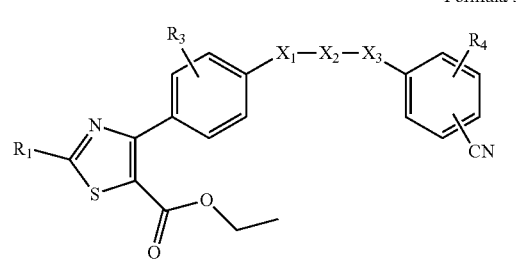

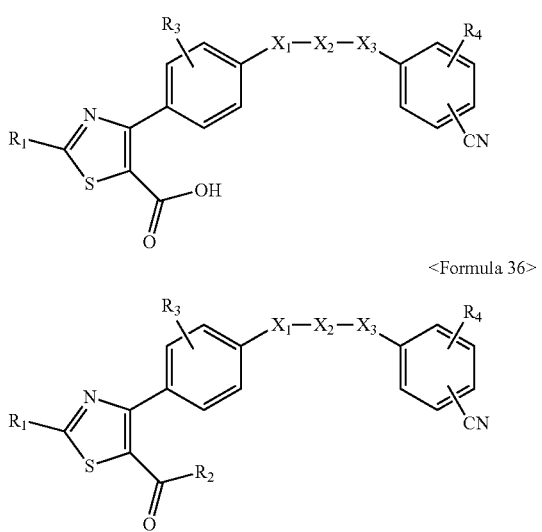

<Formula 35>

<Formula 36> wherein $R_1$ is $C_1$ to $C_6$ alkyl; $C_1$ to $C_6$ alkyl which is substituted with pyridine; $C_3$ to $C_6$ cycloalkyl; benzyl; phenyl; amino; guanidino; pyridinyl; pyridinyl which is substituted with $C_1$ to $C_6$ alkyl; or

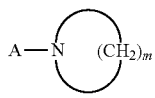

(wherein A is $C_1$ to $C_6$ alkyl, and m is an integer of 2 to 6), and $R_2$, $R_3$, $R_4$, $R_5$, $X_1$, $X_2$ and X3 are the same as defined in claim 1.

12. The method for preparing the benzamidine derivative or the pharmaceutically acceptable salt thereof according to claim 5 or 11, wherein the thioamide compound of the formula 10 is selected from the group consisting of thioacetamide, thiopropionamide, thioisobutyramide, trimethylthioacetamide, thiohexanoamide, cyclohexancarbothioicacid amide, and piperidin-4-carbothioic acid amide.

13. The method for preparing the benzamidine derivative or the pharmaceutically acceptable salt thereof according to any one of claim 6, 7, 9 or 10, wherein the halide compounds of the formulae 19, 21, 27 and 28 are selected from the group consisting of iodomethane, iodoethane, propylbromide, 2-chloroethyl methyl ether, chloroethyl morpholine, 3-bromomethyl pyridine, bromoethanol, benzyl bromide, nicotinoyl chloride, ethanesulfonyl chloride and isonicotinoyl chloride.

14. The method for preparing the benzamidine derivative or the pharmaceutically acceptable salt thereof according to claim 8, wherein the compound, of which both terminals are substituted with a halogen, of the formula 23 is selected from the group consisting of mechlorethylamine, dibromoethyl ether and dibromopentane.

15. The method for preparing the benzamidine derivative or the pharmaceutically acceptable salt thereof according to any one of claims 5 to 11, wherein in the step of converting benzonitrile into benzamidine, in the case of $R_5$=OH, the amine to be used is hydroxylamine hydrochloride; and the hydroxylamine hydrochloride is reacted in the presence of an organic base and inorganic at 60 to 80° C. for 1 to 9 hrs in a single solvent selected from the group consisting of methanol, ethanol and acetonitrile, or a mixed solvent thereof with water.

16. A method of treating osteoporosis, the method comprising administering to a patient in need thereof, a therapeutically effective amount of the compound or the pharmaceutically acceptable salt thereof according to any one of claims 1 to 4.

17. The method for preparing the benzamidine derivative or the pharmaceutically acceptable salt thereof according to claim 15, wherein the organic base is selected from the group consisting of triethylamine, 1,8-diazabicyclo[5.4.0]undec-7-ene (DBU), diethylmethylamine ($Et_2NMe$), N-methylmorpholine, N-methylpiperidine, pyridine and 2,6-dimethylpyridine.

18. The method for preparing the benzamidine derivative or the pharmaceutically acceptable salt thereof according to claim 15, wherein the inorganic bases are selected from the group consisting of potassium carbonate, potassium bicarbonate, sodium hydroxide, potassium hydroxide, sodium amide, sodium hydride, sodium methoxide, and sodium ethoxide.

* * * * *